(12) United States Patent
Astles et al.

(10) Patent No.: US 7,408,067 B2
(45) Date of Patent: Aug. 5, 2008

(54) AZA-CYCLIC COMPOUNDS AS MODULATORS OF ACETYLCHOLINE RECEPTORS

(75) Inventors: Peter Charles Astles, Basingstoke (GB); Stephen Richard Baker, Basingstoke (GB); Celine Bonnefous, San Diego, CA (US); Jean Michel Vernier, San Diego, CA (US); Martine Keenan, Basingstoke (GB); Adam Jan Sanderson, Basingstoke (GB)

(73) Assignee: Merck + Co., Inc., Rahway, NJ (US)

( * ) Notice: Subject to any disclaimer, the term of this patent is extended or adjusted under 35 U.S.C. 154(b) by 390 days.

(21) Appl. No.: 10/500,517

(22) PCT Filed: Jul. 29, 2002

(86) PCT No.: PCT/US02/21297

§ 371 (c)(1),
(2), (4) Date: Jun. 29, 2004

(87) PCT Pub. No.: WO03/062224

PCT Pub. Date: Jul. 31, 2003

(65) Prior Publication Data

US 2005/0070520 A1    Mar. 31, 2005

Related U.S. Application Data

(60) Provisional application No. 60/350,150, filed on Jan. 17, 2002.

(51) Int. Cl.
*C07D 211/22* (2006.01)
*C07D 401/00* (2006.01)

(52) U.S. Cl. .................. 546/196; 546/197; 546/198; 546/199; 546/201; 546/192

(58) Field of Classification Search ............... 546/196, 546/197, 198, 199, 201, 192
See application file for complete search history.

(56) References Cited

U.S. PATENT DOCUMENTS

| | | | |
|---|---|---|---|
| 4,705,853 A | 11/1987 | Cale, Jr. | |
| 6,124,323 A | 9/2000 | Bigge et al. | |

FOREIGN PATENT DOCUMENTS

| | | |
|---|---|---|
| EP | 0 149 088 B1 | 7/1985 |
| EP | 0 160 436 A2 | 11/1985 |
| EP | 0 304 888 B1 | 3/1989 |
| EP | 0 635 505 B1 | 1/1995 |
| WO | WO 97/19059 | 5/1997 |
| WO | WO 99/32117 | 7/1999 |
| WO | WO 01/51469 A1 | 7/2001 |
| WO | WO 01/81303 A1 | 11/2001 |

OTHER PUBLICATIONS

Radl, Arch Pharm Pharm med Chem, vol. 332, pp. 13-18, 1999.*
Stanislav Radl et al.: Synthesis and Analgesic Activity of some Deaza Derivatives of Anpirtolin, *Arch. Pharm. Pharm. Med. Chem.*, 1999, 13-18, 332.
Wang, Hao et al., Synthesis and biological activities of new 5-HT2A selective ligands N-substituted-piperidinyl-4-phenylthioether and sulfone derivatives, *Yaoxue Xuebao*, 2001, 274-277, vol. 36, 4.
Radl, Stanislav et al., Molecular Modification of Anpirtoline, a Non-Opioid Centrally Acting Analgesic, *Collection of Czechoslovak Chem Comm*, 1999, 363-376, vol. 64.

* cited by examiner

*Primary Examiner*—D. Margaret Seaman
(74) *Attorney, Agent, or Firm*—William Kronatin; John C. Todaro

(57) ABSTRACT

Compounds comprising an aza-cyclic portion and an aromatic portion linked via a sulphur atom are disclosed. The compounds disclosed are selective modulators of beta 4 subtype nicotinic acetylcholine receptors and are useful for the treatment of dysfunctions of the central and autonomic nervous systems.

42 Claims, No Drawings

AZA-CYCLIC COMPOUNDS AS MODULATORS OF ACETYLCHOLINE RECEPTORS

This is the national phase application, under 35 USC 371, for PCT/US02/2197, filed 29 Jul. 2002, which claims the benefit, under 35 USC 119(e), of U.S. provisional application No. 60/350,150, filed 17 Jan. 2002.

The present invention relates to compounds that modulate neurotransmission by promoting the release of neurotransmitters such as acetylcholine, dopamine and norepinephrine. More particularly, the present invention relates to thiobridged aryl compounds that are capable of modulating acetylcholine receptors, methods of treatment which utilize such compounds and pharmaceutical compositions comprising such compounds.

Acetylcholine receptors modulate the release of neurotransmitters such as for example dopamine, norepinephrine, acetylcholine, and serotonin from different brain regions. By such action, acetylcholine receptors participate in the modulation of neuroendocrine function, respiration, mood, motor control and function, focus and attention, concentration, memory and cognition, and the mechanisms of substance abuse. Ligands for acetylcholine receptors have been demonstrated to have effects on attention, cognition, appetite, substance abuse, memory, extrapyramidal function, cardiovascular function, pain, and gastrointestinal motility and function. The distribution of acetylcholine receptors that bind nicotine, i.e., nicotinic acetylcholine receptors, is widespread in the brain, including being found in the basal ganglia, limbic system, cerebral cortex and mid- and hind-brain nuclei. In the periphery, their distribution includes being in muscle, autonomic ganglia, the gastrointestinal tract and the cardiovascular system.

Acetylcholine receptors have been shown to be decreased in the brains of patients suffering from Alzheimer's disease or Parkinson's disease, diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. Thus, there is a continuing need for compounds that can modulate the activity of acetylcholine receptors.

Nicotinic acetylcholine receptors (nAChRs) belong to the ligand gated ion channel family of neurotransmitter receptors. In neuronal and peripheral tissue, nAChRs possess a pentameric structure consisting of 5 protein subunits surrounding a central ion channel. Five neuromuscular subunits ($\alpha$, $\beta$, $\gamma$, $\delta$, $\epsilon$), ten peripheral or neuronal $\alpha$-subunits (($\alpha 1$ to $\alpha 10$), and three peripheral or neuronal $\beta$-subunits ($\beta 2$ to $\beta 4$) have been identified. These subunits combine to form pentameric receptors in three ways: first, with homomeric $5[\alpha]$ stoichiometry, for example, $\alpha 7$ to $\alpha 9$; second, with heteromeric $2[\alpha]3[\beta]$ stoichiometry, for example, combinations of $\alpha 1$ to $\alpha 6$ and $\beta 2$ to $\beta 4$ subunits; and third, the $2[\alpha]1[\beta]1[\delta]1[\gamma/\epsilon]$ stoichiometry found in neuromuscular receptors.

Nicotine modulates multiple neuronal, peripheral and neuromuscular subtypes of nAChRs. While demonstrating beneficial effects in a number of neuronal diseases mediated by nAChRs, nicotine also demonstrates a number of undesirable side effects on cardiovascular, gastrointestinal and neuromuscular systems. It will be appreciated that there is a need for compounds that can selectively modulate a single or specific group of nAChRs.

It is desired to provide new compounds which selectively modulate the activity of acetylcholine receptors. In particular, it is desired to provide compounds that are capable of acting as selective modulators, preferably agonists, of beta 4 subtype nicotinic acetylcholine receptors. It is also desirable to provide a method of treatment of dysfunctions of the central and peripheral nervous systems to treat, for example, dementia, cognitive and conduct disorders including attention deficit hyperactivity disorder, neurodegenerative disorders, including Alzheimers disease, Parkinson's disease and other diseases in which degeneration leads to impaired functioning of the sensory or motor systems, extrapyramidal disorders associated with neuroleptic use, convulsive disorders, epilepsy, cardiovascular disorders, endocrine disorders, psychotic disorders including schizophrenia and related disorders, bipolar disease and obsessive-compulsive disorder, eating disorders, sleep-related disorders, affective disorders including depression, anxiety, panic states and stress-related disorders, aggression, emesis, pain and hyperalgesic states of inflammatory and neuropathic origins, sleep and sexual disorders and alcohol and drug abuse or states associated with drug withdrawal including smoking cessation.

WO97/19059 discloses substituted aryl compounds capable of modulating acetylcholine receptors. Specifically, it discloses the compound

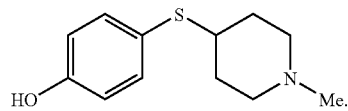

Other compounds disclosed all possess a linker, usually methylene or ethylene, between the S atom and either (or both) of the two ring systems shown above. WO99/32117 discloses similar compounds wherein the aryl moiety is replaced by a 2- or 4-pyridine moiety. It would be desirable to provide alternative compounds to those disclosed in WO97/19059 and WO99/32117. Preferably, such alternatives should exhibit one or more of the following advantages: improved binding to nAChRs, greater modulation of nAChRs, improved selectivity between different nAChRs and improved pharmacokinetic properties (e.g. improved bioavailability).

WO01/51469 discloses potent $5-HT_{2A}$ antagonists and their potential use for treating a number of central nervous system disorders. The compounds disclosed are of the general formula

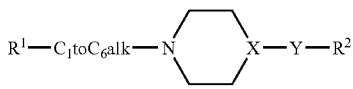

wherein $R^1$ and $R^2$ maybe substituted or unsubstituted phenyl or substituted or unsubstituted unsaturated heterocyclyl, Y maybe S when X is CH. Example 2 discloses a number of substituted 4-(arylsulfanyl)-1-(arylalkyl)-piperidine compounds.

WO01/81303 discloses NMDA-receptor subtype selective blockers and their potential use for treating neurodegenerative disorders. The compounds are pyrollidine and piperidine derivatives of the general formula

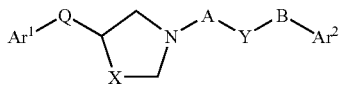

wherein Ar¹ may be pyridyl, phenyl or the group

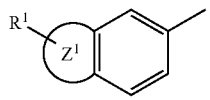

wherein $Z^1$ is a five-membered heterocyclic ring, which contains one or two heteroatoms, selected from N or O and $R^1$ may be H or an oxo group. $Ar^2$ may be pyridyl or phenyl. Q may be S. X may be —$(CH_2)_n$—. A-Y—B taken together may be unsubstituted or substituted alkylene. Intermediates useful for the synthesis of such derivatives are also disclosed.

Anpirtoline (2-chloro-6-(4-piperidinylthio)-pyridine) is discussed in numerous papers which describe its activity as an agonist at $5HT_{1B}$ and $5HT_{1D}$ receptors and as an antagonist at $5HT_3$ receptors. Consequent utility of anpirtoline as an analgesic, anti-agression treatment and as an anti-emetic is also disclosed.

EP-A-0149088 discloses certain substituted 2-(piperidyl-4-thio)-pyridine compounds including anpirtoline and structurally similar analogs thereof.

Radl et al (Archiv der Pharmazie, Weinheim, Germany, 1999, 332(1), 13-18 and Collection of Czechoslovak Chemical Communications 1999, 64(2), 363-376) disclose N-methyl,4-phenylthio-piperidine, derivatives of anpirtoline including 2-methyl,4-chloro-6-(4-pipiredinylthio)-pyridine and 4-(4-pipiredinylthio)-6-chloro-pyridine and some deaza derivatives of anpirtoline including N-methyl,4-[(2-amino,5-chlorophenyl)thio]-piperidine, 4-[(2-chlorophenyl)thio]-piperidine, and N-methyl,4-[(3-chloro,4-aminophenyl)thio]-piperidine.

EP-A-0160436 discloses certain phenyl-thiopiperidine compounds, including 4-phenylthio-piperidine, 3-phenylthio-piperidine and some deaza analogs of anpirtoline including 4-[(3-chlorophenyl)thio]-piperidine, 3-[(3-chlorophenyl)thio]-piperidine, 4-[(2-chlorophenyl)thio]-piperidine, 3-[(2-chlorophenyl)thio]-piperidine and 4-[(2,5-dichlorophenyl)thio]-piperidine as intermediates for the synthesis of compounds which are useful for the treatment or prophylaxis of cardiac arrhythmia.

EP-A-0304888 discloses alkylsulfonyl-aminophenyl-thiopiperidine compounds, including 4-[(4-methylsulfonylaminophenyl)thio]-piperidine, for use as medicaments for the treatment or prophylaxis of arrhythmia.

Wang et al (Yaoxue Xuebao, 2001, 36(4), 274-277) disclose 4-[(2,3-dimethoxyphenyl)thio]-piperidine as an intermediate in the preparation of $5$-$HT_{2A}$ selective ligands EP-A-0635505 discloses 4-[(4-methylsulfonylaminophenyl)thio]-piperidine and 4-[(4-acetamidophenyl)thio]-piperidine as intermediates in the synthesis of oxazolidinone derivatives as nervous system agents.

The present invention provides a method of treatment of a condition indicating treatment with a beta 4 subtype selective nicotinic acetylcholine receptor modulator, preferably an agonist, comprising administering an effective amount of a compound represented by Formula (I) or pharmaceutically acceptable salts thereof:

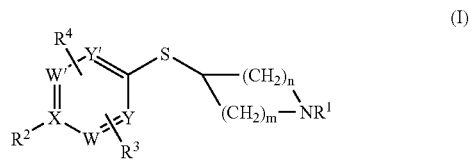

wherein:
$R^1$ is —H,
  $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
$R^2$ is —H,
  —OH,
  —C(O)—NH$_2$,
  —NH$_2$,
  —NH-Q-V-T, wherein Q is —C(O)—, —C(O)—NH—, —C(O)O—, or —SO$_2$—;
    V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)OC$_{1-4}$alkyl, —OC(O)C$_{1-4}$alkyl, aryl-$C_{1-4}$alkoxy, aryloxy, or SO$_2$C$_{1-4}$alkyl; and
    T is H, halogen, $C_{1-5}$alkyl, $C_{1-4}$alkoxy, nitro, aryl, aryl-$C_{1-4}$alkyl, or aryloxy unless V is H in which case T is absent; or
  linked back to the aromatic ring so as to form a fused bicyclic compound represented by Formula (Ia)

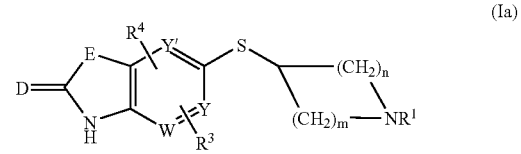

wherein D is O or S; and
  E is O, S, NR$^5$, C(R$^5$)$_2$, O—CR$^5_2$, NR$^5$—CR$^5_2$, NR$^5$—CO, CR$^5_2$—O, CR$^5_2$—S(O)$_r$, CR$^5_2$—NR$^5$, CR$^5_2$—CR$^5_2$, CO—NR$^5$, or CR$^5$=CR$^5$;
unless X is N in which case $R^2$ is absent
$R^3$ is H, halogen, $C_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—, —CO$_2$H, —NH$_2$, NH—C$_{1-4}$alkyl, aryl, hydroxy, —SO$_2$NH$_2$, —SO$_2$NHC$_{1-4}$alkyl, or —C$_{1-4}$alkyl-OH;
$R^4$ is H, halogen, $C_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—, —CO$_2$H, —NH$_2$, NH—C$_{1-4}$alkyl, aryl, hydroxy, —SO$_2$NH$_2$, —SO$_2$NHC$_{1-4}$alkyl, or —C$_{1-4}$alkyl-OH;
$R^5$ is each independently H or $C_{1-4}$alkyl;
X is C or N;
W is C or N;
W' is C or N;
Y is C or N;
Y' is C or N;
provided that there are no more than two N atoms in the aryl ring;

m is 1, 2, or 3;
n is 1, 2, or 3; and
the sum of m and n is 2, 3, 4, 5, or 6;

provided that
when X, W, W', Y and Y' are all C, $R^3$ and $R^4$ are H and $R^1$ is selected from H, unsubstituted $C_{1-4}$alkyl and unsubstituted $C_{3-4}$cycloalkyl, $R^2$ may not be —OH;

and that
when one of X, Y and Y' is N, $R^3$ and $R^4$ are H and $R^1$ is selected from H, unsubstituted $C_{1-4}$alkyl and unsubstituted $C_{3-4}$cycloalkyl, $R^2$ may not be H.

In a further embodiment of the present method, when X, W, W', Y and Y' are all C and $R^3$ and $R^4$ are H, $R^2$ may not be —OH and when one of X, Y and Y' is N and $R^3$ and $R^4$ are H, $R^2$ may not be H.

The present invention also provides a method of treatment of dysfunctions of the central and autonomic nervous systems comprising administering an effective amount of a compound represented by Formula (I) as described above or pharmaceutically acceptable salts thereof;

provided that
when X, W, W', Y and Y' are all C and $R^3$ and $R^4$ are H, $R^2$ may not be —OH;

and that
when one of X, Y and Y' is N and $R^3$ and $R^4$ are H, $R^2$ may not be H;

and that
when $R^2$ is H, OH or $NH_2$ and $R^3$ and $R^4$ are H, $R^1$ may not be aryl-C1-4alkyl.

In a further embodiment of either of the methods disclosed above,
$R^1$ is —H, or
$C_{1-12}$alkyl optionally substituted with 1, 2 or 3 groups independently selected from halogen, hydroxyl, thiol, $C_{1-4}$alkoxy or $C_{1-4}$alkylthio.

In a further embodiment of either of the methods disclosed above,
$R^2$ is —H,
—C(O)—$NH_2$,
—$NH_2$,
—NH-Q-V-T as defined above; or
linked back to the aromatic ring so as to form a fused bicyclic compound represented by Formula (Ia) as defined above;
unless X is N in which case $R^2$ is absent.

In a further embodiment of either of the methods disclosed above,
$R^2$ is —C(O)—$NH_2$,
—NH-Q-V-T as defined above; or
linked back to the aromatic ring so as to form a fused bicyclic compound represented by Formula (Ia) as defined above;
unless X is N in which case $R^2$ is absent.

In a further embodiment of either of the methods disclosed above,
$R^2$ is —C(O)—$NH_2$,
—NH-Q-V-T, wherein Q is —C(O)—NH—, or —C(O)O—;
V is as defined above; and
T is as defined above; or
linked back to the aromatic ring so as to form a fused bicyclic compound represented by Formula (Ia) as defined above;
unless X is N in which case $R^2$ is absent.

Certain compounds falling within the scope of the methods described above are not known for use in therapy. Thus, the present invention provides for a compound of Formula (I) or pharmaceutically acceptable salts thereof for use in therapy:

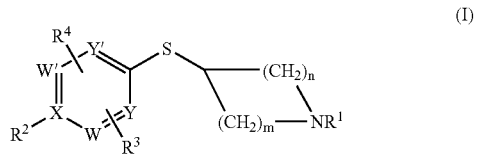

(I)

wherein:
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
$R^2$ is —H,
—OH,
—C(O)—$NH_2$,
—$NH_2$,
—NH-Q-V-T, wherein Q is —C(O)—, —C(O)—NH—, —C(O)O—, or —$SO_2$—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$alkyl; and
T is H, halogen, $C_{1-5}$alkyl, $C_{1-4}$alkoxy, nitro, aryl, aryl-$C_{1-4}$alkyl, or aryloxy unless V is H in which case T is absent; or
linked back to the aromatic ring so as to form a fused bicyclic compound represented by Formula (Ia)

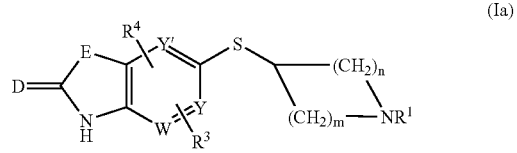

(Ia)

wherein D is O or S; and
E is O, S, $NR^5$, $C(R^5)_2$, O—$CR^5_2$, $NR^5$—$CR^5_2$, $NR^5$—CO, $CR^5_2$—O, $CR^5_2$—S(O)$_r$, $CR^5_2$—$NR^5$, $CR^5_2$—$CR^5_2$, CO—$NR^5$, or $CR^5$=$CR^5$;
unless X is N in which case $R^2$ is absent
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—, —$CO_2$H, —$NH_2$, NH—$C_{1-4}$alkyl, aryl, hydroxy, —$SO_2NH_2$, —$SO_2NHC_{1-4}$alkyl, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—, —$CO_2$H, —$NH_2$, NH—$C_{1-4}$alkyl, aryl, hydroxy, —$SO_2NH_2$, —$SO_2NHC_{1-4}$alkyl, or —$C_{1-4}$alkyl-OH;
$R^5$ is each independently H or $C_{1-4}$alkyl;
X is C or N;
W is C or N;
W' is C or N;
Y is C or N;
Y' is C or N;

provided that there are no more than two N atoms in the aryl ring;
m is 1, 2, or 3;
n is 1, 2, or 3; and
the sum of m and n is 2, 3, 4, 5, or 6;

provided that
when X, W, W', Y and Y' are all C and $R^3$ and $R^4$ are H, $R^2$ may not be —OH;

and that
when one of X, Y and Y' is N and $R^3$ and $R^4$ are H, $R^2$ may not be H;

and that
when $R^2$ is H, OH or $NH_2$ and $R^3$ and $R^4$ are H, $R^1$ may not be aryl-C1-4alkyl;

and excluding compounds represented by Formula I' or pharmaceutically acceptable salts thereof:

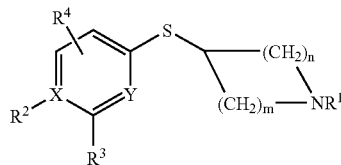

(I')

wherein:
$R^1$, X, Y, m and n are as defined above
$R^2$ is —H,
—$NH_2$,
—NH—$SO_2$-V-T wherein V and T are as defined above;
unless X is N in which case $R^2$ is absent
$R^3$ is H, halogen, $C_{1-4}$alkyl, —$NH_2$, NH—$C_{1-4}$alkyl, or hydroxy;
$R^4$ is H, halogen, $C_{1-4}$alkyl, —$NH_2$, NH—$C_{1-4}$alkyl, or hydroxy.

In a further embodiment of the compounds disclosed above,
$R^1$ is —H, or
$C_{1-12}$alkyl optionally substituted with 1, 2 or 3 groups independently selected from halogen, hydroxyl, thiol, $C_{1-4}$alkoxy or $C_{1-4}$alkylthio.

In a further embodiment of the compounds disclosed above,
$R^2$ is —H,
—C(O)—$NH_2$,
—$NH_2$,
—NH-Q-V-T as defined above; or
linked back to the aromatic ring so as to form a fused bicyclic compound represented by Formula (Ia) as defined above;
unless X is N in which case $R^2$ is absent.

In a further embodiment of the compounds disclosed above,
$R^2$ is —C(O)—$NH_2$,
—NH-Q-V-T as defined above; or
linked back to the aromatic ring so as to form a fused bicyclic compound represented by Formula (Ia) as defined above;
unless X is N in which case $R^2$ is absent.

In a further embodiment of the compounds disclosed above, $R^2$ is —C(O)—$NH_2$,
—NH-Q-V-T, wherein Q is —C(O)—NH—, or —C(O)O—;
V is as defined above; and
T is as defined above; or
linked back to the aromatic ring so as to form a fused bicyclic compound represented by Formula (Ia) as defined above;
unless X is N in which case $R^2$ is absent.

The present invention also provides certain compounds which are novel. Accordingly, the present invention provides compounds represented by formula (I) or pharmaceutically acceptable salts thereof:

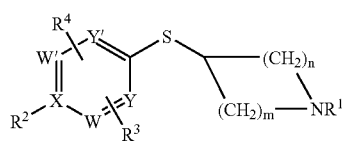

(I)

wherein:
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
$R^2$ is —H,
—OH,
—C(O)—$NH_2$,
—$NH_2$,
—NH-Q-V-T, wherein Q is —C(O)—, —C(O)—NH—, —C(O)O—, or —$SO_2$—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$alkyl; and
T is H, halogen, $C_{1-5}$alkyl, $C_{1-4}$alkoxy, nitro, aryl, aryl-$C_{1-4}$alkyl, or aryloxy unless V is H in which case T is absent; or
linked back to the aromatic ring so as to form a fused bicyclic compound represented by Formula (Ia)

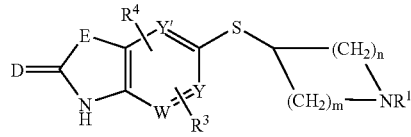

(Ia)

wherein D is O or S; and
E is O, S, $NR^5$, $C(R^5)_2$, O—$CR^5_2$, $NR^5$—$CR^5_2$, $NR^5$—CO, $CR^5_2$—O, $CR^5_2$—S(O)$_r$, $CR^5_2$—$NR^5$, $CR^5_2$—$CR^5_2$, CO—$NR^5$, or $CR^5$=$CR^5$;
unless X is N in which case $R^2$ is absent
$R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—, —$CO_2$H, —$NH_2$, NH—$C_{1-4}$alkyl, aryl, hydroxy, —$SO_2NH_2$, —$SO_2NHC_{1-4}$alkyl, or —$C_{1-4}$alkyl-OH;
$R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—, —CO$_2$H, —NH$_2$, NH—C$_{1-4}$alkyl, aryl, hydroxy, —SO$_2$NH$_2$, —SO$_2$NHC$_{1-4}$alkyl, or —C$_{1-4}$alkyl-OH;

R$^5$ is each independently H or C$_{1-4}$alkyl;

X is C or N;
W is C or N;
W' is C or N;
Y is C or N;
Y' is C or N;
provided that there are no more than two N atoms in the aryl ring;
m is 1, 2, or 3;
n is 1, 2, or 3; and
the sum of m and n is 2, 3, 4, 5, or 6.

provided that
when X, W, W', Y and Y' are all C and R$^3$ and R$^4$ are H, R$^2$ may not be —OH;

and that
when one of X, Y and Y' is N and R$^3$ and R$^4$ are H, R$^2$ may not be H;

and that
when R$^2$ is H, OH or NH$_2$ and R$^3$ and R$^4$ are H, R$^1$ may not be aryl-C$_{1-4}$alkyl;

and excluding compounds represented by Formula I″ or pharmaceutically acceptable salts thereof:

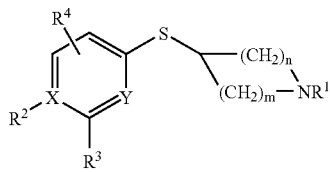

(I″)

wherein:
R$^1$, X, Y, m and n are as defined above
R$^2$ is —H,
  —NH$_2$,
  —NH-Q-V-T, wherein Q is —C(O)— or —SO$_2$— and V and T are as defined above;
  unless X is N in which case R$^2$ is absent
R$^3$ is H, halogen, C$_{1-4}$alkyl, OC$_{1-4}$alkyl, —NH$_2$, NH—C$_{1-4}$alkyl, or hydroxy;
R$^4$ is H, halogen, C$_{1-4}$alkyl, OC$_{1-4}$alkyl, CO$_2$H, —NH$_2$, NH—C$_{1-4}$alkyl, or hydroxy.

In a further embodiment of the novel compounds disclosed above,
R$^1$ is —H, or
  C$_{1-12}$alkyl optionally substituted with 1, 2 or 3 groups independently selected from halogen, hydroxyl, thiol, C$_{1-4}$alkoxy or C$_{1-4}$alkylthio.

In a further embodiment of the novel compounds disclosed above,
R$^2$ is —H,
  —C(O)—NH$_2$,
  —NH$_2$,
  —NH-Q-V-T as defined above; or
  linked back to the aromatic ring so as to form a fused bicyclic compound represented by Formula (Ia) as defined above;
  unless X is N in which case R$^2$ is absent.

In a further embodiment of the novel compounds disclosed above,
R$^2$ is —C(O)—NH$_2$,
  —NH-Q-V-T as defined above; or
  linked back to the aromatic ring so as to form a fused bicyclic compound represented by Formula (Ia) as defined above;
  unless X is N in which case R$^2$ is absent.

In a further embodiment of the novel compounds disclosed above,
R$^2$ is —C(O)—NH$_2$,
  —NH-Q-V-T, wherein Q is —C(O)—NH—, or —C(O)O—;
  V is as defined above; and
  T is as defined above; or
  linked back to the aromatic ring so as to form a fused bicyclic compound represented by Formula (Ia) as defined above;
  unless X is N in which case R$^2$ is absent.

In one embodiment, the present invention provides a subgroup of compounds (Group A) represented by formula (II) or pharmaceutically acceptable salts thereof:

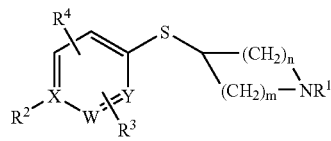

(II)

wherein:
R$^1$ is —H, or
  C$_{1-12}$alkyl optionally substituted with 1, 2 or 3 groups independently selected from halogen, hydroxyl, thiol, C$_{1-4}$alkoxy or C$_{1-4}$alkylthio, or aryl-C$_{1-4}$alkyl;
R$^2$ is —H,
  —OH,
  —C(O)—NH$_2$,
  —NH$_2$,
  —NH-Q-V-T, wherein Q is —C(O)—, —C(O)—NH—, —C(O)O—, or —SO$_2$—;
  V is aryl, aryl-C$_{1-12}$alkyl, diaryl-C$_{1-12}$alkyl, lactonyl, or C$_{1-18}$alkyl optionally substituted with halogen, hydroxyl, C$_{1-4}$alkoxy, —C(O)OC$_{1-4}$alkyl, —OC(O)C$_{1-4}$alkyl, aryl-C$_{1-4}$alkoxy, aryloxy, or SO$_2$C$_{1-4}$alkyl; and
  T is H, halogen, aryl, aryl-C$_{1-4}$alkyl, or aryloxy;

unless X is N in which case R$^2$ is absent
R$^3$ and R$^4$ are each independently selected from H, halogen, C$_{1-4}$alkyl, cyano, CF$_3$, OC$_{1-4}$alkyl, aryloxy, arylC$_{1-4}$alkoxy, C$_{3-10}$cycloalkoxy, carboxy, carbonamido, —CO—, —CO$_2$H, —NH$_2$, NH—C$_{1-4}$alkyl, aryl, hydroxy, —SO$_2$NH$_2$, —SO$_2$NHC$_{1-4}$alkyl, or —C$_{1-4}$alkyl-OH;
X is C or N;
W is C or N; provided that both X and Y are not N;
Y is C or N;
m is 1, 2, or 3;
n is 1, 2, or 3; and
the sum of m and n is 2, 3, 4, 5, or 6

Within Group A, R$^1$ is preferably —H; or C$_{1-12}$alkyl optionally substituted with 1, 2 or 3 groups independently selected from hydroxyl, thiol, C$_{1-4}$alkoxy or C$_{1-4}$alkylthio; or aryl-C$_{1-4}$alkyl.

Within Group A, R$^1$ is more preferably H; C$_{1-6}$ alkyl optionally substituted with 1 or 2 hydroxyl groups; or aryl- $C_{1-4}$ alkyl. When $R^1$ is an aryl-$C_{1-4}$ alkyl group, examples of suitable groups are benzyl, p-methoxybenzyl, furanylmethyl, imidazolylmethyl, pyridinylmethyl, thienylmethyl, pyridylmethyl, N-hydroxypyridylmethyl or thiazolylmethyl.

Within Group A, $R^1$ is more preferably H, methyl, cyclopropylmethyl, 2-hydroxyethyl or isobutyl. When $R^1$ is one of these groups, greater potency is generally observed. More preferably, $R^1$ is a methyl group.

In one embodiment of Group A, $R^2$ is H. When $R^2$ is H, $R^3$ is preferably carbonamido (—$CONH_2$) or —$C_{1-4}$alkyl-OH and $R^4$ is H, $C_{1-4}$alkyl, $CF_3$, halogen or cyano (more preferably H, halogen or cyano). More preferably $R^3$ is carbonamido (—$CONH_2$) or —$C_{1-4}$alkyl-OH and $R^4$ is methyl, $CF_3$, Cl or cyano (more preferably Cl or cyano).

In another embodiment of Group A, $R^2$ is OH. When $R^2$ is OH, $R^3$ and $R^4$ are preferably H, $C_{1-4}$alkyl, $CF_3$, cyano or halogen (more preferably H, cyano or halogen). More preferably $R^3$ is methyl, $CF_3$, Cl or cyano (more preferably Cl or cyano) attached to position Y when Y is C.

Generally, within Group A, when $R^2$ is of formula —NH-Q-V-T, T is preferably H and $R^3$ and $R^4$ are preferably H, methyl, $CF_3$, chloro- or cyano (more preferably H, chloro- or cyano).

In another embodiment of Group A, $R^2$ is of the formula —NH—$SO_2$-V-T, wherein V is aryl, —$C_{1-12}$alkyl or aryl-$C_{1-12}$alkyl. In this embodiment of the present invention $R^3$ is preferably H, methyl, $CF_3$, Cl or cyano (more preferably H, Cl or cyano) and $R^4$ is preferably H.

Within Group A, when $R^2$ is of formula —NH—$SO_2$-V-T, preferably V is selected from $C_{1-12}$ alkyl, phenyl, naphthyl, thienyl, oxazolyl, isoxazolyl, or phenyl (CH=CH)—, optionally substituted with 1, 2, 3 or 4 substituents selected from:
  —$NO_2$;
  halogen;
  —$CF_3$;
  $C_{1-12}$ alkoxy;
  $C_{1-12}$ alkylthio;
  $C_{1-12}$ alkyl;
  $C_{1-4}$ alkylsulfonyl;
  —CN;
  —$OCF_3$;
  —C(O)O$C_{1-4}$ alkyl;
  —$OCH_2CF_3$;
  —NHC(O)$C_{1-4}$ alkyl.

Within Group A, when $R^2$ is of formula —NH—$SO_2$-V-T, preferably T is selected from H, or diazole, oxazole, isoxazole, phenyl or phenoxy, optionally substituted with 1, 2, 3 or 4 substituents selected from
  —$NO_2$;
  halogen;
  —$CF_3$;
  $C_{1-12}$ alkoxy;
  $C_{1-12}$ alkylthio;
  $C_{1-12}$ alkyl;
  $C_{1-4}$ alkylsulfonyl;
  —CN;
  —$OCF_3$;
  —C(O)O$C_{1-4}$ alkyl;
  —$OCH_2CF_3$;
  —NHC(O)$C_{1-4}$ alkyl.

Within Group A, when $R^2$ is of formula —NH—$SO_2$-V-T, V is more preferably selected from 3-chloro-4-methylphenyl, 3-chlorophenyl, 3-methoxyphenyl, 4-bromophenyl, 4-methoxyphenyl, 4-methylphenyl, naphthyl, 2,4,6-trimethylphenyl, phenyl(CH=CH)—, 4-chlorophenyl, 2-chlorophenyl, 2,5-dichlorothien-3-yl, 2,5,6-trimethyl-4-methoxyphenyl, 4-methoxyphenyl, 2,3,4-trifluorophenyl, 3-cyanophenyl, 2-methoxycarbonylthien-3-yl or 4-pentylphenyl (even more preferably selected from 4-bromophenyl, 4-methoxyphenyl, 4-methylphenyl, naphthyl, 2,4,6-trimethylphenyl, phenyl (CH=CH)—, 4-chlorophenyl, 2-chlorophenyl, 2,5-dichlorothien-3-yl, 2,5,6-trimethyl-4-methoxyphenyl, 4-methoxyphenyl, 2,3,4-trifluorophenyl, 3-cyanophenyl, 2-methoxycarbonylthien-3-yl or 4-pentylphenyl) and T is preferably H.

In a further embodiment within Group A, when $R^2$ is of formula —NH—$SO_2$-V-T, T is preferably 2-chloro-5-nitrophenoxy and V is preferably phenyl.

In an alternative embodiment of Group A, $R^2$ is of formula —NH—C(O)-V-T wherein V is selected from
  aryl;
  aryl-$C_{1-12}$alkyl;
  diaryl-$C_{1-12}$alkyl;
  lactonyl; or
  $C_{1-18}$alkyl optionally substituted with halogen, hydroxyl, $C_{1-4}$alkoxy, C(O)O$C_{1-4}$alkyl, OC(O)$C_{1-4}$alkyl, aryl-$C_{1-4}$alkoxy, aryloxy. In this embodiment of the present invention, $R^3$ is preferably H, methyl, $CF_3$, Cl or cyano (more preferably H, Cl or cyano) and $R^4$ is H.

When $R^2$ is of formula —NH—C(O)-V-T, preferably V is selected from $C_{1-12}$ alkyl, phenyl, phenyl-$C_{1-12}$ alkyl, diphenylmethyl, naphthyl, furanyl, thienyl, diazolyl, pyridinyl, thiazolyl, benzothienyl, fluorenyl, oxazolyl or isoxazolyl, optionally substituted with 1, 2, 3 or 4 substituents independently selected from
  —$NO_2$;
  halogen;
  —$CF_3$;
  $C_{1-12}$ alkoxy;
  $C_{1-12}$ alkylthio;
  $C_{1-12}$ alkyl;
  $C_{1-4}$ alkylsulfonyl;
  —CN;
  —$OCF_3$;
  —C(O)O—$C_{1-4}$ alkyl;
  —$OCH_2CF_3$.
More preferably V is $C_{1-12}$ alkyl.

When $R^2$ is of formula —NH—C(O)-V-T, preferably T is selected from
  H;
  halogen; or
  diazole, oxazole, isoxazole, phenyl, phenoxy or benzodioxanyl optionally substituted with 1, 2, 3 or 4 substituents selected from
    —$NO_2$;
    halogen;
    —$CF_3$;
    $C_{1-12}$ alkylthio;
    $C_{1-12}$ alkoxy;
    $C_{1-12}$ alkyl;
    $C_{1-4}$ alkylsulfonyl;
    —CN;
    —$OCF_3$;
    —C(O)O—$C_{1-4}$ alkyl.
More preferably T is H.

In an alternative embodiment of the present invention, $R^2$ is of formula —NH—C(O)N-V-T wherein V is selected from
  $C_{1-18}$ alkyl optionally substituted with halogen, hydroxyl, $C_{1-4}$ alkoxy, C(O)O$C_{1-4}$ alkyl, OC(O)$C_{1-4}$ alkyl, aryl-$C_{1-4}$ alkoxy, aryloxy;
  aryl; or
  aryl-$C_{1-12}$ alkyl.

When $R^2$ is of formula —NH—C(O)NH-V-T, preferably V is selected from phenyl, phenyl-$C_{1-12}$ alkyl or naphthyl optionally substituted with 1, 2, 3 or 4 substituents selected from
- —$NO_2$;
- halogen;
- —$CF_3$;
- $C_{1-12}$ alkylthio;
- $C_{1-12}$ alkoxy;
- $C_{1-12}$ alkyl;
- $C_{1-4}$ alkylsulfonyl;
- —CN;
- —$OCF_3$;
- —C(O)O—$C_{1-4}$ alkyl.

When $R^2$ is of formula —NH—C(O)NH-V-T, preferably T is H.

In an alternative embodiment of the present invention, $R^2$ is of formula —NH—C(O)O-V-T, wherein V is selected from
- $C_{1-18}$ alkyl optionally substituted with halogen, hydroxyl, $C_{1-4}$ alkoxy, C(O)O$C_{1-4}$ alkyl, OC(O)$C_{1-4}$ alkyl, aryl-$C_{1-4}$ alkoxy, aryloxy;
- aryl; or
- aryl-$C_{1-12}$ alkyl.

When $R^2$ is of formula —NH—C(O)O-V-T, preferably V is selected from phenyl or phenyl-$C_{1-12}$ alkyl optionally substituted with 1, 2, 3 or 4 substituents selected from
- —$NO_2$;
- halogen;
- —$CF_3$;
- $C_{1-12}$ alkylthio,
- $C_{1-12}$ alkoxy;
- $C_{1-12}$ alkyl;
- $C_{1-4}$ alkylsulfonyl;
- —CN;
- —$OCF_3$;
- —C(O)O—$C_{1-4}$ alkyl; or
- —$OCH_2CF_3$.

When $R^2$ is of formula —NH—C(O)O-V-T, preferably T is H.

In another embodiment, the present invention provides a further sub-group of compounds (Group B) represented by formula (I) or pharmaceutically acceptable salts thereof:
wherein $R^2$ is of formula —NH—C(O)-V-T
wherein V is H, $C_{1-6}$alkyl, $C_{3-6}$cycloalkyl, aryl or aryl-$C_{1-12}$alkyl; and
T is H, halogen, $C_{1-5}$alkyl, $C_{1-4}$alkoxy, nitro, aryl, aryl-$C_{1-4}$alkyl, or aryloxy unless V is H in which case T is absent.

In a preferred embodiment within Group B, when V is H, $C_{1-6}$alkyl or $C_{3-6}$cycloalkyl, preferably T is H unless V is H in which case T is absent.

In another preferred embodiment within Group B, when V is aryl or aryl-$C_{1-12}$alkyl, preferably T is H, halogen, $C_{1-5}$alkyl, $C_{1-4}$alkoxy, nitro, aryl, aryl-$C_{1-4}$alkyl, or aryloxy. More preferably, V is phenyl, pyridyl, thienyl, thiazolyl, thiadiazolyl, or phenyl-$C_{1-6}$alkyl; and T is H, halogen, $C_{1-5}$alkyl, $C_{1-4}$alkoxy, nitro, aryl, aryl-$C_{1-4}$alkyl, or aryloxy.

In another embodiment, the present invention provides a further sub-group of compounds (Group C) represented by formula (I) or pharmaceutically acceptable salts thereof:
wherein
$R^1$ is —H,
$C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;

$R^2$ is —$NH_2$, or
—NH-Q-V-T, wherein Q is —C(O)—, —C(O)—NH—, —C(O)O—, or —$SO_2$—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$ alkyl; and
T is H, halogen, aryl, aryl-$C_{1-4}$alkyl, or aryloxy unless V is H in which case T is absent, $R^3$ is H, halogen, $C_{1-4}$alkyl optionally substituted with from 1 to 3 fluorine atoms, cyano, $CF_3$, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

$R^4$ is H, halogen, $C_{1-4}$alkyl optionally substituted with from 1 to 3 fluorine atoms, cyano, $CF_3$, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;

X is C;
W is C or N;
W' is C or N;
Y is C or N;
Y' is C or N;
provided that there are not more than two N atoms in the aryl ring and provided that at least one of W, W', Y or Y' is N;
m is 1, 2, or 3;
n is 1, 2, or 3; and
the sum of m and n is 2, 3, 4, 5, or 6; and
r is 0, 1 or 2.

In a preferred embodiment of the compounds of Group C only one of W, W', Y and Y' is N.

In one embodiment of the compounds of Group C
W is C;
W' is C;
Y' is C; and
Y is N.

In another embodiment of the compounds of Group C
W is N;
W' is C;
Y' is C; and
Y is C.

In another embodiment of the compounds of Group C, $R^2$ is —$NH_2$.

In another embodiment of the compounds of Group C
$R^2$ is —NH-Q-V-T, wherein Q is —C(O)—, —C(O)—NH—, —C(O)O—, or —$SO_2$—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$alkyl; and
T is H, halogen, aryl, aryl-$C_{1-4}$alkyl, or aryloxy unless V is H in which case T is absent.

Within Group C, when $R^2$ is —NH-Q-V-T, preferably Q is —$SO_2$— or —CO—.

In another embodiment, the present invention provides a further sub-group of compounds (Group $F^1$) represented by formula (I) or pharmaceutically acceptable salts thereof:

wherein:
R¹ is —H,
C$_{1-12}$alkyl optionally substituted with 1, 2 or 3 groups independently selected from halogen, hydroxyl, thiol, C$_{1-4}$alkoxy or C$_{1-4}$alkylthio, or aryl-C$_{1-4}$alkyl;
R² is linked back to the aromatic ring so as to form a fused bicyclic compound represented by Formula (Ia)

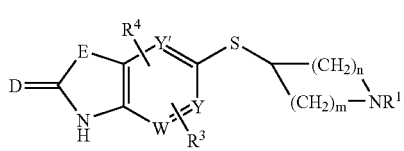

(Ia)

wherein D is O or S; and
E is O, S, NR⁵, or C(R⁵)$_2$,
R³ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁴ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁵ is each independently H or C$_{1-4}$alkyl;
X is C;
W is C or N;
W' is C;
Y is C or N;
Y' is C or N;
provided that there are no more than two N atoms in the aryl ring,
m is 1, 2, or 3;
n is 1, 2, or 3; and
the sum of m and n is 2, 3, 4, 5, or 6.
In one preferred embodiment of sub-group F¹, E is O or NR⁵.
In another preferred embodiment of sub-group F¹, R⁵ is/are each independently H or C$_{1-4}$alkyl.
In another embodiment, the present invention provides a further sub-group of compounds (Group F²) represented by formula (I) or pharmaceutically acceptable salts thereof:
wherein:
R¹ is —H,
C$_{1-12}$alkyl optionally substituted with 1, 2 or 3 groups independently selected from halogen, hydroxyl, thiol, C$_{1-4}$alkoxy or C$_{1-4}$alkylthio, or aryl-C$_{1-4}$alkyl;
R² is linked back to the aromatic ring so as to form a fused bicyclic compound represented by Formula (Ia)

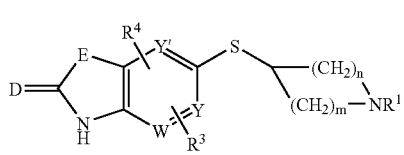

(Ia)

wherein D is O or S; and
E is O—CR⁵$_2$, NR⁵—CR⁵$_2$, NR⁵—CO, CR⁵$_2$—O, CR⁵$_2$—S(O)$_r$, CR⁵$_2$—NR⁵, CR⁵$_2$—CR⁵$_2$, CO—NR⁵, or CR⁵=CR⁵;
R³ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁴ is H, halogen, C$_{1-4}$alkyl optionally substituted with from 1 to 3 fluorine atoms, cyano, CF$_3$, OC$_{1-4}$alkyl, aryloxy, arylC$_{1-4}$alkyl, arylC$_{1-4}$alkoxy, C$_{3-10}$cycloalkoxy, carboxy, carbonamido, —CO—NH—C$_{1-4}$alkyl, aryl, hydroxy, —SO$_2$NH$_2$, —SO$_2$NHC$_{1-4}$alkyl, or —C$_{1-4}$alkyl-OH;
R⁵ is each independently H, C$_{1-4}$alkyl;
X is C;
W is C or N;
W' is C;
Y is C or N;
Y' is C or N;
provided that there are no more than two N atoms in the aryl ring;
m is 1, 2, or 3;
n is 1, 2, or 3; and
the sum of m and n is 2, 3, 4, 5, or 6.
In one preferred embodiment of sub-group F², E is O—CR⁵$_2$, NR⁵—CR⁵$_2$, NR⁵—CO, CR⁵$_2$—CR⁵$_2$, or CR⁵=CR⁵. More preferably, E is O—CR⁵$_2$, NR⁵—CO, or CR⁵=CR⁵.
In another preferred embodiment of sub-group F², R⁵ is/are each independently H or C$_{1-4}$alkyl.
Within Group A, m is preferably 2 and n is 1, 2 or 3. More preferably, m is 2 and n is 3.
Within Group A, X, Y and W are preferably C.
For all embodiments of the present invention, R¹ is preferably H or C$_{1-3}$alkyl, more preferably methyl.
For all embodiments of the present invention, the sum of m, n, o and p is preferably 4. More preferably, m and n are 2.
For all embodiments of the present invention it is preferred that m and n are 2 and R¹ is H or C$_{1-3}$alkyl.
For all embodiments of the present invention, R³ is preferably H, halogen, C$_{1-4}$alkyl, cyano, CF$_3$, or OC$_{1-4}$alkyl, and R⁴ is preferably H, halogen, C$_{1-4}$alkyl, cyano, CF$_3$, or OC$_{1-4}$alkyl.
For all embodiments of the present invention, one or both of R³ and R⁴ is/are not H and is/are preferably positioned ortho to the S linker moeity.
For all embodiments of the present invention, one or both of R³ and R⁴ is/are halogen, C$_{1-4}$alkyl, cyano, CF$_3$, or OC$_{1-4}$alkyl, more preferably halogen, cyano, or C$_{1-4}$alkyl, most preferably halogen, positioned ortho to the S linker moeity.
As used herein, the term "alkyl" means a branched or unbranched, cyclic and/or acyclic, saturated or unsaturated (e.g. alkenyl or alkynyl), monovalent or divalent hydrocarbyl radical. Examples of branched alkyl groups are isopropyl, isobutyl, tert-butyl etc. Examples of cyclic alkyl groups are cyclopropyl, cyclobutyl, cyclopentyl, cycohexyl, adamantyl etc. Examples of groups containing both cyclic and acyclic alkyl moieties are cyclopropylmethyl, cyclohexylpropyl, adamantylethyl etc.
As used herein, the term "aryl" means a C$_3$ to C$_{26}$, preferably C$_3$ to C$_{12}$ aromatic or heteroaromatic group which may, optionally, be substituted with one or more substituents. Aryl substituents are preferably selected from C$_1$ to C$_{12}$ alkyl (preferably C$_1$ to C$_6$ alkyl), C$_1$ to C$_{12}$ alkoxy (preferably C$_1$ to $C_6$ alkoxy), thio, $C_1$ to $C_{12}$ alkylthio (preferably $C_1$ to $C_6$ alkylthio), carboxy, carboxy($C_1$ to $C_6$)alkyl, formyl, $C_1$ to $C_6$ alkylcarbonyl, $C_1$ to $C_6$ alkylsulfonyl, $C_1$ to $C_6$ alkylcarbonylalkoxy, nitro, trihalomethyl, trihalo($C_1$ to $C_6$ alkoxy), trihalomethoxy, trihalomethyl($C_1$ to $C_6$ alkyl), hydroxy, hydroxy ($C_1$ to $C_6$)alkyl, ($C_1$ to $C_6$ alkoxy)carbonyl, amino, $C_1$ to $C_6$ alkylamino, di($C_1$ to $C_6$ alkyl)amino, aminocarboxy, $C_1$ to $C_6$ alkylaminocarboxy, di($C_1$ to $C_6$ alkyl)aminocarboxy, aminocarboxy($C_1$ to $C_6$)alkyl, $C_1$ to $C_6$ alkylaminocarboxy($C_1$ to $C_6$)alkyl, di($C_1$ to $C_6$ alkyl)aminocarboxy($C_1$ to $C_6$)alkyl, $C_1$ to $C_6$ alkylcarbonylamino, $C_1$ to $C_6$ alkylcarbonyl($C_1$ to $C_6$ alkyl)amino, halo, $C_1$ to $C_6$ alkylhalo, sulphamoyl, tetrazolyl and cyano.

Examples of aromatic groups are phenyl, naphthyl, fluorenyl, thienyl, furanyl, pyrrolyl, imidazolyl, pyrazolyl, thiazolyl, isothiazolyl, oxazolyl, isoxazolyl, oxadiazolyl, thiadiazolyl, diazolyl, triazolyl, tetrazolyl, benzothiazolyl, benzimidazolyl, pyrrolinyl, imidazolinyl, pyranyl, pyronyl, pyridyl, pyrazinyl, pyridazinyl, thianaphthyl, benzofuranyl, isobenzofuranyl, benzothienyl, isobenzothienyl, indolyl, oxyindolyl, isoindolyl, indazolyl, indolinyl, 7-azaindolyl, azabenzimidazolyl, carbazolyl benzopyranyl, coumarinyl, isocoumarinyl, quinolinyl, isoquinolinyl, quinazolinyl, benzoxazinyl, quinoxalinyl, chromenyl, chromanyl, isochromanyl, phthalazinyl, benzodioxolyl, benzodioxanyl, cinnolinyl and carbolinyl.

Terms such as "aryl-$C_{1-12}$ alkyl group" include groups such as benzyl, 4-chlorobenzyl, phenylpropyl, thienylethyl etc. Further, the alkyl moiety in, for example, aryl-$C_{1-12}$ alkyl groups may optionally be substituted with 1, 2 or 3 substituents selected from halogen, hydroxyl, $C_{1-4}$ alkoxy or $C_{1-4}$ alkylthio.

As used herein the term "lactonyl" means any $C_{1-18}$ cyclic ester. The lactonyl group may be monocyclic or polycyclic.

As used herein, the terms "halogen" or "halo" refer to any one of F, Cl, Br or I.

Compounds of Group A wherein
$R^2$=OH; and
$R^3$=methyl, $CF_3$, halogen or H;

may be prepared by a procedure exemplified in Reaction Scheme 1.

While Reaction Scheme 1 exemplifies compounds of the present invention wherein m=n=2, it will be readily apparent to the skilled person that the same procedures may be applied to other ring sizes (i.e. when the sum of m and n is 2, 3, 5 or 6).

Reaction Scheme 1

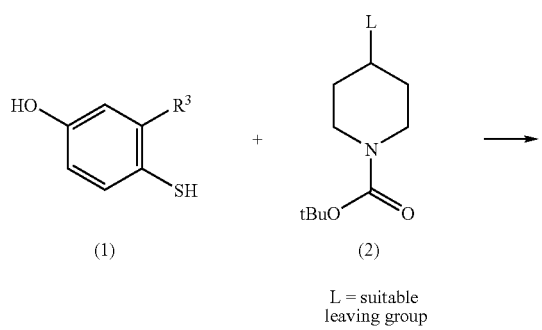

(1)        (2)

L = suitable leaving group

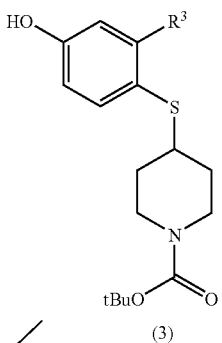

(3)

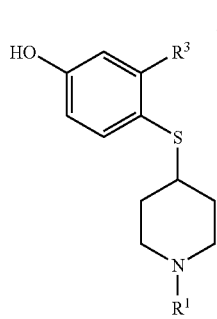

(4)

Thiophenol (1) [commercial or prepared according to Kita Y.; Takeda, Y.; Okuno, T.; Egi, M.; Ito, K.; Kawaguchi, K; Akai, S. *Chem. Pharm. Bull.* 1997, 45(12), 1887-1890 or Zheng, J.; Hanzlik, R. P. *Drug Metab. Dispos.* 1992, 20(5), 688-694], is coupled with carbamate (2) by displacement of the leaving group L. Suitable leaving groups will be readily apparent to the person skilled in the art. Typical leaving groups include iodo, chloro, bromo, mesyl or tosyl. The coupling reaction is preferably performed in a dipolar solvent such as methanol, THF or DMF. More preferably, the coupling reaction is performed in a 50/50 mixture of THF and DMF. The coupling reaction is preferably promoted by a suitable base such as potassium hydroxide, sodium hydride, sodium ethoxide, potassium carbonate or DBU. More preferably, the coupling reaction is performed in the presence of potassium carbonate or sodium hydride. Typically the coupling reaction may be carried out over a temperature range of from −78 to 150° C. Preferably, the reaction is carried out at a temperature in the range of from room temperature to 70° C. Reaction times for the coupling reaction are typically from 10 minutes to 24 hours. Preferred reaction times are in the range of 30 minutes to 12 hours.

Thioether (3) is subsequently converted into compounds of the present invention corresponding to the thioether of formula (4). When $R^1$ is methyl, compounds of formula (4) may be prepared by reduction using, for example, litlhiiun aluminium hydride. When $R^1$ is other than methyl, compounds of formula (4) may be prepared by deprotection of the carbamate group (usually under acidic conditions) followed by reaction with a suitable aldehyde or allyl halide.

Reduction with lithium aluminium hydride is typically carried out in ether or THF (preferably THF). Preferably, the reduction is carried out at room temperature. Reaction times vary from 10 minutes to up to several days. Preferred reaction times are in the range of 12 to 48 hours.

Alternatively, when $R^1$ is other than methyl, the carbamate derivative (3) is deprotected under standard conditions. Typical carbamate deprotection conditions involve using either protic acids (e.g. trifluoroacetic acid, HCl, HBr) or Lewis acids (e.g. acid chlorides/bromides, tri(m)ethylsilyl triflate). The solvent used is typically water, dichloromethane, dioxane, THF or ether. Preferably, an acid chloride in dioxane is used when the protecting group is tert-butyl carbamate (Boc). Preferably, HBr in water is used when the protecting group is ethyl carbamate. Preferably, deprotection is carried out at room temperature (in the case of Boc-deprotection) or at reflux (in the case of ethyl carbamate).

Once a free amine has been realised following deprotection, procedures for introducing various $R^1$ groups (wherein $R^1$ is optionally substituted $C_{1-12}$ alkyl or aryl-$C_{1-4}$alkyl) will be readily apparent to the skilled person. Generally, displacement of an alkyl halide (or reductive alkylation with an aldehyde) furnishes the desired tertiary amine (4).

Compounds of Group A wherein:
$R^1$=methyl;
$R^2$=—NH$_2$ or —NH-Q-V-T; and
$R^3$=H May be prepared by a procedure exemplified in Reaction Scheme 2.

While Reaction Scheme 2 exemplifies compounds of the present invention wherein m=n=2, it will be readily apparent to the skilled person that the same procedures may be applied to other ring sizes (i.e. when the sum of m and n is 2, 3, 5 or 6).

Reaction Scheme 2

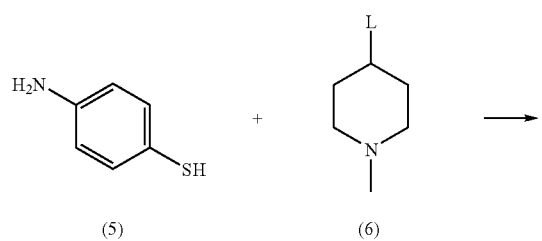

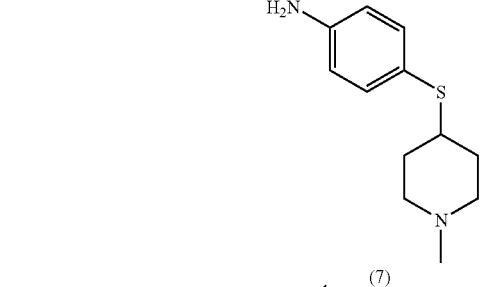

Commercially available 4-aminothiophenol (5) is coupled with amine (6) by displacement of a suitable leaving group L, as outlined above in Reaction Scheme 1. The resultant thioether bridged compound (7) is a key intermediate in the synthesis of compounds of the present invention. It will be readily apparent to the person skilled in the all that various $R^2$ groups of general type —NH-Q-V-T may be prepared from compound (7) by standard procedures known in the art. For example, when:

(a) Q is —SO$_2$—, by coupling with a compound of general formula T-V-SO$_2$-L';

(b) Q is —CO—, by coupling with a compound of general formula T-V-CO-L';

(c) Q is —NH—C(O)—, by coupling with a compound of general formula T-V-N=C=O;

(d) Q is —OC(O)—, by coupling with a compound of general formula T-V-OC(O)-L' wherein L' is any suitable leaving group, such as Cl, Br or I.

Typically, the coupling reaction which affords compounds of formula (8) is performed in pyridine or an aprotic solvent such as dichloromethane in the presence of a base such as pyridine, triethylamine or diisopropylamine. Preferably, the coupling is performed at room temperature with reaction times varying from 10 minutes to 24 hours, preferably 30 minutes to 12 hours.

Compounds of Group B wherein V is H may be prepared by a procedure exemplified in Reaction Scheme 3.

While Reaction Scheme 3 exemplifies compounds of the present invention wherein m=n=2, it will be readily apparent to the skilled person that the same procedures may be applied to other ring sizes (i.e. when the sum of m and n is 2, 3, 5 or 6).

Reaction Scheme 3

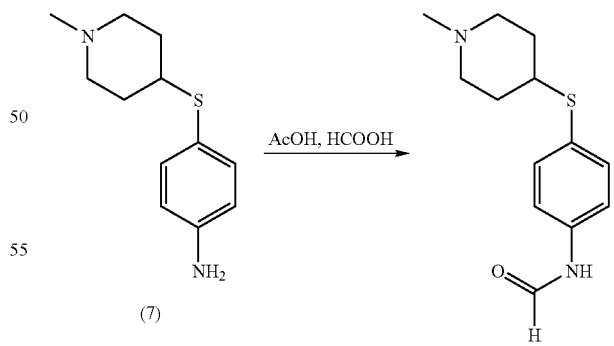

A mixture of acetic acid and formic acid is heated under reflux for about 2 hours. To this is added the thioether bridged compound (7) (prepared according to Scheme 2 above) and heating continues for about 1.5 hours. The crude mixture may be purified by elution on an SCX cartridge followed by flash chromatography.

Compounds of Group B wherein V is $C_{1-6}$alkyl, $C_{3-6}$cycloalkyl, aryl or aryl-$C_{1-12}$alkyl may be prepared by a procedure exemplified in Reaction Scheme 4.

While Reaction Scheme 4 exemplifies compounds of the present invention wherein m=n=2, it will be readily apparent to the skilled person that the same procedures may be applied to other ring sizes (i.e. when the sum of m and n is 2, 3, 5 or 6).

Reaction Scheme 4

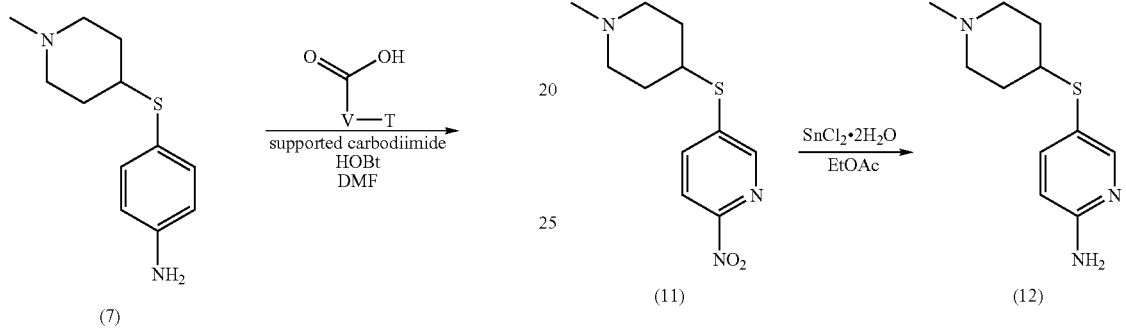

A mixture of the thioether bridged compound (7) (prepared according to Scheme 2 above), T-V-$CO_2$H, 1-hydroxybenzotriazole and carbodiimide resin in DMF is stirred at room temperature for about 3 days. The mixture is filtered then passed through an SCX cartridge to provide the product (9).

Compounds of Group C wherein $R^2$ is $NH_2$ may be prepared by a procedure exemplified in Reaction Scheme 5.

While Reaction Scheme 5 exemplifies compounds of the present invention wherein m=n=2, and W is N, it will be readily apparent to the skilled person that the same procedures may be applied to other ring sizes (i.e. when the sum of m and n is 2, 3, 5 or 6) or where Y is N.

Reaction Scheme 5

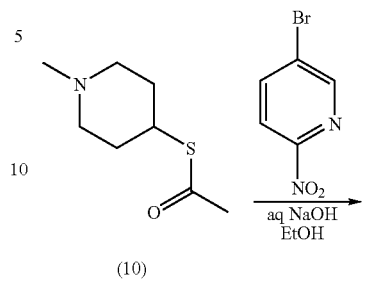

Step 1:

A mixture of the ethanethioate (10) and 2-nitro-5-bromopyridine in ethanol and aqueous sodium hydroxide is stirred at room temperature for about 18 hours. The mixture is applied directly to an SCX cartridge and eluted to yield the crude product which may be purified by preparative LC-MS to provide the nitro-pyridinyl-thio-azacyclo compound (11).

Step 2:

A mixture of the nitro-pyridinyl-thio-azacyclo compound (11) and tin (II) chloride dihydrate in ethyl acetate is heated under reflux for about 4 days and then worked up by quenching with aqueous sodium hydrogen carbonate solution to provide the aminopyridine product (12). Step 2 may also be achieved by Pd/C catalysed $H_2$ reduction It will be readily apparent to the person skilled in the art that compounds of Group C wherein $R^2$ is —NH-Q-V-T may be prepared from compound (12) by standard procedures known in the art. For example, when:

(e) Q is —$SO_2$—, by coupling with a compound of general formula T-V-$SO_2$-L';

(f) Q is —CO—, by coupling with a compound of general formula T-V-CO-L';

(g) Q is —NH—C(O)—, by coupling with a compound of general formula T-V-N═C═O;

(h) Q is —OC(O)—, by coupling with a compound of general formula T-V-OC(O)-L' wherein L' is any suitable leaving group, such as Cl, Br, or I.

Compounds of Group $F^1$ and $F^2$ may be prepared by procedures exemplified in Reaction Schemes 6 to 9. While the Schemes exemplify compounds of the present invention wherein m=n=2, it will be readily apparent to the skilled person that the same procedures may be applied to other ring sizes (i.e. when the sum of m and n is 2, 3, 5 or 6).

Reaction Scheme 6

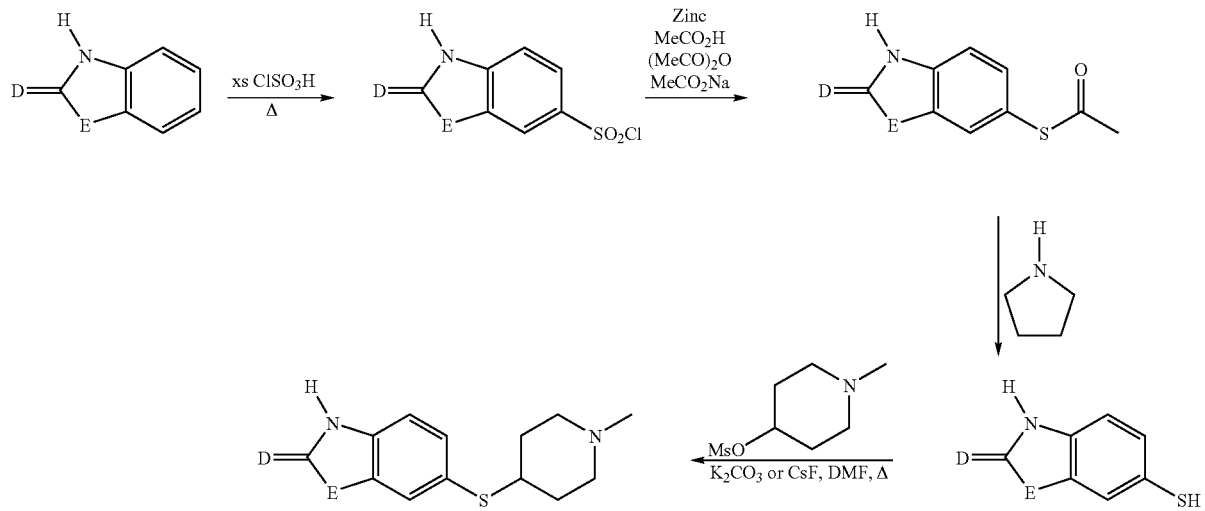

Unsubstituted precursors to compounds of group $F^1$ and $F^2$ (wherein $R^3$=H, $R^4$=H, D=O or S and E=O, S, NH, O—$CR^5_2$, $NR^5$—$CR^5_2$, $NR^5$—CO, $CR^5_2$—O, $CR^5_2$—S, $CR^5_2$—$NR^5$, $CR^5_2$—$CR^5_2$, CO—$NR^5$, or $CR^5$=$CR^5$) may be treated with excess chlorosulphonic acid to selectively introduce a chlorosulphonyl group para to the N—H. The chlorosulphonic acid may be used neat or in a solvent such as chloroform or dichloromethane at a temperature between 0 and 100° C. Reduction to the acetylthio compound may be effected with zinc, acetic anhydride and acetic acid at a temperature between 0° C. and ambient temperature. Removal of the acetyl group may be effected by a secondary amine such as pyrollidine and subsequent alkylation of the free thiol with an appropriate mesylate may be mediated by a base such as potassium carbonate or cesium fluoride in an aprotic solvent such as dimethylformamide. This reaction is performed between ambient temperature and 100° C.

An alternative route to aryl thiols is shown in scheme 7 for D=E=O and $R^3$=Me. This utilises 1 equivalent of chlorosulphonic acid at 0° C. and ambient temperature to give a sulphonic acid derivative which may be reduced directly to a thiol using iodine and triphenylphosphine in a solvent such as benzene at reflux under Dean and Stark conditions.

Reaction Scheme 7

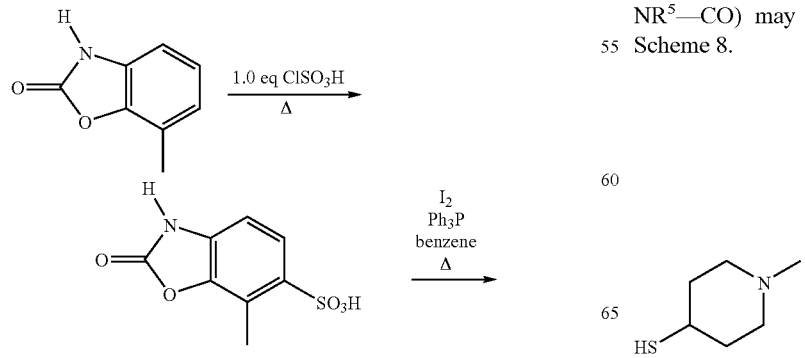

-continued

Substituted compounds of group $F^1$ and $F^2$ ($R^3$=H, Cl, $R^4$=H, D=O, S and E=O, S, $NR^5$, O—$CR^5_2$, $NR^5$—$CR^5_2$, $NR^5$—CO) may be prepared by a route exemplified in Scheme 8.

Reaction Scheme 8

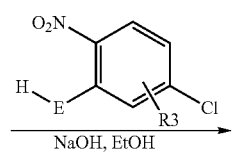

-continued

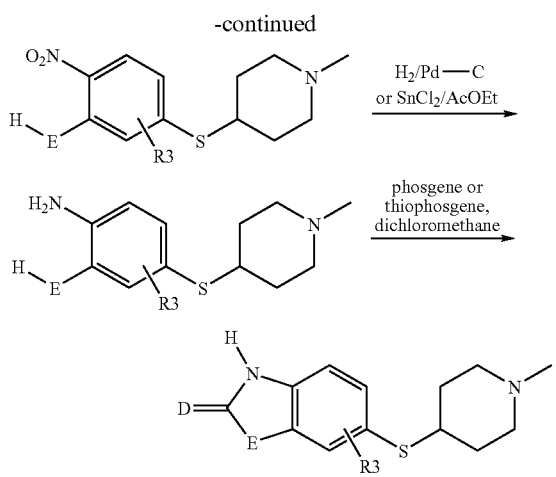

An azamonocyclic thiol (prepared according to *J. Med. Chem.* 1993, 36, 3261) may be used to displace a halo atom (eg chlorine) from an appropriately substituted nitrophenyl derivative in a reaction mediated by a base such as sodium hydride at ambient temperature. The resultant nitro derivative may be reduced by catalytic hydrogenation in a protic solvent such as ethanol or by tin chloride in ethyl acetate at reflux temperature. Finally reaction with phosgene (or a synthetic equivalent e.g. triphosgene) or thiophosgene in a solvent such as dichloromethane or chloroform at a temperature between ambient and reflux temperature gives rise to the compounds of group $F^1$ and $F^2$ specified.

Compounds of Group $F^2$ where D=O, E=CR$^5$=CR$^5$ and R3=R4 may be prepared by a procedure exemplified in Reaction Scheme 9.

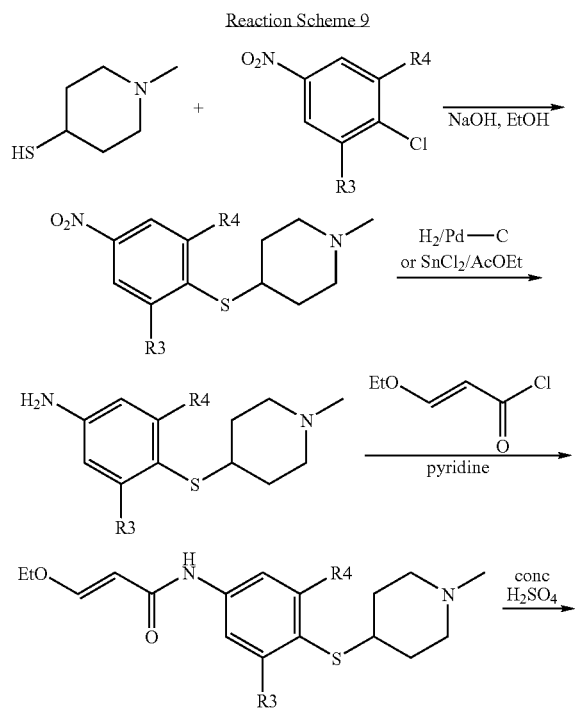

-continued

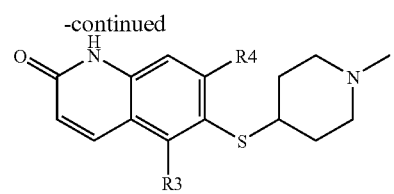

A thio compound may be used to displace a halo atom (eg chlorine) from an appropriately substituted nitrophenyl derivative in a reaction mediated by a base such as sodium hydride at ambient temperature. The resultant nitro derivative may be reduced by catalytic hydrogenation in a protic solvent such as ethanol or by tin chloride in ethyl acetate at reflux temperature. The aniline derivative so obtained is acylated with (E)-3-ethoxy-2-propenoyl chloride in a solvent such as dichloromethane in the presence of a non-nucleophilic base such as pyridine at a temperature between 0° C. and ambient temperature. The resultant amide may be cyclized with a concentrated mineral acid such sulphuric acid at a temperature between 0° C. and ambient temperature.

The conversion of C=O moieties to C=S may be achieved by reaction with Lawesson's reagent [2,4-bis(4-methoxyphenyl)-1,3-dithia-2,4-diphosphetane-2,4-disulfide)] in a solvent such as toluene at refluxing temperature as shown in Scheme 10.

Reaction Scheme 10

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Further discussion of pro-drugs may be found in Stella, V. J. et al., "Prodrugs", *Drug Delivery Systems*, 1985, pp. 112-176, and *Drugs*, 1985, 29, pp. 455-473.

Pharmaceutically acceptable salts of the acidic or basic compounds of the invention can of course be made by conventional procedures, such as by reacting the free base or acid with at least a stoichiometric amount of the desired salt-forming acid or base.

Pharmaceutically acceptable salts of the acidic compounds of the invention include salts with inorganic cations such as sodium, potassium, calcium, magnesium, and zinc, and salts with organic bases. Suitable organic bases include N-methyl-D-glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tartrate, tartrate, terephthalate, tosylate and triethiodide.

Another aspect of the present invention is a pharmaceutical composition comprising a compound of formula (I) for use in therapy substantially as described hereinbefore with a pharmaceutically acceptable diluent or carrier.

It is anticipated that the compounds of the invention can be administered by oral or parenteral routes, including intravenous, intramuscular, intraperitoneal, subcutaneous, rectal and topical administration, and inhalation.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate and lactose. Corn starch and alginic acid are suitable disintegrating agents. Binding agents may include starch and gelatine. The lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatine capsules in which the active ingredient is mixed with a solid diluent and soft gelatine capsules wherein the active ingredient is mixed with water or an oil such as peanut oil, liquid paraffin or olive oil.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxy-benzoate.

Compounds of the invention have been demonstrated to be active at the neuronal nicotinic beta 4 receptor. Their functional agonist activity has been demonstrated in the test described below.

Functional Ca-flux Assay

HEK 293 cell lines expressing different nicotinic receptor β4 subtypes are plated at a density of 50,000 cells/well into poly-D-lysine coated 96 well microtitre plates. Twenty-four hours later the cells are washed with buffer and loaded with Fluo-3 dye (10 M) at room temperature for 1 h. The dye is removed and 180 µl of buffer containing atropine at 3 µM added.

The plates are loaded into a FLIPR (Molecular Devices) and 20 µl of experimental compound are added in a concentration gradient across the plate. The stimulation of the nicotinic receptor response to compound addition is measured as a rise in fluorescence which correlates to the entry of calcium into the cell. Acetylcholine is added 10 min later to all wells to investigate whether the compounds can block the acetylcholine stimulated nicotine response.

The effects of compounds as nicotinic agonists and antagonists are calculated using an OMM (Oxford matrix management) curve fit package.

The present invention further provides the use of compounds of formula (I) in the manufacture of a medicament for the treatment of conditions indicating treatment with a beta 4 selective nicotinic acetylcholine receptor modulator and in the manufacture of a medicament for the treatment of dysfunctions of the central and autonomic nervous systems. Such dysfunctions included, for example, dementia, cognitive disorders, neurodegenerative disorders, extrapyramidal disorders, convulsive disorders, cardiovascular disorders, endocrine disorders, eating disorders, affective disorders, and drug abuse.

The present invention is now further illustrated by means of the following Examples.

EXAMPLE 1

4-(4-Hydroxyphenylthio)-piperidine trifluoroacetate

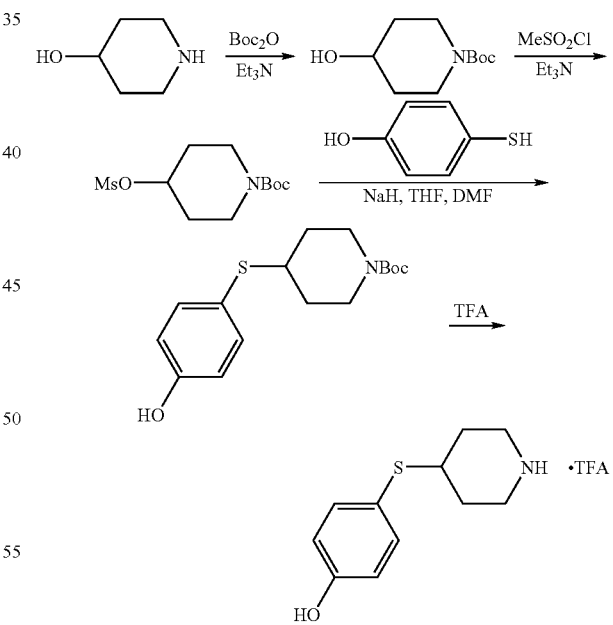

i) 1-(tert-Butoxycarbonyl)-4-hydroxy-piperidine

A mixture of 4-hydroxy-piperidine (10.1 g), triethylamine (14 ml), di-tert-butyl dicarbonate (22 g) in dichloromethane (150 ml) is stirred at ambient temperature for 18 hours. The reaction mixture is washed with 150 ml portions of 1.0M hydrochloric acid and water. The organic layer is dried over magnesium sulphate and concentrated to dryness to give the title compound as a colourless oil (20 g). $^1$H NMR (300 MHz) (CDCl$_3$) 3.85 (m, 3H), 3.02 (m, 2H), 1.80 (brm, 3H), 1.50 (brm, 2H), 1.45 (s, 9H).

ii) 1-(tert-Butoxycarbonyl)-4-methanesulfonyloxy-piperidine

A mixture of N-(tert-butoxycarbonyl)-4-hydroxy-piperidine (6.0 g, Reference Example 1), triethylamine (12.5 ml) and dichloromethane (150 ml) is treated dropwise with methanesulfonylchloride (3.0 ml) and stirred for 3 hours at ambient temperature. The reaction mixture is washed with 1.0M hydrochloric acid and dried over magnesium sulphate before being concentrated to dryness. The title compound is obtained as a colourless waxy solid. $^1$H NMR (300 MHz) (CDCl$_3$) 4.87 (m, 1H) 3.80 (m, 2H), 3.28 (m, 2H), 3.01 (s, 3H), 1.95 (m, 2H), 1.80 (m, 2H), 1.45 (s, 9H).

iii) 1-(tert-Butoxycarbonyl)-4-(4-hydroxyphenylthio)-piperidine

A mixture of 4-mercaptophenol (1.26 g), sodium hydride (0.88 g of 60% dispersion in mineral oil), dry tetrahydrofuran (50 ml) and dry dimethylformamide (25 ml) is stirred at ambient temperature for 15 minutes. The resultant reaction mixture is treated with N-(tert-butoxycarbonyl)-4-methanesulfonyloxy-piperidine (2.8 g, Reference Example 2) and heated to 70° C. for 6 hours. The reaction mixture is cooled, concentrated to dryness and the residue partitioned between water (100 mL) and dichloromethane (3×50 ml). The combined organics were dried over magnesium sulphate and concentrated to leave the title compound as a pale yellow oil (2.2 g). MS (FIA) 332 (100%, M+Na), $^1$H NMR (300 MHz) (CDCl$_3$) 8.01 (s, 1H), 7.20 (m, 2H), 6.90 (m, 2H), 3.98 (m, 1H) 2.95 (m, 5H), 1.86 (m, 2H), 1.45 (m, 1H), 1.44 (s, 9H).

iv) 4-(4-Hydroxyphenylthio)-piperidine trifluoroacetate

A mixture of 1-(tert-butoxycarbonyl)-4-(4-hydroxyphenylthio)-piperidine (2.2 g, Reference Example 3), dichloromethane (50 ml) and trifluoroacetic acid (5 ml) is stirred at 0° C. for 3 hours before being concentrated to dryness. The residue is triturated with ether to give the title compound as a colourless amorphous solid (1.0 g). MS (FIA) 242 (100%, M+H), $^1$H NMR (300 MHz) (DMSO) 9.85 (br s, 1H), 8.60 (br s, 1H), 7.30 (m, 2H), 6.72 (m, 2H), 3.22 (m, 2H) 3.18 (m, 1H), 2.90 (m, 2H), 1.93 (m, 2H), 1.45 (m, 2H).

EXAMPLE 2

1-(2-Hydroxyethyl)-4-(4-hydroxyphenylthio)-piperidine

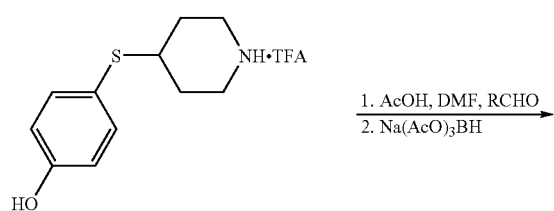

1. AcOH, DMF, RCHO
2. Na(AcO)$_3$BH

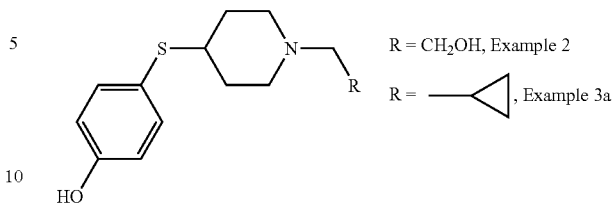

R = CH$_2$OH, Example 2
R = —◁, Example 3a 4-(4-hydroxyphenylthio)-piperidine trifluoroacetate (170 mg, Example 1) is dissolved in a mixture of dichloromethane (8 ml) and methanol (4 ml). This solution is treated with MP-carbonate resin (250 mg, Argonaut) and stirred for 1 hour at ambient temperature. The supernatant solution is removed and concentrated to dryness. The residue is dissolved in 1% acetic acid in dimethylformamide (10 ml), treated with glycolaldehyde (65 mg) and allowed to stand at ambient temperature for 2 hours. The resultant reaction mixture is treated with sodium triacetoxyborohydride (200 mg) and allowed to stand at ambient temperature for 18 hours. The solvent is removed in vacuo and the residue partitioned between chloroform (20 ml) and 5% aqueous sodium bicarbonate solution (20 ml). The organic layer is dried over magnesium sulphate and concentrated to dryness. The residue is chromatographed on silica gel eluting with a mixture of dichloromethane and methanol (4/1) to give the title compound as a colourless amorphous solid (50 mg). MS (FIA) 254 (100%, M+H), $^1$H NMR (300 MHz) (DMSO) 9.70 (s, 1H), 7.28 (m, 2H), 6.70 (m, 2H), 4.30 (m, 1H) 4.05 (br s, 1H), 3.42 (m, 2H), 3.38 (m, 2H), 2.80 (br m, 2H), 2.00 (br m, 2H), 1.78 (br m, 2H), 1.44 (br m, 2H).

EXAMPLE 3

(a) 1-(4-Cyclopropylmethyl)-4-(4-hydroxyphenylthio)-piperidine

A mixture of 4-(4-hydroxyphenylthio)-piperidine trifluoroacetate (480 mg, Example 1) and MP-carbonate resin (600 mg, Argonaut) in dry dimethylformamide (12 ml) is stirred for 1 hour at ambient temperature. The supernatant solution is removed and a 0.5 ml aliquot was added to a solution of cyclopropanecarboxaldehyde (9 mg) in 1% acetic acid/dimethylformamide (0.5 ml). This reaction mixture is allowed to stand at ambient temperature for 2 hours before being treated with 0.5 ml of a 0.25M solution of sodium triacetoxyborohydride (200 mg) in 1% acetic acid/dimethylformamide. The reaction mixture is allowed to stand at ambient temperature for a further 18 hours. The solvent is removed in vacuo and the residue partitioned between chloroform (2 ml) and 5% aqueous sodium bicarbonate solution (1 ml). The organic layer is separated and concentrated to dryness. The residue is dissolved in methanol (2 ml) and applied to a 3 ml SCX ion exchange column (Jones Chromatography, preconditioned with 2×2 ml methanol). The column was eluted with methanol (2×2 ml) and 2.0M ammonia in methanol (2×2 ml). The ammonia/methanol fractions was concentrated in vacuo to leave the title compound as a yellow oil. LCMS 264 (100%, M+H), Rt=1.9 min (gradient 95:5 water:acetonitrile to 95:5 acetonitrile:water over 8 min).

By proceeding in a similar manner but using the appropriate aldehyde in place of cyclopropanecarboxaldehyde there is prepared:

(b) (R/S)-1-(2,3-Dihydroxy-1-propyl)-4-(4-hydroxyphenylthio)-piperidine

LCMS 284 (100%, M+H), Rt=1.4 min.

(c) 1-(Cyclohexylmethyl)-4-(4-hydroxyphenylthio)-piperidine

LCMS 306 (95%, M+H), Rt=2.6 min.

(d) 1-(2-Furanylmethyl)-4-(4-hydroxyphenylthio)-piperidine

LCMS 290 (82%, M+H), Rt=2.1 min.

(e) 1-(2-Methyl-1-propyl)-4-(4-hydroxyphenylthio)-piperidine

LCMS 266 (100%, M+H), Rt=2.0 min.

(f) 1-(4-Methoxybenzyl)-4-(4-hydroxyphenylthio)-piperidine

LCMS 330 (95%, M+H), Rt=2.4 min.

(g) 1-Benzyl-4-(4-hydroxyphenylthio)-piperidine

LCMS 300 (100%, M+H), Rt=2.3 min.

(h) 1-(n-Butyl)-4-(4-hydroxyphenylthio)-piperidine

LCMS 266 (93%, M+H), Rt=2.1 min.

(i) 1-(3-Methyl-1-butyl)-4-(4-hydroxyphenylthio)-piperidine

LCMS 280 (92%, M+H), Rt=2.4 min.

(j) 1-(2-Hydroxyethyl)-4-(4-hydroxyphenylthio)-piperidine

LCMS 254 (93%, M+H), Rt=1.4 min.

(k) 1-(2-Imidazolylmethyl)-4-(4-hydroxyphenylthio)-piperidine

LCMS 290 (100%, M+H), Rt=1.6 min.

(l) 1-(1-Methyl-2-pyrollylmethyl)-4-(4-hydroxyphenylthio)-piperidine

LCMS 303 (74%, M+H), Rt=2.2 min.

(m) 1-(2-phenethyl)-4-(4-hydroxyphenylthio)-piperidine

LCMS 314 (35%, M+H), Rt=2.6 min.

(n) 1-(n-Propyl)-4-(4-hydroxyphenylthio)-piperidine

LCMS 252 (90%, M+H), Rt=1.8 min.

(o) 1-(2-Pyridylmethyl)-4-(4-hydroxyphenylthio)-piperidine

LCMS 301 (100%, M+H), Rt=1.9 min.

(p) 1-(2-Thiophenylmethyl)-4-(4-hydroxyphenylthio)-piperidine

LCMS 306 (97%, M+H), Rt=2.2 min.

(q) 1-(2,2-Dimethyl-1-propyl)-4-(4-hydroxyphenylthio)-piperidine

LCMS 280 (84%, M+H), Rt=1.5 min.

(r) 1-(2-Phenyl-4-imidazolylmethyl)-4-(4-hydroxyphenylthio)-piperidine

LCMS 366 (72%, M+H), Rt=2.3 min.

(s) 1-(1-Oxo-4-pyridylmethyl)-4-(4-hydroxyphenylthio)-piperidine

LCMS 317 (100%, M+H), Rt=1.4 min.

(t) 1-(-Methyl-2-imidazolylmethyl)-4-(4-hydroxyphenylthio)-piperidine

LCMS 304 (100%, M+H), Rt=1.9 min.

(u) 1-(2-Thiazolylmethyl)-4-(4-hydroxyphenylthio)-piperidine

LCMS 307 (100%, M+H), Rt=1.9 min.

(v) 1-(3,3-Dimethyl-1-butyl)-4-(4-hydroxyphenylthio)-piperidine

LCMS 294 (100%, M+H), Rt=2.6 min.

(w) (R/S)-1-(2-Methyl-1-butyl)-4-(4-hydroxyphenylthio)-piperidine

LCMS 280 (100%, M+H), Rt=2.3 min.

(x) 1-(3-Methylthio-1-propyl)-4-(4-hydroxyphenylthio)-piperidine

LCMS 298 (69%, M+H), Rt=2.1 min.

EXAMPLE 4

4-(1-methylpiperidin-4-yl)thiophenol

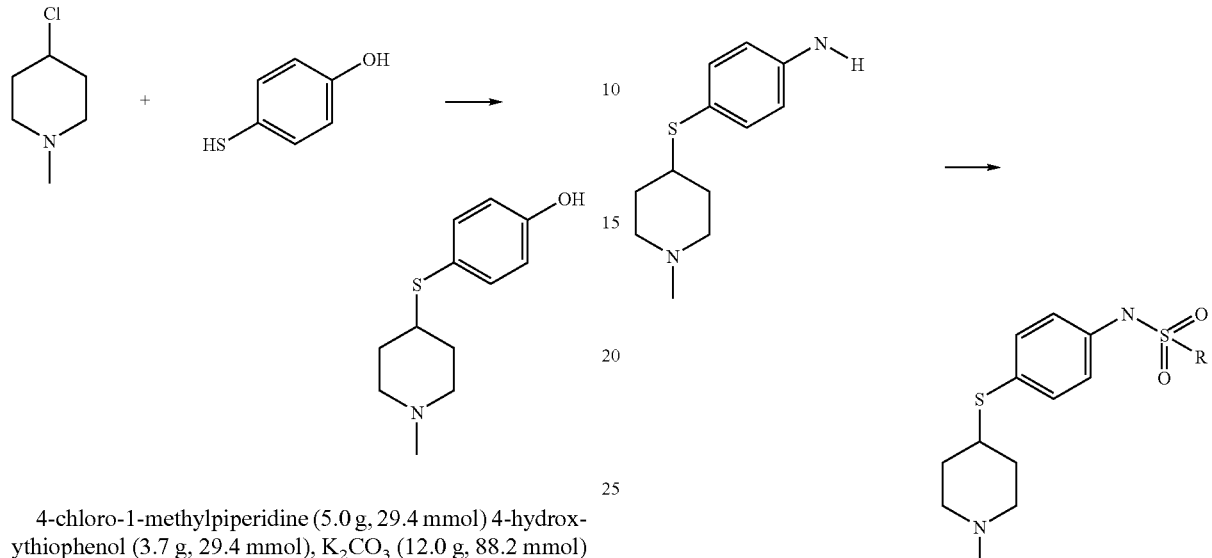

4-chloro-1-methylpiperidine (5.0 g, 29.4 mmol) 4-hydroxythiophenol (3.7 g, 29.4 mmol), $K_2CO_3$ (12.0 g, 88.2 mmol) and anhydrous DMF (90 mL) afforded 2.85 g (43%) of the desired compound which is converted to the hydrochloride salt. $^1$H NMR (CDCl$_3$) 7.23 (m, 2H), 6.64 (m, 2H), 3.38-3.18 (m, 3H), 2.92-2.69 (m, 2H), 2.69 (s, 3H), 2.05-2.00 (m, 2H), 1.62-1.57 (m, 2H); mp 170-172° C.; LRMS (EI) m/e 223.

EXAMPLE 5

4-(1-methylpiperidin-4-yl)thiophenylamine

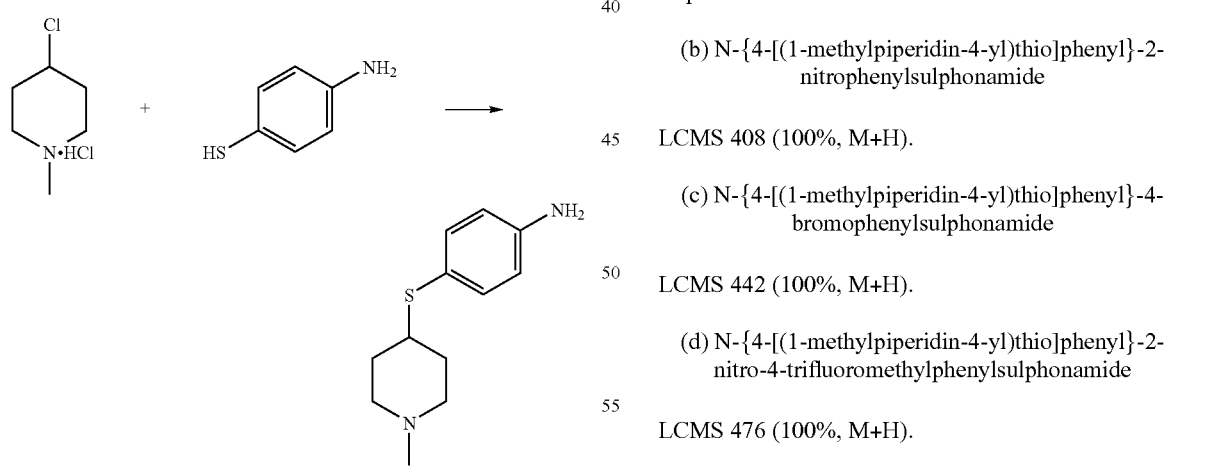

4-chloro-1-methylpiperidine hydrochloride (6.46 g, 38 mmol) 4-mercaptoaniline (5.0 g, 40.0 mmol), $K_2CO_3$ (16.5 g, 120 mmol) and anhydrous DMF (120 mL) afforded 1.9 g (21%) of the desired compound which is converted to the hydrochloride salt. $^1$H NMR (CDCl$_3$) 7.19 (m, 2H), 6.52 (m, 2H), 3.69 (brs, 2H 2.74-2.70 (m, 3H), 2.15 (s, 3H), 1.92-1.79 (m, 4H), 1.59-1.47 (m, 2H); mp 96-98° C.; LCMS m/z 222 (M$^+$).

EXAMPLE 6

(a) N-{4-[(1-methylpiperidin-4-yl)thio]phenyl}-2-chlorophenylsulphonamide

In a typical procedure, 4-(1-methylpiperidin-4-yl)thiophenylamine is stirred for 12 hours with 1 equivalent of 2-chlorophenylsulphonyl chloride and 1 equivalent of pyridine in dichloromethane. The solvents are removed in vacuo and the residue purified by preparative HPLC to give an oil. LCMS 397 (100%, M+H).

By proceeding in a similar manner, using the appropriate arylsulphonyl chloride there were prepared the following examples:

(b) N-{4-[(1-methylpiperidin-4-yl)thio]phenyl}-2-nitrophenylsulphonamide

LCMS 408 (100%, M+H).

(c) N-{4-[(1-methylpiperidin-4-yl)thio]phenyl}-4-bromophenylsulphonamide

LCMS 442 (100%, M+H).

(d) N-{4-[(1-methylpiperidin-4-yl)thio]phenyl}-2-nitro-4-trifluoromethylphenylsulphonamide

LCMS 476 (100%, M+H).

(e) N-{4-[(1-methylpiperidin-4-yl)thio]phenyl}-2-chloro-3-nitrophenylsulphonamide

LCMS 442 (100%, M+H).

(f) N-{4-[(1-methylpiperidin-4-yl)thio]phenyl}-methoxyphenylsulphonamide

LCMS 393 (100%, M+H).

(g) N-{4-[(1-methylpiperidin-4-yl)thio]phenyl}-4-fluorophenylsulphonamide

LCMS 381 (100%, M+H).

(h) N-{4-[(1-methylpiperidin-4-yl)thio]phenyl}-4-methylphenylsulphonamide

LCMS 377 (100%, M+H).

(i) N-{4-[(1-methylpiperidin-4-yl)thio]phenyl}-4-methoxy-2-nitrophenylsulphonamide

LCMS 438 (100%, M+H).

(j) N-{4-[(1-methylpiperidin-4-yl)thio]phenyl}-2-naphthylsulphonamide

LCMS 413 (100%, M+H).

(k) N-{4-[(1-methylpiperidin-4-yl)thio]phenyl}-2,4,6-trimethylphenylsulphonamide

LCMS 405 (100%, M+H).

(l) N-{4-[(1-methylpiperidin-4-yl)thio]phenyl}-4-methyl-2-methoxyphenylsulphonamide

LCMS 407 (100%, M+H).

(m) N-{4-[(1-methylpiperidin-4-yl)thio]phenyl}-4-chlorophenylsulphonamide

LCMS 397 (100%, M+H).

(n) N-{4-[(1-methylpiperidin-4-yl)thio]phenyl}-2,5-dichloro-3-thiophenylsulphonamide

LCMS 438 (100%, M+H).

(o) N-{4-[(1-methylpiperidin-4-yl)thio]phenyl}-4-isopropylphenylsulphonamide

LCMS 405 (100%, M+H).

(p) N-{4-[(1-methylpiperidin-4-yl)thio]phenyl}-4-ethylphenylsulphonamide

LCMS 391 (100%, M+H).

(q) N-{4-[(1-methylpiperidin-4-yl)thio]phenyl}-4-methoxy-2,5,6-trimethylphenylsulphonamide

LCMS 435 (100%, M+H).

(r) N-{4-[(1-methylpiperidin-4-yl)thio]phenyl}-3-methoxyphenylsulphonamide

LCMS 493 (100%, M+H).

(s) N-{4-[(1-methylpiperidin-4-yl)thio]phenyl}-4-methanesulphonylphenylsulphonamide

LCMS 441 (100%, M+H).

(t) N-{4-[(1-methylpiperidin-4-yl)thio]phenyl}-2,5-dimethylphenylsulphonamide

LCMS 390 (100%, M+H).

(u) N-{4-[(1-methylpiperidin-4-yl)thio]phenyl}-2,3,4-trifluorophenylsulphonamide

LCMS 417 (100%, M+H).

(v) N-{4-[(1-methylpiperidin-4-yl)thio]phenyl}-4-acetylaminophenylsulphonamide

LCMS 420 (100%, M+H).

(w) N-{4-[(1-methylpiperidin-4-yl)thio]phenyl}-4-trifluoromethoxyphenylsulphonamide

LCMS 448 (100%, M+H).

(x) N-{4-[(1-methylpiperidin-4-yl)thio]phenyl}-3-bromophenylsulphonamide

LCMS 442 (100%, M+H).

(y) N-{4-[(1-methylpiperidin-4-yl)thio]phenyl}-3,4-dichlorophenylsulphonamide

LCMS 432 (100%, M+H).

(z) N-{4-[(1-methylpiperidin-4-yl)thio]phenyl}-3-cyanophenylsulphonamide

LCMS 388 (100%, M+H).

(aa) N-{4-[(1-methylpiperidin-4-yl)thio]phenyl}-2-trifluoromethoxyphenylsulphonamide

LCMS 447 (100%, M+H).

(ab) N-{4-[(1-methylpiperidin-4-yl)thio]phenyl}-3-methoxycarbonyl-2-thiophenylsulphonamide

LCMS 427 (100%, M+H).

(ac) N-{4-[(1-methylpiperidin-4-yl)thio]phenyl}-4-n-hexylphenylsulphonamide

LCMS 433 (100%, M+H).

(ad) N-{4-[(1-methylpiperidin-4-yl)thio]phenyl}-4-bromo-2-methylphenylsulphonamide

LCMS 456 (100%, M+H).

EXAMPLE 7

N-{4-[(1-methylpiperidin-4-yl)thio]phenyl}acetamide

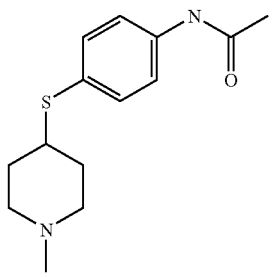

4-methanesulfonate-1-methylpiperidine hydrochloride (1.58 g, 8.19 mmol) 4-acetamido-thiophenol (1.52 g, 8.19 mmol), K$_2$CO$_3$ (5.66 g, 4.97 mmol) and anhydrous DMF (30 mL) afforded 350 mg (14%) of the desired compound which is converted to the fumaric salt. $^1$H NMR (CDCl$_3$) 7.57 (m, 2H), 7.44 (m, 2H), 6.68 (s, 2H), 3.4 (m, 2H), 3.3 (m, 1H), 3.05 (m, 2H), 2.15 (m, 2H) 2.11 (s, 3H), 2.11 (m, 2H), mp 199-201° C.; LCMS m/z 265 (MH$^+$).

EXAMPLE 8

3-Chloro-4-(1-methylpiperidin-4-yl)thiophenol

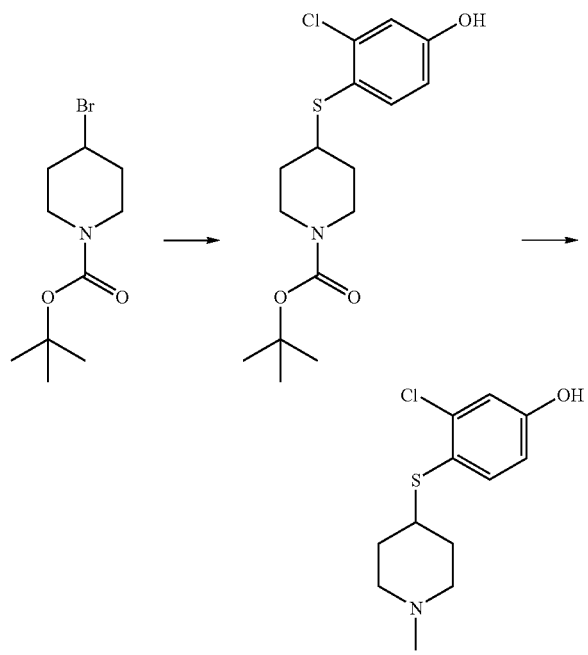

i) Tert-butyl-4-bromopiperidine-1-carboxylate

Prepared in 88% yield following the procedure described for tert-butyl-(3R)-3-hydroxy pyrrolidine-1-carboxylate using tert-butyl-4-hydroxypiperidine-1-carboxylate (1 g, 4.95 mmol), carbon tetrabromide (2.46 g, 7.42 mmol), and triphenylphosphine (1.95 g, 7.42 mmol) in CH$_2$Cl$_2$ (25 mL).

$^1$H NMR (CDCl$_3$) 4.37-4.32 (m, 1H), 3.72-3.64 (m, 2H), 3.35-3.27 (m, 2H), 2.12-2.04 (m, 2H), 1.98-1.88 (m, 2H), 1.46 (s, 9H).

ii) Tert-butyl-4-[(2-chloro-4-hydroxyphenyl)thio]piperidine-1-carboxylate

Prepared in 70% yield following the procedure described for tert-butyl-(3R)-3-[(2-chloro-4-hydroxyphenyl)thio]pyrrolidine-1-carboxylate using Tert-butyl-4-bromo piperidine-1-carboxylate (200 mg, 0.76 mmol), 2-chloro-4-hydroxythiophenol (134 mg, 0.84 mmol), and K$_2$CO$_3$ (315 mg, 2.28 mmol) in DMF (8 mL) as starting mixture. $^1$H NMR (CDCl$_3$) 7.64 (s, 1H), 7.38 (d, J=8.43 Hz, 1H), 7.00 (s, 1H), 6.72 (dd, J=8.43, 2.52 Hz, 1H), 3.95 (m, 2H), 3.19 (m, 1H), 2.93 (bs, 2H), 1.82 (bs, 2H), 1.52 (m, 2H), 1.46 (s, 9H).

iii) 3-Chloro-4-(1-methylpiperidin-4-yl)thiophenol

Prepared following the procedure described for 3-chloro-4-[(3R)-1-methylpyrrolidin-3-yl]thiophenol in 59% yield using tert-butyl-4-[(2-chloro-4-hydroxyphenyl)thio]piperidine-1-carboxylate (180 mg, 0.52 mmol) and AlLiH$_4$ (1M in THF, 1.2 mL, 1.14 mmol) in CH$_2$Cl$_2$ (5.2 mL) as starting mixture followed by subsequent addition of 0.5 mL of AlLiH$_4$. $^1$H NMR (CDCl$_3$) 7.40 (d, J=8.46 Hz, 1H), 6.90 (s, 1H), 6.68 (dd, J=8.43, 2.61 Hz, 1H), 3.56 (m, 1H), 3.31-3.29 (m, 2H), 2.29 (s, 3H), 2.18 (m, 2H), 1.93-1.87 (m, 2H), 1.64-1.59 (m, 2H); LCMS m/z 258 (M$^+$); Rf=0.47 (CHCl$_3$:MeOH, 8:2).

EXAMPLE 9

3-Chloro-4-(piperidin-4-yl)thiophenol.hydrochloride

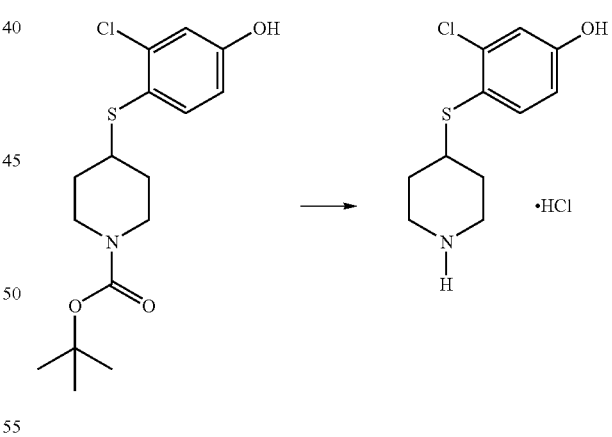

To a solution of tert-butyl-4-[(2-chloro-4-hydroxyphenyl)thio]piperidine-1-carboxylate (160 mg, 0.46 mmol) in CH$_2$Cl$_2$ (5 mL) is added HCl (4M in 1,4-dioxane, 0.25 mL, 0.92 mmol). The resulting clear solution is stirred at room temperature overnight under Argon. The white precipitate is filtered, washed with ether, and dried to afford 93.4 mg (84%) of the desired compound. $^1$H NMR (CD$_3$OD) 7.46 (d, J=8.52 Hz, 1H), 6.93 (s, 1H), 6.73 (dd, J=8.52, 2.61 Hz, 1H), 3.44-3.29 (m, 3H), 3.09-3.00 (m, 2H), 2.15-2.08 (m, 2H), 1.81-1.70(m, 2H); $^{13}$C NMR (CD$_3$OD) 159.1, 139.5, 137.9, 119.6, 116.6, 114.6, 42.7, 41.2, 28.4; LCMS m/z 245 (M$^+$+1); Rf=0.40 (n-BuOH:H$_2$O:AcOH, 6:2:2).

EXAMPLE 10

3-chloro-4-[(3R)-1-methylpyrrolidin-3-yl]thiophenol

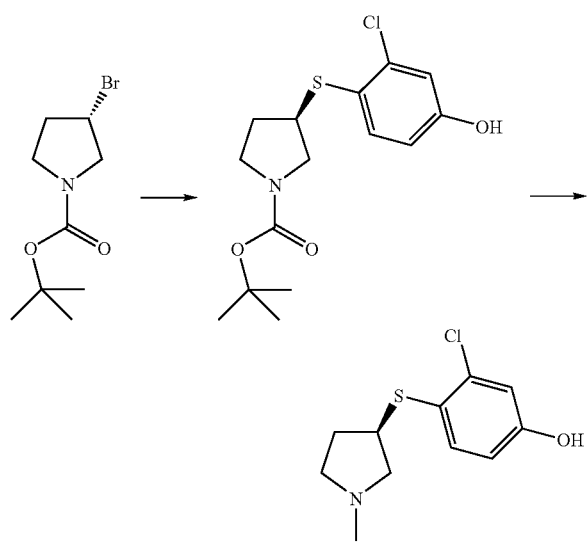

i) Tert-butyl-(3S)-3-bromopyrrolidine-1-carboxylate

A mixture of tert-butyl-(3R)-3-hydroxypyrrolidine-1-carboxylate (500 mg, 2.67 mmol) and triphenylphosphine (1 g, 4 mmol) in anhydrous $CH_2Cl_2$ (10 mL) is cooled to 0-5° C. under Argon. Carbon tetrabromide (1.33 g, 4 mmol) dissolved in $CH_2Cl_2$ (5 mL) is then slowly added keeping the temperature below 10° C. The resulting yellow mixture is allowed to warm to room temperature and stirred overnight. The solvent is removed in vacuo and the viscous yellow residue is purified by flash chromatography (silica gel, Hexane:EtOAc, 3:1 and then 1:1) to afford 520 g (78%) of the compound as a colorless oil. $^1$H NMR ($CDCl_3$) 4.48 (bs, 1H), 3.82-3.46 (m, 4H), 2.36-2.20 (m, 2H), 1.47 (s, 9H).

ii) tert-butyl-(3R)-3-[(2-chloro-4-hydroxyphenyl)thio]pyrrolidine-1-carboxylate tert-butyl-(3S)-3-bromopyrrolidine-1-carboxylate (400 mg, 1.6 mmol), 2-chloro-4-hydroxythiophenol (308 mg, 1.92 mmol), $K_2CO_3$ (662 mg, 4.8 mmol) and anhydrous DMF (16 mL) afforded 457 mg (87%) of the desired compound as a white solid. $^1$H NMR ($CDCl_3$) 7.30 (d, J=8.37 Hz, 1H), 6.98 (s, 1H), 6.72 (d, J=7.92 Hz, 1H), 3.72-3.66 (bs, 1H), 3.61-3.48 (m, 2H), 3.43-3.28 (m, 2H), 2.24-2.08 (m, 1H), 1.97-1.81 (m, 1H), 1.48 (s, 1H).

iii) 3-chloro-4-[(3R)-1-methylpyrrolidin-3-yl]thiophenol

To a stirred solution of tert-butyl-(3R)-3-[(2-chloro-4-hydroxyphenyl)thio]pyrrolidine-1-carboxylate (200 mg, 0.61 mmol) in anhydrous THF (10 mL) under Argon is added $AlLiH_4$ (1M in THF, 1.3 mL, 1.34 mmol) at room temperature. The resulting clear solution is stirred at room temperature overnight. 1.7 equivalents of $AlLiH_4$ (1M in THF, 1 mL, 1 mmol) is added and the stirring is extended for 2 days. $H_2O$ is slowly added to quench the reaction. The white precipitate is filtered and washed with $CH_2Cl_2$ and EtOAc. The organics are washed with a saturated NaCl solution (2×), combined, dried over $Na_2SO_4$, and concentrated under reduced pressure to give a yellow oil. Purification by flash chromatography (silica gel, $CHCl_3$ and then $CHCl_3$:MeOH, 95:5) afforded 50 mg (34%) of the desired compound as a yellow oil. $^1$H NMR ($CDCl_3$) 7.66 (bs, 1H), 7.28 (d, J=8.37 Hz, 1H), 6.84 (s, 1H), 6.59 (dd, J=8.46, 2.52 Hz, 1H), 3.75-3.70 (m, 1H), 3.08-3.02 (m, 1H), 2.81-2.74 (m, 2H), 2.60-2.54 (m, 1H), 2.44 (s, 3H), 2.33-2.25 (m, 1H), 1.89-1.85 (m, 1H); $^{13}$C NMR ($CDCl_3$) 158.6, 138.1, 135.9, 122.2, 117.8, 115.4, 62.0, 55.1, 43.9, 41.9, 31.8; LCMS m/z 244 ($M^+$), Rf=0.53 ($CHCl_3$:MeOH, 8:2).

EXAMPLE 11

3-Chloro-4-[(3R)-pyrrolidin-3-yl]thiophenol.hydrochloride

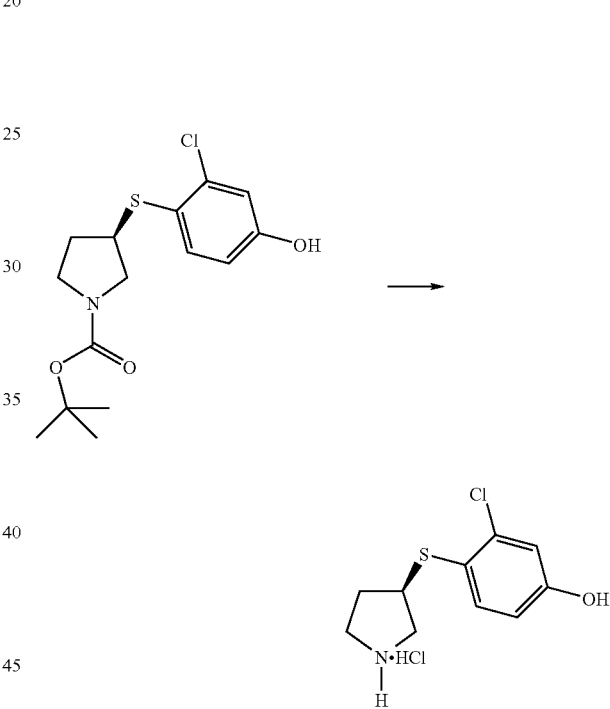

To a stirred solution of tert-butyl-(3R)-3-[(2-chloro-4-hydroxyphenyl)thio]pyrrolidine-1-carboxylate (100 mg, 0.3 mmol) in anhydrous $CH_2Cl_2$ (2 mL) and MeOH (1 mL) under Argon is added HCl (4M in 1,4-dioxane, 0.15 mL). The resulting clear solution is stirred at room temperature overnight. More HCl (4M in 1,4-dioxane, 0.15 mL) is added and the mixture is stirred for 5 hr. The solvent is removed in vacuo and the residue was purified by preparative HPLC (Phenominex Polar-RP, 1"×10 cm×4 micron, A: $H_2O$/TFA, 100:0.1, B: ACN/TFA, 100:0.05, gradient from A to B over 15 min, Rf=8 min, UV=254 nm). $^1$H NMR ($CD_3OD$) 7.48 (d, J=8.4 Hz, 1H), 6.95 (s, 1H), 6.75 (dd, J=8.4, 2.4 Hz, 1H), 3.94 (qt, J=6.3 Hz, 1H), 3.5 (m, 2H), 3.36 (m, 1H), 3.18 (m, 1H), 2.33 (m, 1H), 1.95 (m, 1H); $^{13}$C NMR ($CD_3OD$) 159.8, 139.4, 137.8, 120.1, 117.1, 115.1, 50.4, 44.6, 44.6, 30.4; LCMS m/z 230 ($M^++1$); Rf=0.36 (n-BuOH:$H_2O$:AcOH, 6:2:2).

EXAMPLE 12

3-Chloro-4-[(3S)-1-methylpyrrolidin-3-yl]thiophenol

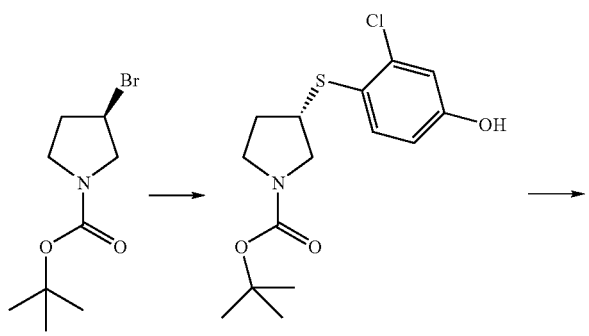

i) Tert-butyl-(3R)-3-bromopyrrolidine-1-carboxylate

Prepared following the procedure described for tert-butyl-(3R)-3-hydroxypyrrolidine-1-carboxylate using tert-butyl-(3S)-3-hydroxypyrrolidine-1-carboxylate (500 mg, 2.67 mmol), carbon tetrabromide (1.32 g, 4 mmol), and triphenylphosphine (1 g, 4 mmol) in $CH_2Cl_2$ (25 mL) as starting mixture. The desired compound is obtained as a clear liquid in 80% yield. $^1H$ NMR ($CDCl_3$) 4.48 (bs, 1H), 3.80-3.48 (m, 4H), 2.33-2.24 (m, 2H), 1.46 (s, 9H).

ii) Tert-butyl-(3S)-3-[(2-chloro-4-hydroxyphenyl)thio]pyrrolidine-1-carboxylate Prepared following the procedure described for tert-butyl-(3R)-3-[(2-chloro-4-hydroxy phenyl)thio]pyrrolidine-1-carboxylate using tert-butyl-(3R)-3-bromopyrrolidine-1-carboxylate (480 mg, 1.92 mmol), 2-chloro-4-hydroxythiophenol (338 mg, 2.11 mmol), and $K_2CO_3$ (795 mg, 5.76 mmol) in DMF (20 mL) as starting mixture. The desired compound is obtained as a white solid in 83% yield. $^1H$ NMR ($CDCl_3$) 7.36 (d, J=8.37 Hz, 1H), 7.00 (s, 1H), 6.74 (d, J=7.90 Hz, 1H), 3.72-3.68 (m, 1H), 3.61-3.49 (m, 2H), 3.43-3.33 (m, 2H), 2.19-2.08 (m, 1H), 1.97-1.81 (m, 1H), 1.47 (s, 1H).

iii) 3-Chloro-4-[(3S)-1-methylpyrrolidin-3-yl]thiophenol

Prepared following the procedure described for 3-chloro-4-[(3R)-1-methylpyrrolidin-3-yl]thiophenol using tert-butyl-(3S)-3-[(2-chloro-4-hydroxyphenyl)thio]pyrrolidine-1-carboxylate (250 mg, 0.76 mmol) and $AlLiH_4$ (1M in THF, 1.5 mL, 1.52 mmol) in THF (8 mL) followed by subsequent addition of 1 mL of $AlLiH_4$. The desired compound is obtained as a white foam in 35% yield. $^1H$ NMR ($CDCl_3$) 7.84 (bs, 1H), 7.27 (d, J=8.28 Hz, 1H), 6.83 (s, 1H), 6.59 (dd, J=8.46, 2.58 Hz, 1H), 3.75-3.70 (m, 1H), 3.09-3.04 (m, 1H), 2.82-2.74 (m, 2H), 2.60-2.55 (m, 1H), 2.44 (s, 3H), 2.31-2.26 (m, 1H), 1.89-1.85 (m, 1H); $^{13}C$ NMR ($CDCl_3$) 158.6, 138.1, 135.9, 122.1, 117.8, 115.4, 61.9, 55.1, 43.9, 41.9, 31.7; LCMS m/z 244 ($M^+$); Rf=0.59 ($CHCl_3$:MeOH, 8:2).

EXAMPLE 13

3-Chloro-4-[(3S)-pyrrolidin-3-yl]thiophenol.hydrochloride

Prepared following the procedure described for 3-Chloro-4-[(3R)-pyrrolidin-3-yl]thiophenol.hydrochloride using tert-butyl-(3S)-3-[(2-chloro-4-hydroxyphenyl)thio]pyrrolidine-1-carboxylate (100 mg, 0.3 mmol) and HCl (4M in dioxane, 0.15 mL, 0.6 mmol) in $CH_2Cl_2$ (5 mL). The solvent is removed in vacuo and the residue is purified by preparative HPLC (Phenominex Polar-RP, 1"×10 cm×4 micron, A: $H_2O$/TFA, 100:0.1, B: ACN/TFA, 100:0.05, gradient from A to B over 15 min, Rf=8 min, UV=254 nm). $^1H$ NMR ($CD_3OD$) 7.47 (d, J=8.55 Hz, 1H), 6.95 (s, 1H), 6.75 (dd, J=8.46, 2.61 Hz, 1H), 3.94 (m, 1H), 3.5 (m, 2H), 3.48 (m, 1H), 3.18 (m, 1H), 2.33 (m, 1H), 1.95 (m, 1H); $^{13}C$ NMR ($CD_3OD$) 161.4, 140.9, 139.3, 122.0, 118.6, 116.6, 51.9, 46.1, 46.0, 31.9; LCMS m/z 230 ($M^+$+1); Rf=0.33 (n-BuOH:$H_2O$:AcOH, 6:2:2).

EXAMPLE 14

3-Chloro-4-[(1-methylazepan-4-yl)thio]phenol

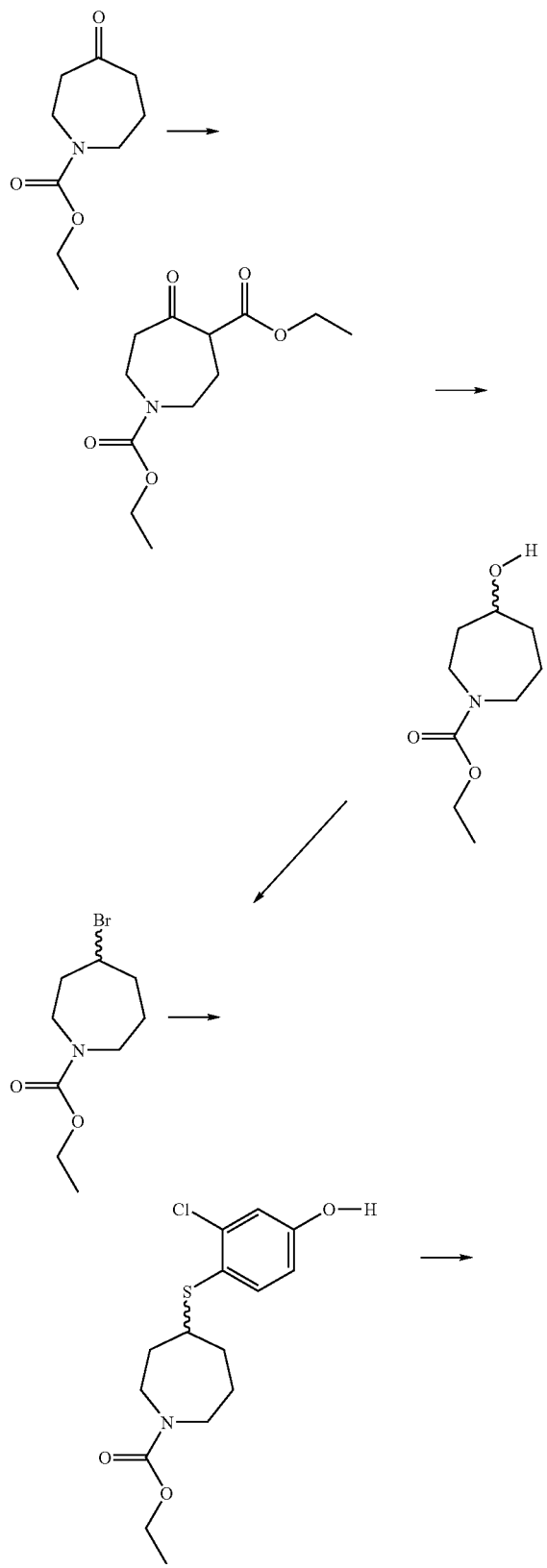

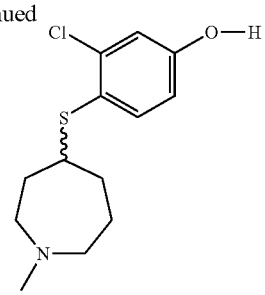

i) Diethyl-5-oxoazepane-1,4-dicarboxylate

Solutions of boron trifluoride etherate (7.4 ml, 58.4 mmol) and ethyl diazoacetate (8.1 ml) each in anhydrous di ethyl ether (6.2 ml) are added simultaneously over 45 minutes to a stirred solution of 1-carbethoxypiperidine-4-one (8.8 ml, 58.4 mmol) and anhydrous diethyl ether (20 ml), maintaining temperature between −25° C. to −33° C. under argon. After addition is completed, let mixture stir for an additional hour at −30° C. and then allow to warm to room temperature. Carefully add 30% potassium carbonate (100 ml) and extract mixture with ethyl acetate (3×20 ml). Combined organic extracts are dried over magnesium sulfate, filtered and concentrated in vacuo to give a yellow oil (15.0 g, 100%). $^1$H NMR (300 MHz, CDCl$_3$): 4.26-4.08 (m, 4H), 3.9-3.73 (m, 3H), 3.52-3.4 (2H), 2.84-2.7 (m, 2H), 2.08-2.04 (m, 2H), 1.37-1.22 (m, 6H).

ii) Ethyl-4-oxoazepane-1-carboxylate

Diethyl-5-oxoazepane-1,4-dicarboxylate (15.0 g, 58.3 mmol) is refluxed in 4N HCl (220 ml) for six hours under argon. Mixture is allowed to cool to room temperature and stirred overnight. Reaction mixture is concentrated in vacuo to afford a red oil. Added water (45 ml) and cooled to −5° C. in methanol/ice bath. Added portions of 30% potassium carbonate aqueous solution until pH 11 and then over 20 minutes added ethyl chloroformate maintaining temperature between −7° C. to −2° C. Let mixture stir for two hours at 0° C. and allow to warm to room temperature overnight. Reaction mixture is extracted with diethyl ether (2×150 ml), dried over sodium sulfate, filtered and concentrated in vacuo. The resulting brown oil is purified by chromatography using EtOAc: hexane (1:4 to pure EtOAc). This afforded a colorless oil (4.87 g, 45%); GCMS (EI) m/e 185 (M+), 170, 157, 142, 130, 112, 98, 84, 70, 56.

iii) Ethyl-4-hydroxyazepane-1-carboxylate

Ethyl-4-oxoazepane-1-carboxylate (4.5 g, 24.7 mmol) and methanol (50 ml) are stirred at 0° C. under argon. Sodium borohydride (934 mg, 24.7 mmol) is added in portions. Reaction is allowed to warm to room temperature overnight. Reaction is quenched with 5% HCl aqueous solution and concentrated in vacuo. To the resulting liquid, washed with water and extracted with ethyl acetate. Organic layers are combined, dried over sodium sulfate, filtered and concentrated in vacuo.

The resulting orange oil is purified by chromatography on silica gel using EtOAc:hexane (1:4 to pure EtOAc) as eluant to afford the product as a colorless oil (2.98 g, 65%). $^1$H NMR (300 MHz, CDCl$_3$): 4.18-4.08 (m, 2H), 3.95-3.85 (m, 1H), 3.51-3.31 (m, 3H), 2.05 (s, 1H), 2.05-1.61 (6H), 1.28 (s, 1H), 1.44-1.23 (m, 3H); LCMS (EI) m/e 210 (M+Na), 188 (M+), 170 (M−H$_2$O).

iv) Ethyl-4-bromoazepane-1-carboxylate

Triphenylphosphine (7.08 g, 27 mmol) is added to a mixture of ethyl-4-hydroxyazepane-1-carboxylate (3.37 g, 18 mmol) in methylene chloride (180 ml) at 0° C. under argon. Added carbon tetrabromide (8.95 g, 27 mmol), maintaining temperature at 0° C. Reaction mixture is allowed to warm to room temperature and stirred for 18 hours. Concentrating reaction mixture in vacuo afforded a brown oil which is purified by chromatography using EtOAc:hexane (1:9 to 1:4) giving a colorless oil (3.38 g, 75%). $^1$H NMR (300 MHz, CDCl$_3$): 4.4-4.36 (m, 1H), 4.19-4.11 (m, 2H), 3.57-3.38 (m, 4H), 2.28-1.99 (m, 5H), 1.77-1.73 (m, 1H), 1.29-1.24 (t, J=7.14 Hz).

v) Ethyl-4-[(2-chloro-4-hydroxyphenyl)thio] azepane-1-carboxylate

Ethyl-4-bromoazepane-1-carboxylate (3.38 g, 13.5 mmol), 2-chloro-4-hydroxythiophenol (2.17 g, 13.5 mmol), potassium carbonate (5.6 g, 40.5 mmol) and dimethylformamide (87 ml) afforded a light yellow oil (3.50 g, 79%). $^1$H NMR (300 MHz, CDCl$_3$): 7.4-7.34 (d, J=18 Hz, 1H), 6.99-6.98 (d, J=3 Hz, 1H), 6.74-6.7 (d, J=12 Hz, 1H), 4.23-4.12 (m, 2H), 3.67-3.25 (m, 5H), 1.98-1.63 (m, 6H), 1.29-1.25 (m 3H).

vi) 3-Chloro-4-[(1-methylazepan-4-yl)thio]phenol

To a cooled solution of 1.0M lithium aluminium hydride in tetrahydrofuran (4 ml) is added ethyl-4-[(2-chloro-4-hydroxyphenyl)thio]azepane-1-carboxylate (600 mg, 1.8 mmol) in anhydrous tetrahydrofuran (6 ml) at 0° C. under argon. After the reaction mixture is allowed to warm to room temperature overnight, cooled to 0° C. and quenched slowly with water (0.6 ml), then 15% NaOH aqueous solution (0.6 ml) and then water (1.2 ml). Stirred vigorously until a white precipitate is observed. The crude mixture is washed with brine (30 ml) and extracted with EtOAc (3×40 ml). Organic layers are combined, dried over sodium sulfate, filtered and concentrated in vacuo to give a yellow oil. Chromatography of oil using a gradient elution from chloroform to 1:4 methanol:chloroform afforded a yellow oil (330 mg, 67%). $^1$H NMR (300 MHz, CDCl$_3$): 7.33-7.29 (d, J=12 Hz, 1H), 6.89 (s, 1H), 6.63-6.6 (d, J=9 Hz, 1H), 4.21 (broad s, 1H), 3.39-3.78 (m, 1H), 2.88-2.81 (m, 2H), 2.7-2.68 (m, 2H), 2.45 (s, 3H), 2.15-2.04 (m, 2H), 1.86-1.63 (m, 4H); $^{13}$C NMR (300 MHz): 159, 139, 137, 120, 117, 115, 58, 54, 46, 45, 33, 31, 24; LCMS: m/e 272 (M+H). TLC (20% methanol in chloroform, silica gel plate, iodine stained) R$_f$ 0.45.

EXAMPLE 15 (a)

4-(Azepan-4-ylthio)-3-chlorophenol hydrobromide

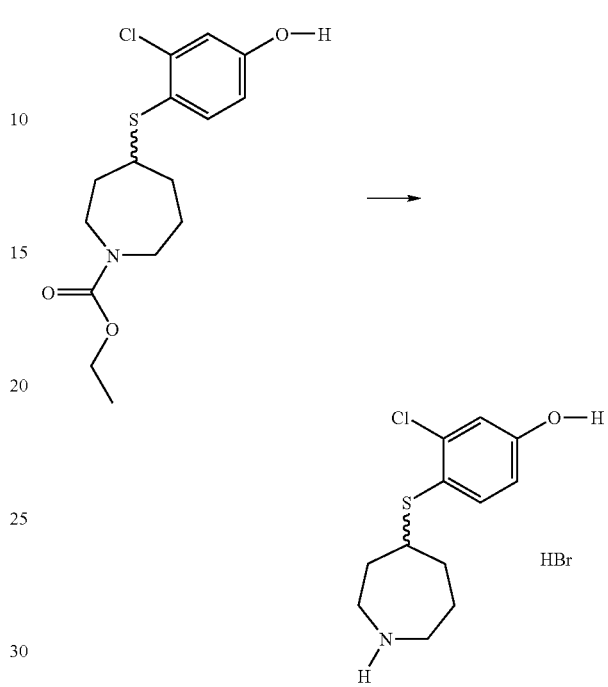

Ethyl-4-[(2-chloro-4-hydroxyphenyl)thio]azepane-1-carboxylate (210 mg) is refluxed in 48% HBr aqueous solution (5.0 ml) overnight under argon. After concentration of reaction mixture in vacuo, purification of an aliquot of the resulting brown residue (⅓ portion) by HPLC afforded a colorless oil (16 mg.) $^1$H NMR (300 MHz, CD$_3$OD): 7.44-7.4 (d, J=12 Hz, 1H), 6.92 (s, 1H), 6.74-6.70 (d, J=12 Hz, 1H), 3.45-3.35 (m, 2H), 3.31-3.29 (m, 2H), 3.23-3.14 (m, 3H), 2.15-2.03 (m, 3H), 1.91-1.69 (m, 3H); $^{13}$C NMR (300 MHz) 160, 140, 139, 122, 118, 116, 47, 47, 43, 33, 31, 23; TLC (silica gel plate, 6:2:2 n-butanol:water:glacial acetic acid, iodine stained) R$_f$ 0.6.

EXAMPLE 15 (b)

(R)-4-(Azepan-4-ylthio)-3-chlorophenol hydrobromide

EXAMPLE 15 (c)

(S)-4-(Azepan-4-ylthio)-3-chlorophenol hydrobromide

Ethyl-4-[(2-chloro-4-hydroxyphenyl)thio]azepane-1-carboxylate (1.0 g) is subjected to chromatography on a 3578:CHIRALPAK-AD column eluting with hexane:ethanol (90:10 v/v) containing 0.2% DME. There is thus obtained 420 mg each of (R)-ethyl-4-[(2-chloro-4-hydroxyphenyl)thio] azepane-1-carboxylate and (R)-ethyl-4-[(2-chloro-4-hydroxyphenyl)thio]azepane-1-carboxylate; retention times 6.8 minutes and 7.5 minutes. Each enantiomer is treated with 48% HBr aqueous solution as above to give the title compounds as pale yellow solids (250 mg).

Enantiomer 1: retention time 18.2 minutes [Chiralpak-AD (3538) eluting with hexane:ethanol (85:15 v/v) containing 0.2% DME]; LCMS 258 (100%, M+H), Rt=2.4 min.

Enantiomer 2: retention time 20.8 minutes [Chiralpak-AD (3538) eluting with hexane:ethanol (85:15 v/v) containing 0.2% DME]; LCMS 258 (95%, M+H), Rt=2.4

EXAMPLE 16

5-[(1-methyl-4-piperidinyl)sulfanyl]-1,3-dihydro-2H-benzimidazol-2-one

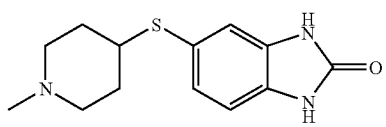

(i) 2-oxo-2,3-dihydro-1H-benzimidazole-5-sulfonyl chloride 2,3-dihydro-1H-benzimidazol-2-one (J. Chem. Soc. Perkin1, 1982, 261-270), (6.7 g, 50.0 mmole), was stirred magnetically in dry dichloromethane (50 ml). Chlorosulfonic acid (16.6 ml, 250.0 mmole) was added dropwise, at a rate that the solvent refluxed gently. Once the initial exotherm had subsided, the mixture was heated under gentle reflux for 17 to 18 hr. The cooled solution was poured onto ice. A white solid precipitated on stirring, this was filtered off, washed with water, dried at 60° C., under vacuum. Weight=9.94 g, m.p.>260° C., m/z (FIANEGL.M.)=231.1 [(M−H)⁻].

(ii) S-(2-oxo-2,3-dihydro-1H-benzimidazol-5-yl) ethanethioate 2-oxo-2,3-dihydro-1H-benzimidazole-5-sulfonyl chloride (9.9 g, 42.6 mmole) was dissolved in a mixture of acetic acid (109 ml) and acetic anhydride (35 ml). With stirring, sodium acetate (10.9 g) was then added. This reaction mixture was cooled to 10° C., and zinc dust (13.0 g), was added in portions, keeping the temperature at between 10 and 20° C. throughout additions. The mixture was then stirred at room temperature for 24 hr. The mixture was evaporated in vacuo. The residue was slurried with chloroform and sodium bicarbonate solution, filtered, the filtered off solid was washed several times with chloroform. The solid that remained was extracted into hot ethyl acetate several times, the ethyl acetate extracts were combined, washed with water, Rochelle's salt solution, dried with magnesium sulfate, filtered, evaporated in vacuo. Weight=0.184 g, m.p.=258° C. ¹H NMR, δH (300 MHz; CD₃OD) 2.26-2.32 (3H, s, CH₃). 6.94-6.98 (3H, m+s, Ar—H); m/z (FIANEGL.M)=207.1 [(M−H)⁻]

(iii) 5-[(1-methyl-4-piperidinyl)sulfanyl]-1,3-dihydro-2H-benzimidazol-2-one S-(2-oxo-2,3-dihydro-1H-benzimidazol-5-yl)ethanethioate (0.169 g, 0.81 mmole) was dissolved in dry DMF (5 ml), with stirring. To this solution was added 1-methyl-4-piperidinyl methanesulfonate (0.174 g, 0.90 mmole) and caesium fluoride (0.137 g, 0.90 mmole). This solution was brought to 80° C., and pyrrolidine (0.075 ml, 0.90 mmole) was added. This reaction mixture was kept at this temperature for 22 hr, under a nitrogen atmosphere. The reaction mixture was evaporated in vacuo, the residue was dissolved in chloroform and a little methanol, and filtered off from insoluble material. The filtrate was passed down acid ion-exchange material in a cartridge (5 g, SCX-2). The cartridge was washed with chloroform, and then methanol. The product was stripped off using 2M NH₃ in methanol. Fractions containing product were bulked, evaporated in vacuo. The residue was purified by preparative liquid chromatography. Fractions containing product were bulked, evaporated, passed down another SCX-2 cartridge to regenerate the free-base, evaporated in vacuo, then crystallised with diethyl ether to give the title compound as a colourless solid (0.0369 g). m.p.=213.8-214.7° C. ¹H NMR, δH (300 MHz; CD₃OD) 1.48-1.70 (2H, m, 2×C—H), 1.83-2.00 (2H, m, 2×C—H), 2.05-2.15 (2H, m, 2×C—H), 2.22-2.28 (3H, s, NCH₃), 2.80-2.88 (2H, m, 2×C—H), 2.93-2.03 (1H, m, HCS), 7.00-7.05 (1H, d, Ar—H), 7.05-7.20 (1H, d, Ar—H; 1H, s, Ar—H), LCMS retention time ~0.848 min, m/z (GRADPL.M)=264.1 [(M+H)⁺, 100%].

EXAMPLE 17

6-[(1-methyl-4-piperidinyl)sulfanyl]-2,4(1H,3H)-quinazolinedione

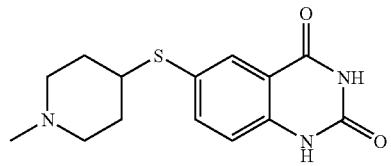

By proceeding in a similar manner to Example 16 but using 2,4(1H,3H)-quinazolinedione in place of 2,3-dihydro-1H-benzimidazol-2-one in step (i) there was prepared the title compound as a colourless solid.

m.p.>260° C. ¹H NMR, δH (300 MHz; (CD₃)₂SO) 1.42-1.56 (2H, m, 2×C—H), 1.82-1.92 (2H, m, 2×C—H), 1.95-2.08 (2H, m, 2×C—H), 2.12-2.18 (3H, s, NCH₃), 2.64-2.75 (2H, m, 2×C—H), 3.05-3.18 (1H, m, HCS), 7.12-7.18 (1H, d, Ar—H), 7.65-7.70 (1H, d, Ar—H), 7.82-7.84 (1H, s, Ar—H), 11.20-11.50 (2H, 2×s, 2×NH); LCMS retention time ~0.832 min, m/z (GRADPL.M)=292.1 [(M+H)⁺, 100%].

EXAMPLE 18

1-Methyl-6-[(1-methyl-4-piperidinyl)sulfanyl]-1,3-dihydro-2H-benzimidazol-2-one

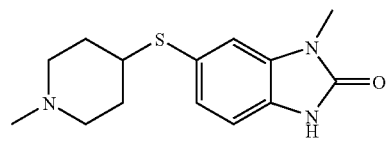

(i) N-Methyl-5-[(1-methyl-4-piperidinyl)sulfanyl]-2-nitroaniline

1-Methyl-4-piperidinethiol (J. Med. Chem. 1993, 36(22), 3261), (1.31 g, 10.0 mmole) was stirred in dry DMF (10 ml). To this was added 60% sodium hydride-oil dispersion (0.4 g, 10.0 mmole), the mixture was stirred at ambient temperature for 1 hr. To the white suspension of thiolate, 5-chloro-N-methyl-2-nitroaniline (Synth. Commun. 2000, 30(19), 3523-3526), (1.87 g. 10.0 mmole) was added. The stiffed reaction mixture was heated to 60° C., under a nitrogen atmosphere, and kept at this temperature for 18 hr. The reaction mixture was evaporated in vacuo, and the residue was dissolved in chloroform and washed with water, then brine. The organic extract was dried with magnesium sulfate, filtered, evaporated in vacuo. The residue was purified using flash chromatography, on silica-gel as stationary phase, and gradient elution with ammonia-methanol:dichloromethane (0 to 20%). Fractions containing product were bulked, evaporated in vacuo. Weight=1.83 g, m.p.=90° C. $^1$H NMR δH (300 MHz; CDCl$_3$) 1.68-1.85 (2H, m, 2×C—H), 2.05-2.20 (4H, m, 4×C—H), 2.28-2.30 (3H, s, NCH$_3$), 2.78-2.88 (2H, m, 2×C—H), 2.97-3.03 (3H, d, NCH$_3$), 3.25-3.40 (1H, m, HCS), 6.50-6.54 (1H, d, Ar—H), 6.68-6.70 (1H, s, Ar—H), 8.07-8.10 (1H, d, Ar—H) 8.10-8.20 (1H, s, NH); LCMS retention time ~2.349 min, m/z (GRADPL.M)=282.1 [(M+H)$^+$, 100%].

(ii) N$^2$-Methyl-4-[(1-methyl-4-piperidinyl)sulfanyl]-1,2-benzendiamine

N-Methyl-5-[(1-methyl-4-piperidinyl)sulfanyl]-2-nitroaniline (0.56 g, 2.0 mmole) was suspended in ethanol (30 ml), and hydrogenated at 60 psi, in the presence of 5% palladium on charcoal (0.2 g) for 1 hr. The reaction mixture was filtered, evaporated in vacuo. Weight=0.427 g of oil. LCMS retention time ~0.740 min, m/z (GRADPL.M)=252.1 [(M+H)$^+$, 100%].

(iii) 1-Methyl-6-[(1-methyl-4-piperidinyl}sulfanyl]-1,3-dihydro-2H-benzimidazol-2-one N$^2$-Methyl-4-[(1-methyl-4-piperidinyl)sulfanyl]-1,2-benzendiamine (0.427 g, 1.7 mmole) and a solution of urea (0.105 g, 1.75 mmole) in water (2 ml) were added to dimethyl acetamide (10 ml). This reaction mixture was irradiated in a microwave oven, at 300 Watts and 180° C. for a total of 3 hr 6 min. The reaction mixture was evaporated in vacuo. The residue was dissolved in methanol and added to an acid ion-exchange material in a cartridge (10 g, SCX-2). The cartridge was washed with methanol. The product was stripped off using 2M NH$_3$ in methanol. Fractions containing product were bulked, evaporated in vacuo. The residue was purified by preparative liquid chromatography. Fractions containing product were bulked, evaporated, dissolved in methanol, passed down another SCX-2 cartridge to regenerate the free-base, evaporated in vacuo. The residue was dissolved in chloroform, filtered, evaporated in vacuo and crystallised with diethyl ether to give the title compound as a colourless solid (0.0933 g). m.p.=196.4-197.6° C. $^1$H NMR δH (300 MHz; CDCl$_3$) 1.62-1.76 (2H, m, 2×C—H), 1.90-2.08 (4H, mn, 4×C—H), 2.22-2.27 (3H, s, NCH$_3$), 2.80-2.98 (2H, m, 2×C—H; 1H, m, HCS), 3.40-3.42 (3H, s, NCH$_3$), 6.93-7.00 (1H, d, Ar—H), 7.06-7.10 (1H, s, Ar—H), 7.18-7.21 (1H, d, Ar—H,) 9.04-10.04 (1H, s, NH); LCMS retention time ~1.189 min, m/z (GRADPL.M)=278.1 [(M+H)$^+$, 100%].

EXAMPLE 19

1-Methyl-6-[(1-methyl-4-piperidinyl}sulfanyl]-1,3-dihydro-2H-benzimidazole-2-thione

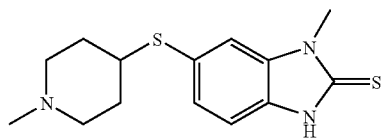

By proceeding in a similar manner to Example 18, but using thiourea in place of urea in step (iii) there was prepared the title compound as a colourless solid.

$^1$H NMR δH (300 MHz; CDCl$_3$) 1.70-1.86 (2H, m, 2×C—H), 1.90-2.08 (2H, m, 2×C—H), 2.10-2.22 (2H, m. 2×C—H), 2.22-2.30 (3H, s, NCH$_3$), 2.72-2.90 (2H, m, 2×C—H), 3.05-3.15 (1H, m, HCS), 3.74-3.80 (3H, d, NCH$_3$), 6.70-6.75 (1H, d, Ar—H), 7.15-7.20 (1H, d, Ar—H; 1H, s, Ar—H); LCMS retention time ~1.903 min, m/z (GRADPL.M)=294.1 [(M+H)$^+$, 100%].

EXAMPLE 20

5-Chloro-1-methyl-6-[(1-methyl-4-piperidinyl)sulfanyl]-1,3-dihydro-2H-benzimidazol-2-one

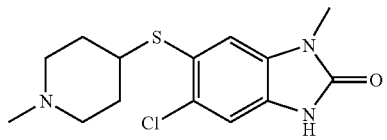

(i) 4-Chloro-N-methyl-5-[(1-methyl-4-piperidinyl)sulfanyl]-2-nitroaniline

By proceeding in a similar manner to Example 18 (i) but using 4,5-dichloro-N-methyl-2-nitroaniline (Synth. Commun. 2000, 30 (19), 3523-3526) in place of 5-chloro-N-methyl-2-nitroaniline, there was prepared the title compound as a yellow solid. m.p.=102° C. $^1$H NMR δH (300 MHz; CDCl$_3$) 1.77-1.92 (2H, m, 2×C—H), 2.08-2.30 (4H, m, 4×C—H), 2.30-2.34 (3H, s, NCH$_3$), 2.78-2.88 (2H, m, 2×C—H), 2.98-3.04 (3H, d, NCH$_3$), 3.25-3.40 (1H, m, HCS), 6.58-6.60 (1H, s, Ar—H), 8.00-8.12 (1H, s, NH), 8.15-8.18 (1H, s, Ar—H); m/z (FIAPOSL.M)=316 [(M+H)$^+$, 100%].

(ii) 4-Chloro-N$^1$-methyl-5-[(1-methyl-4-piperidinyl)sulfanyl]-1,2-benzenediamine By proceeding in a similar manner to Example 18 (ii) there was prepared the title compound as an oil, (FIAPOSL.M)=316 [(M+H)$^+$, 100%].

(iii) 5-Chloro-1-methyl-6-[(1-methyl-4-piperidinyl)sulfanyl]-1,3-dihydro-2H-benzimidazol-2-one 4-Chloro-N[1]-methyl-5-[(1-methyl-4-piperidinyl)sulfanyl]-1,2-benzenediamine (0.544 g, 1.9 mmole) was dissolved in dry THF (10 ml), triethylamine (1.06 ml, 7.6 mmole) was added, and the reaction mixture was cooled to 0° C. using an ice-salt bath. A solution of triphosgene (0.38 g, 1.26 mmole) in THF (10 ml) was added, dropwise, such that the temperature was kept below 10° C. After additions were complete, the mixture was allowed to stir at ambient temperature for 1 hr. The mixture was heated to boiling, and held at this temperature for 5 minutes. The reaction mixture was evaporated in vacuo. The residue was dissolved in chloroform, washed with water, and and then added to an acid ion-exchange material in a cartridge (10 g, SCX-2). The cartridge was washed with chloroform. The product was stripped off using 2M $NH_3$ in methanol. Fractions containing product were bulked, evaporated in vacuo. The residue was purified by preparative liquid chromatography. Fractions containing product were bulked, evaporated, passed down another SCX-2 cartridge to regenerate the free-base, evaporated in vacuo. The residue was crystallised with diethyl ether to give the title compound as a colourless solid (0.294 g).

m.p.=210.2-211.9° C. $^1$H NMR δH (300 MHz; $CD_3OD$) 1.61-1.75 (2H, m, 2×C—H), 1.90-2.02 (2H, m, 2×C—H), 2.08-2.25 (2H, m, 2×C—H), 2.25-2.28 (3H, s, $NCH_3$), 2.80-2.90 (2H, m, 2×C—H), 3.15-3.18 (1H, m, HCS), 3.35-3.42 (3H, s, $NCH_3$), 7.18-7.22 (1H, s, Ar—H), 7.32-7.35 (1H, s, Ar—H); LCMS retention time ~1.914 min, m/z (GRADPL.M)=312.0 [(M+H)$^+$, 100%].

EXAMPLE 21

3-Methyl-6-[(1-methyl-4-piperidinyl)sulfanyl]-2,4(1H,3H)-quinazolinedione

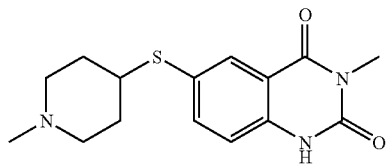

60% oil dispersion of sodium hydride (0.032 g, 0.8 mmole) was added to a stirred suspension of 6-[(1-methyl-4-piperidinyl)sulfanyl]-2,4(1H,3H)-quinazolinedione (Example 2, 0.233 g, 0.8 mmole) in dry DMF (15 ml), at ambient temperature. After 30 minutes, this was gently warmed until a clear solution was obtained. The solution was cooled to 0° C., and dimethyl sulfate (0.085 ml, 0.9 mmole) was added, the reaction mixture was then allowed to stir at ambient temperature for 60 minutes. The solution was evaporated in vacuo, and the residue was dissolved in chloroform, washed with water, dried with magnesium sulfate, filtered, evaporated in vacua. The residue was purified on a mass guided preparative liquid chromatography column to separate the mono-methylated product from dimethylated material. A free-base of the mono-methylated material was obtained from the formate salt (the form it came off the column), by dissolving the residue in warm methanol and adding to an acid ion-exchange material in a cartridge (10 g, SCX-2). The cartridge was washed with methanol. The product was stripped off using 2M $NH_3$ in methanol. Fractions containing product were bulked and evaporated in vacuo to give the title compound as a colourless solid (0.016 g) m.p.=200.8-202.6° C. $^1$H NMR δH (300 MHz; $CD_3OD$) 1.58-1.72 (2H, m, 2×C—H), 1.92-2.02 (2H, m, 2×C—H), 2.12-2.24 (2H, m, 2×C—H), 2.25-2.30 (3H, s, $NCH_3$), 2.80-2.91 (2H, m, 2×C—H), 3.07-3.22 (1H, m, HCS), 3.35-3.40 (3H, s, $NCH_3$), 7.13-7.17 (1H, d, Ar—H), 7.71-7.73 (1H, d, Ar—H), 8.05-8.08 (1H, s, Ar—H); LCMS retention time ~1.432 min, m/z (GRADPL.M)=306.1 [(M+H)$^+$, 100%].

EXAMPLE 22

3-Cyclopropylmethyl-6-[(1-methyl-4-piperidinyl)-2,4(1H,3H)-quinazolinedione

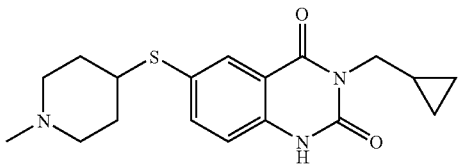

By proceeding in a similar manner to Example 21 but using cyclopropylmethyl chloride, there was prepared the title compound as a colourless solid. $^1$H nmr, δH (300 MHz, $CDCl_3$) 0.44-0.52 (4H, m, 4×C—H), 1.28-1.40 (1H, m, C—H), 1.60-1.74 (2H, m, 2×C—H), 1.92-2.12 (4H, m, 4×C—H), 2.24-2.30 (3H, s, $NCH_3$), 2.76-2.88 (2H, m, 2×C—H), 2.95-3.10 (1H, m, HCS), 3.90-3.98 (2H, d, $CH_2$), 7.02-7.04 (1H, d, Ar—H), 7.62-7.66 (1H, d, Ar—H), 8.18-8.20 (1H, s, Ar—H); LCMS retention time ~2.630 min, m/z (GRADPL.M)=346.1 [(M+H)$^+$, 100%].

EXAMPLE 23

6-(Azepan-4-ylsulfanyl)-7-chloro-1-methyl-1,3-dihydro-benzoimidazole-2-thione

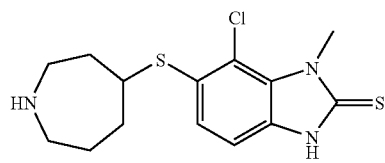

(i) 5-Oxo-azepane-1,4-dicarboxylic acid diethyl ester

Solutions of boron trifluoride etherate (14.19 g, 12.7 ml, 100 mmol) and ethyl diazoacetate (14.83 g, 13.6 ml), each in anhydrous diethyl ether (12.4 ml), were added simultaneously over 45 min to a stirred solution of 4-oxo-piperidine-1-carboxylic acid ethyl ester (17.12 g, 15.15 ml, 100 mmol) and anhydrous diethyl ether (40 ml), maintaining temperature between −25° C. and −33° C. under and atmosphere of nitrogen. After addition was completed, the mixture was stirred for an additional hour at −30° C. and then allowed to warm to room temperature. There was then carefully added 30% potassium carbonate (200 ml) and the mixture was extracted with ethyl acetate (3×40 ml). The combined organic phases were dried over magnesium sulfate, filtered and concentrated in vacuo to give a yellow oil (23.165 g, 90%). $^1$H NMR (300 MHz, CDCl3): d 4.26-4.08 (m, 4H), 3.9-3.73 (m, 3H), 3.52-3.4 (2H), 2.85-2.7 (m, 2H), 2.1-2.04 (m, 2H), 1.37-1.22 (6H).

(ii) 4-Oxo-azepane-1-carboxylic acid ethyl ester

5-Oxo-azepane-1,4-dicarboxylic acid diethyl ester (25 g, 97 mmol) was refluxed in 4N HCl (370 ml) for 6 hours under nitrogen. The mixture was allowed to cool to room temperature and stirred overnight. The reaction mixture was then concentrated in vacuo to afford a red oil which was treated with water (90 ml) and cooled to −5° C. in MeOH/ice bath. There was then added portions of 30% aqueous potassium carbonate to pH=11 and then ethyl chloroformate was added over 20 min maintaining the temperature at −5° C. The mixture was allowed to warm to 0° C. and stirred for 2 hours. The mixture was then allowed to warm to room temperature and stirred overnight. The reaction mixture extracted with diethyl ether (4×150 ml), dried over magnesium sulfate, filtrated and evaporated. The resulting brown oil was purified by silica gel chromatography using EtOAc:Hexane (20:80). This afforded a yellow oil (8.73 g, 48%). $^1$H NMR (300 MHz, CDCl3): d 4.22-4.08 (m, 2H), 3.9-3.7 (m, 4H), 3.65-3.38 (2H), 2.8-2.7 (m, 2H), 2.1-2.04 (m, 2H), 1.35-1.22 (3H).

(iii) 4-Hydroxy-azepane-1-carboxylic acid ethyl ester

4-Oxo-azepane-1-carboxylic acid ethyl ester (8 g, 43 mmol) and methanol (100 ml) were stirred at 0° C. under an atmosphere of nitrogen. Sodium borohydride (1.63 g, 43 mmol) was added in portions. The reaction mixture was stirred for 30 min at 0° C., then allowed to warm to room temperature and stirred for one hour. The reaction was quenched with 5% HCl aqueous (20 ml) and concentrated in vacuo. The resulting oil was treated with water and extracted with diethyl ether (3×50 ml). The organic phases were combined, dried over magnesium sulfate, filtrated and concentrated in vacuo. The resulting orange oil was purified by silica gel chromatography using EtOAc:Hexane (20:80). This afforded a colorless oil (4.69 g, 58%). $^1$H NMR (300 MHz, CDCl3): d 4.31-4.08 (m, 2H), 3.9-3.8 (s, 1H), 3.55-3.28 (4H), 2.12-2.08 (m, 1H), 1.92-1.7 (m, 6H), 1.35-1.22 (3H).

(iv) 4-Bromo-azepane-1-carboxylic acid ethyl ester

Triphenylphosphine (9.44 g, 36 mmol) was added to a mixture of 4-Hydroxy-azepane-1-carboxylic acid ethyl ester (4.5 g, 24 mmol) in methylene chloride at 0° C. under nitrogen. Carbon tetrabromide (11.93 g, 36 mmol) was added in portions, maintaining the temperature at 0° C. The mixture was stirred at 0° C. for 30 min and then allowed to warm to room temperature. The reaction mixture was stirred for 18 h at room temperature before concentrating the reaction mixture in vacuo to afford a brown oil, which was purified by silica gel chromatography using EtOAc:Hexane (20:80 to 50:50). This afforded a colorless oil (3.1 g, 51%). $^1$H NMR (300 MHz, CDCl3): 4.28-4.34 (m, 1H), 4.02-4.18 (m, 2H), 3.4-3.6 (m, 4H), 2.01-2.39 (m, 6H), 1.7-1.86 (m, 1H), 1.23-1.39 (m, 3H).

(v) 4-Acetylsulfanyl-azepane-1-carboxylic acid ethyl ester

Potassium thioaceate (1.36 g, 12 mmol) and dry dimethylformamide (5 ml) were added to a solution of 4-bromo-azepane-1-carboxylic acid ethyl ester (1.5 g, 6 mmol) in anhydrous tetrahydrofuran (50 ml). The reaction mixture was stirred for 18 hours at 60° C. and concentration of the reaction mixture in vacuo afforded a yellow oil, which was purified by chromatography using EtOAc:Hexane (10:90 to 40:60). This afforded a yellow oil (0.947 g, 65%). $^1$H NMR (300 MHz, CDCl3): 4.02-4.21 (m, 2H), 3.5-3.69 (m, 2H), 3.21-3.5 (m, 4H), 2.21-2.28 (m, 2H), 2.1-2.18 (m, 2H), 1.65-1.82 (m, 4H), 1.23-1.32 (m, 3H).

(vi) 4-(2-Chloro-3-methylamino-4-nitro-phenylsulfanyl)-azepane-1-carboxylic acid ethyl ester 4-Acetylsulfanyl-azepane-1-carboxylic acid ethyl ester (0.9 g, 3.7 mmol) and (2,3-dichloro-6-nitro-phenyl)-methylamine (0.811 g, 3.7 mmol) were dissolved in degassed methanol (50 ml) at room temperature. 2M NaOH aqueous (3.7 ml, 7.4 mmol) was added in portions and the reaction mixture stirred for 2.5 hours at room temperature. Concentration of the reaction mixture in vacuo afforded a brown oil, which was purified by silica gel chromatography using EtOAc:Hexane (20:80 to 50:50). This afforded the title compound as a colourless oil (1.086 g, 76%). $^1$H NMR (300 MHz, CDCl3): 7.9-8 (m, 1H), 7.01 (s, 1H), 6.5-6.6 (m, 1H), 4.02-4.25 (m, 2H), 3.26-3.56 (m, 4H), 1.86-2.1 (m, 7H), 1.23-1.29 (m, 3H). LCMS retention time ~3.938 m/z 388 [(M+H)$^+$, 97%].

(vii) 4-(4-Amino-2-chloro-3-methylamino-phenylsulfanyl)-azepane-1-carboxylic acid ethyl ester To a solution of 4-(2-chloro-3-methylamino-4-nitro-phenylsulfanyl)-azepane-1-carboxylic acid ethyl ester (1 g, 2.6 mmol) in EtOAc (40 ml) was added tin chloride dihydrate (3.3 g, 12.9 mmol). The reaction mixture was heated to reflux and stirred for 1 h. The reaction mixture was then allowed to cool down to room temperature and filtrated through a celite pad. Concentration of filtrate in vacuo afforded an orange oil, which was purified by silica gel chromatography using EtOAc:Hexane (20:80). This afforded a yellow solid (0.512 g, 55%). $^1$H NMR (300 MHz, CDCl3): 7.1-7 (m, 1H), 6.5-6.52 (m, 1H), 4.1-4.21 (m, 2H), 3.39-3.42 (m, 4H), 3.05-3.3 (m, 2H), 2.62-2.68 (m, 2H), 1.9-2.1 (m, 3H), 1.62-1.78 (m, 3H), 1.12-1.30 (m, 6H). LCMS retention time ~3.09 m/z 358 [(M+H)$^+$, 72%].

(viii) 4-(4-Chloro-3-methyl-2-thioxo-2,3-dihydro-1H-benzoimidazol-5-ylsulfanyl)-azepane-1-carboxylic acid ethyl ester To a solution of 4-(4-amino-2-chloro-3-methylamino-phenylsulfanyl)-azepane-1-carboxylic acid ethyl ester (0.584 g, 1.63 mmol) and triethylamine (0.659 g, 6.52 mmol) in diethyl ether (30 ml) at −10° C. was added thiophosgene in portions. The reaction mixture was stirred for one hour at −10° C., then allowed to warm to room temperature and stirred for one hour. Concentration of the reaction mixture in vacuo afforded a brown oil, which was purified using an SCX-2 cartridge. This afforded a brown oil (0.270 g, 41%). $^1$H NMR (300 MHz, CDCl3): 7.4-7.5 (m, 1H), 7.1-7 (m, 1H), 4.1-4.18 (m, 6H), 3.46-3.55 (m, 4H), 3.2-3.35 (m, 2H), 1.6-1.7 (m, 2H), 1.62-1.78 (m, 3H), 1.12-1.30 (m, 3H). LCMS retention time ~3.71 m/z 400 [(M+H)$^+$, 84%].

(ix) 6-(Azepan-4-ylsulfanyl)-7-chloro-1-methyl-1,3-dihydro-benzoimidazole-2-thione 4-(4-chloro-3-methyl-2-thioxo-2,3-dihydro-1H-benzoimidazol-5-ylsulfanyl)-azepane-1-carboxylic acid ethyl ester (0.1 g, 0.25 mmol) was dissolved in 37% aqueous HBr and stirred at 80° C. for 48 h. Concentration of the reaction mixture in vacuo afforded colorless oil, which was cleaned up using an SCX-2 cartridge. The filtrate was concentrated in vacuo and purified by Mass Guided HPLC to give the title compound (0.027 g, 33%). $^1$H NMR (300 MHz, CDCl3):

7.5-7.6 (s, 2H), 4.5-4.1 (m, 2H), 3.66-3.75 (m, 1H), 3.2-3.32 (m, 2H), 2.8-2.93 (m, 2H), 2.2-2.35 (m, 3H), 1.95-2.05 (m, 4H), 1.70-1.82 (m, 2H). LCMS retention time ~1.86 m/z 328 [(M+H)$^+$, 95%].

EXAMPLE 24

6-(1-Methyl-piperidin-4-ylsulfanyl)-3H-benzooxazol-2-one

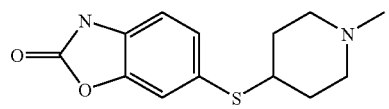

(i) 2-Oxo-2,3-dihydro-benzooxazole-6-sulfonyl chloride

To an ice bath cooled stirred slurry of 3H-Benzooxazol-2-one (20 g, 0.148 mol) in dichloromethane (150 cm$^3$) was added chlorosulphonic acid (10 cm$^3$, 0.155 mol) in two batches (1 cm$^3$ and 9 cm$^3$). After complete addition the ice bath was removed and after an hour fine crystals started to form. The reaction mixture was filtered to yield 2-oxo-2,3-dihydro-benzooxazole-6-sulfonic acid (32 g) as a fine purple solid. 12.5 g of this solid was added to dichloromethane (80 cm$^3$) and treated with 2 equivalents of SOCl$_2$ (8.5 cm$^3$, 0.116 mol). The reaction was heated to reflux for 2 hours then another 8 equivalents of SOCl$_2$ was added, this was heated at reflux overnight and then treated with a few drops of DMF rapidly causing the completion of the reaction. The reaction was cooled to room temperature then poured onto stirred crushed ice. Filtration yielded 2-oxo-2,3-dihydro-benzooxazole-6-sulfonyl chloride as a fine grey solid (12.3 g, 90%); $^1$H NMR δ$_H$ (300 MHz; D6 DMSO) 7.00-7.10 (1H, m, 1×Ar—H) and 7.38-7.49 (2H, m, Ar—H); LCMS retention time ~3.7 min, m/z (FIANEG) 231.9 [Cl$^{35}$(M)$^-$, 100%] and 233.9 [Cl$^{37}$(M)$^-$, 33%].

(ii) Thioacetic acid S-(3-acetyl-2-oxo-2,3-dihydro-benzooxazol-6-yl) ester

To an ice bath cooled, stirred mixture of 2-oxo-2,3-dihydro-benzooxazole-6-sulfonyl chloride (12.2 g, 52.2 mmol), acetic acid (150 cm$^3$) and acetic anhydride (50 cm$^3$) was added sodium acetate (15 g) followed by zinc powder (12 g). The reaction was heated to 50° C. overnight and another 12 g of zinc was added. The reaction was left at room temperature for two days then concentrated in vacuo and triturated with water (3×50 cm$^3$). The solid that was formed was filtered off and dried in vacuo to yield thioacetic acid S-(3-acetyl-2-oxo-2,3-dihydro-benzooxazol-6-yl) ester as a dry grey solid (6.98 g, 53%); $^1$H NMR δ$_H$ (300 MHz; D6 DMSO) 2.48 (3H, s, one of COCH$_3$), 2.62 (3H, s, one of COCH$_3$), 7.31-7.39 (1H, m, Ar—H), 7.54 (1H, s, Ar—H) and 7.93-8.03 (1H, m, Ar—H).

(iii) 6-(1-Methyl-piperidin-4-ylsulfanyl)-3H-benzooxazol-2-one

To a stirred mixture of thioacetic acid S-(3-acetyl-2-oxo-2,3-dihydro-benzooxazol-6-yl) ester (2.00 g, 7.97 mmol) and DMF was added methanesulfonic acid 1-methyl-piperidin-4-yl ester (2.3 g, 12.0 mmol), triphenylphosphine (1.04 g, 3.99 mmol) and K$_2$CO$_3$ (1.1 g, 7.97 mmol). This mixture was heated to 50° C. under a flow of nitrogen, treated with pyrrolidine (1.33 cm$^3$, 15.9 mmol) and then heated to 70° C. overnight. A further portion of methanesulfonic acid 1-methyl-piperidin-4-yl ester (1.5 g) was added. After a further 3 hours at 70° C., the reaction was concentrated in vacuo, treated with 1N HCl (50 ml) and the aqueous layer washed with CHCl$_3$ (50 ml). The aqueous layer was filtered and then basified using 2N NaOH, before being extracted with CHCl$_3$ (3×50 ml) The combined organics were dried (MgSO$_4$) and concentrated in vacuo (and the residue purified by Prep-LCMS (mass guided). The solution returned was passed through a SCX ion exchange cartridge and concentrated in vacuo to yield the title compound (57 mg) as colourless solid; $^1$H NMR δ$_H$ (300 MHz; CDCl$_3$) 1.53-1.70 (2H, m, 2× one of CH$_2$), 1.90-2.13 (4H, m, 4× one of CH$_2$), 2.27 (3H, s, NCH$_3$), 2.81-2.97 (3H, m, HCS and 2×NCH), 6.80-6.87 (1H, m, Ar—H) and 7.20-7.29 (2H, m, 2×Ar—H).

EXAMPLE 25

7-Chloro-6-(1-methyl-piperidin-4-ylsulfanyl)-3H-benzooxazol-2-one hydrochloride salt

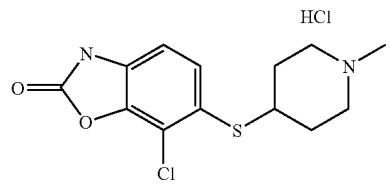

(i) 2-Chloro-3-fluoro-6-nitro-phenol 2-chloro-3-fluoro-6-nitro-phenol was prepared using a literature procedure from 2-chloro-1,3-difluoro-4-nitro-benzene. (Hayakawa, Isao; Hiramitsu, Tokiyuki; Tanaka, Yoshiaki; Chem. Pharm. Bull.; 32; 12; 1984; 4907-4913).

(ii) 2-Chloro-3-(1-methyl-piperidin-4-ylsulfanyl)-6-nitro-phenol

A 60% dispersion of sodium hydride in mineral oil (532 mg, 13.3 mmol) was pre-washed with 40-60 petroleum ether before use. To a solution of 1-methyl-piperidine-4-thiol (J. Med. Chem.; 36(22); 1993; 3261) (750 mg, 6.05 mmol) in DMF was added 2-chloro-3-fluoro-6-nitro-phenol (1.39 g, 7.26 mmol) as a solution in DMF under a flow of nitrogen forming a strong red solution. This was treated with washed sodium hydride (1 eq) and the reaction was slowly warmed to 60° C. and then after 10 minutes concentrated in vacuo to a orange oil. This was diluted with CHCl$_3$ (100 cm$^3$), H$_2$O (50 cm$^3$) and 2N NaOH (10 cm$^3$). The aqueous was isolated and washed with more CHCl$_3$ (50 ml) before being acidified to pH ~4 using 2N HCl. The resultant solid was filtered off and dried in vacuo before being triturated with methanol to give the title compound as a yellow powder (915 mg, 42%); LCMC retention ~2.72 min, m/z (FIAPOS) 303.0 [Cl$^{35}$ (M+H)$^+$, 100%] and 305.0 [Cl$^{37}$ (M+H)$^+$, 33%].

(iii) 6-Amino-2-chloro-3-(1-methyl-piperidin-4-ylsulfanyl)-phenol hydrochloride salt A slurry of 2-chloro-3-(1-methyl-piperidin-4-ylsulfanyl)-6-nitro-phenol (910 mg, 3 mmol) in methanol (20 ml) and 10% ethanolic HCl (20 ml) was treated with 5% Pd/C (500 mg). This mixture was placed under a pressurised atmosphere of hydrogen gas (60 PSI) at room temperature for one hour. The reaction was filtered through a short pad of celite® and concentrated in vacuo to yield 6-amino-2-chloro-3-(1-methyl-piperidin-4-ylsulfanyl)-phenol hydrochloride salt (925 mg, ~99%) as a purple crystalline solid; $^1$H NMR $\delta_H$ (300 MHz; D4 methanol) 1.80-2.45 (6H, m, 3×CH$_2$), 2.85-2.96 (3H, m, NCH$_3$), 3.10-3.25 (1H, m, SCH), 3.50-3.70 (2H, m, 2×NCH) and 7.18-7.40 (2H, m, 2×Ar—H); LCMC retention ~0.8 min, m/z (FIAPOS) 273.0 [Cl$^{35}$ (M+H)$^+$, 100%] and 275.1 [Cl$^{37}$ (M+H)$^+$, 33%].

(iv) 7-Chloro-6-(1-methyl-piperidin-4-ylsulfanyl)-3H-benzooxazol-2-one hydrochloride salt 6-Amino-2-chloro-3-(1-methyl-piperidin-4-ylsulfanyl)-phenol hydrochloride salt was desalted by passing through a SCX ion exchange cartridge to yield 6-amino-2-chloro-3-(1-methyl-piperidin-4-ylsulfanyl)-phenol (456 mg, 1.67 mmol) as an orange oil. This was dissolved in a mix of triethylamine (340 mg, 3.35 mmol) and tetrahydrofuran (10 ml) cooled in an ice bath and then treated with triphosgene (200 mg). After 1 hour, the reaction mixture was warmed to room concentrated, treated with 5 g silica gel and concentrated in vacuo. The residue was purified using flash chromatography on silica (CH$_2$Cl$_2$:methanolic ammonia 99:1) to yield a solid. This was treated with methanol (10 ml) and a few drops of 10% HCl in ethanol until pH 1.0 and then concentrated in vacuo to yield the title compound as a purple solid (226 mg, 45%); $^1$H NMR $\delta_H$ (300 MHz; D6 DMSO) 1.70-2.29 (6H, m, 6× one of CH$_2$), 2.60-2.79 (3H, m, NCH$_3$), 2.85-3.00 (1H, m, HCS), 3.1-3.3 (2H, m, 2×NCH), 7.01-7.11 (1H, m, Ar—H), 7.39-7.49 (1H, m, Ar—H) and 10.40-10.72 (1H, m, NH); LCMS retention time ~2.2 min, m/z (FIAPOSES) 299.1 [Cl$^{35}$ (M+H)$^+$, 100%] and 301.1 [Cl$^{37}$ (M+H)$^+$, 33%].

EXAMPLE 26

7-Chloro-6-(1-methyl-piperidin-4-ylsulfanyl)-3N-benzooxazole-2-thione hydrochloride salt

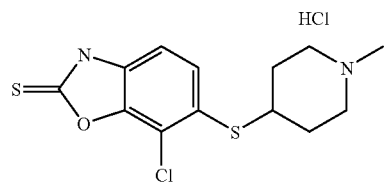

By proceeding in a similar manner to Example 25 but using thiophosgene in place of phosgene in step (iv), there was prepared the title compound as a yellow solid. $^1$H NMR $\delta_H$ (300 MHz; D4 Methanol) 1.51-2.03 (6H, m, 6× one of CH$_2$), 2.66 (3H, s, NCH$_3$), 2.8-2.9 (1H, m, HCS), 3.2-3.4 (2H, m, 2×NCH), 6.90-6.98 (1H, m, Ar—H) and 7.33-7.42 (1H, M, Ar—H); LCMS retention time ~2.7 min, m/z (FIAPOSES) 315.0 [Cl$^{35}$ (M+H)$^+$, 100%] and 317.0 [Cl$^{37}$ (M+H)$^+$, 33%].

EXAMPLE 27

7-Chloro-1-methyl-6-(1-methyl-piperidin-4-ylsulfanyl)-1,3-dihydro-benzoimidazole-2-thione

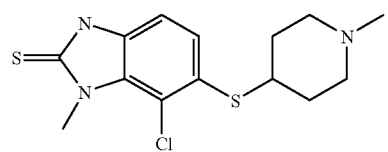

(i) [2-Chloro-3-(1-methyl-piperidin-4-ylsulfanyl)-6-nitro-phenyl]-methyl-amine To a solution of (2,3-dichloro-6-nitro-phenyl)-methyl-amine (1.49 g, 6.75 mmol) in DMF was added NaH (60% dispersion in mineral oil) (198 mg, 4.95 mmol) followed by 1-methyl-piperidine-4-thiol (J. Med. Chem.; 36(22); 1993; 3261) (837 mg, 6.41 mmol). This mixture was stirred at room temperature for 10 minutes and then concentrated in vacuo. The residue was purified using flash chromatography on silica gel (35 g) (98:2 to 85:15, CH$_2$Cl$_2$:methanolic ammonia) yielding [2-chloro-3-(1-methyl-piperidin-4-ylsulfanyl)-6-nitro-phenyl]-methyl-amine (930 mg); $^1$H NMR $\delta_H$ (300 MHz; CDCl$_3$) 1.72-1.91 (4H, m, 2×CH$_2$), 2.05-2.23 (2H, m, 1×CH$_2$), 2.30 (3H, s, CHNCH$_3$), 2.80-2.90 (2H, m, 2×NCH), 3.10-3.15 (3H, m, CNCH$_3$) 3.25-3.38 (1H, m, SCH), 6.61-6.70 (1H, m, Ar—H), 7.25 (1H, s, Ar—H) and 7.89-7.94 (1H, m, Ar—H).

(ii) 3-Chloro-N$^2$-methyl-4-(1-methyl-piperidin-4-ylsulfanyl)-benzene-1,2-diamine To a mixture of SnCl$_2$.2H$_2$O (1.33 g) and ethyl acetate was added [2-chloro-3-(1-methyl-piperidin-4-ylsulfanyl)-6-nitro-phenyl]-methyl-amine (930 mg, 2.95 mmol). The reaction was stirred at room temperature overnight, treated with another equivalent of SnCl$_2$.2H$_2$O (665 mg) and heated to 50° C. After a further 18 hrs the reaction was concentrated in vacuo and then purified using flash chromatography on silica gel (35 g) (98:2 to 80:10, CH$_2$Cl$_2$:methanolic ammonia) yielding 3-chloro-N$^2$-methyl-4-(1-methyl-piperidin-4-ylsulfanyl)-benzene-1,2-diamine.

(iii) 7-Chloro-1-methyl-6-(1-methyl-piperidin-4-ylsulfanyl)-1,3-dihydro-benzoimidazole-2-thione To an ice cooled solution of 3-chloro-N$^2$-methyl-4-(1-methyl-piperidin-4-ylsulfanyl)-benzene-1,2-diamine (560 mg, 1.96 mmol) in pyridine (309 mg, 3.92 mmol) and CH$_2$Cl$_2$ (10 ml) was added thiophosgene (225 mg, 1.96 mmol). After 4 hours the reaction was concentrated in vacuo and then purified using flash chromatography on silica gel (35 g) (98:2 to 85:15, CH$_2$Cl$_2$:methanolic ammonia) yielding a solid which was triturated with diethyl-ether, filtered, and the filtrate concentrated in vacuo to yield the title compound as a yellow solid (303 mg, 47%); $^1$H NMR $\delta_H$ (300 MHz; CDCl$_3$) 1.62-2.20 (6H, m, 6× one of CH$_2$), 2.32 (3H, m, CHNCH$_3$), 2.85-3.00 (2H, m, 2×NCH), 3.05-3.15 (1H, m, HCS), 4.18 (3H, s, NCH$_3$), 6.94-7.03 (1H, m, Ar—H), 7.25 (1H, s, Ar—H) and 7.37-7.41 (1H, m, Ar—H); LCMS retention time ~1.7 min, m/z (FIAPOSES) 328.1 [Cl$^{35}$ (M+H)$^+$, 100%] and 330.1 [Cl$^{37}$ (M+H)$^+$, 33%].

EXAMPLE 28

5,7-Dichloro-6-(1-methyl-piperidin-4-ylsulfanyl)-1H-quinolin-2-one

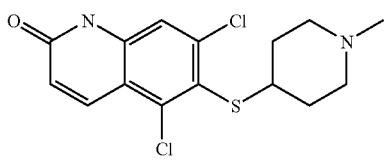

(i) 4-(2,6-Dichloro-4-nitro-phenylsulfanyl)-1-methyl-piperidine

To a solution of 1,2,3-trichloro-5-nitro-benzene (1.53 g, 6.75 mmol) in DMF was added NaH (60% dispersion in mineral oil) (198 mg, 4.95 mmol) followed by 1-methyl-piperidine-4-thiol (J. Med. Chem.; 36(22); 1993; 3261) (837 mg, 6.41 mmol). This mixture was stirred at room temperature for 10 minutes and then concentrated in vacuo. The residue was purified using flash chromatography on silica gel (35 g) (98:2 to 85:15, $CH_2Cl_2$:methanolic ammonia) yielding 4-(2,6-dichloro-4-nitro-phenylsulfanyl)-1-methyl-piperidine (1.26 g); $^1H$ NMR $\delta_H$ (300 MHz; $CDCl_3$) 1.70-1.90 (4H, m, 2×$CH_2$), 2.02-2.12 (2H, m, 1×$CH_2$), 2.25 (3H, s, $NCH_3$), 2.70-2.80 (2H, m, 2×NCH), 3.30-3.42 (1H, m, SCH) and 8.20 (2H, m, 2×Ar—H).

(ii) 3,5-Dichloro-4-(1-methyl-piperidin-4-ylsulfanyl)-phenylamine

To a mixture of $SnCl_2.2H_2O$ (1.77 g) and ethyl acetate was added 4-(2,6-dichloro-4-nitro-phenylsulfanyl)-1-methyl-piperidine (1.26 g, 3.92 mmol). The reaction was stirred at room temperature overnight and then heated to 50° C. After 18 hours the reaction was complete and product was isolated using SCX-2 ion exchange cartridges yielding 3,5-dichloro-4-(1-methyl-piperidin-4-ylsulfanyl)-phenylamine.

(iii) 5,7-Dichloro-6-(1-methyl-piperidin-4-ylsulfanyl)-1H-quinolin-2-one

To a slurry of 3,5-dichloro-4-(1-methyl-piperidin-4-ylsulfanyl)-phenylamine (1 eq) in $CH_2Cl_2$ (10 ml) and pyridine (1.5 $cm^3$) was added 3-ethoxy-acryloyl chloride (1 eq. 527 mg, 3.9 mmol) (synthesised from ethoxy-ethene according to the literature procedure of Fernandez, Franco; Garcia-Mera, Xerardo; Morales, Melvin; Rodriguez-Borges, Jose E.; Synthesis; 2; 2001; 239-242. After stirring at room temperature for one hour, the reaction was concentrated in vacuo to remove excess pyridine then treated with concentrated $H_2SO_4$ (2 $cm^3$). The reaction was quenched using 2M NaOH and diluted with $CH_2Cl_2$ (50 ml). The organic layer was concentrated in vacuo and then purified using flash chromatography on silica (35 g) (98:2 to 85:15, $CH_2Cl_2$:methanolic ammonia) yielding a solid which was triturated with diethyl-ether to form a powder which was filtered then dried in vacuo to yield the title compound (77 mg); $^1H$ NMR $\delta_H$ (300 MHz; D6 DMSO) 1.50-2.00 (6H, m, 6× one of $CH_2$), 2.12 (3H, m, $NCH_3$), 2.61-2.78 (2H, m, 2×NCH), 3.07-3.20 (1H, m, HCS), 6.60-6.70 (1H, m, Ar—H), 7.50 (1H, s, Ar—H), 8.05-8.15 (1H, m, Ar—H) and 12.1 (1H, br. s, NH); LCMS retention time ~2.9 min, m/z (FIAPOSES) 343.0 [$Cl^{35}$ & $Cl^{35}$ (M+H)$^+$, 100%] and 345.0 [$Cl^{35}$ & $Cl^{37}$ (M+H)$^+$, 66%].

EXAMPLE 29

5,7-Dimethyl-6-(1-methyl-piperidin-4-ylsulfanyl)-1H-quinolin-2-one

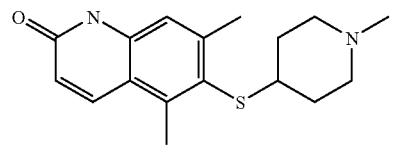

By proceeding in a similar manner to Example 28 but using 1-chloro-2,3-dimethyl-4-nitro-benzene in place of 1,2,3-trichloro-5-nitro-benzene in step (i), there was prepared the title compound as a colourless solid. $^1H$ NMR $\delta_H$ (300 MHz; $CDCl_3$) 1.61-2.00 (6H, m, 6× one of $CH_2$), 2.22 (3H, m, $NCH_3$), 2.63-2.90 (9H, m, 2×$CH_3$, HCS and 2×$CH_3$NCH), 6.64-6.75 (1H, m, Ar—H), 7.20 (1H, s, Ar—H), 8.0-8.10 (1H, m, Ar—H) and 12.0 (1H, br. s, NH); LCMS retention time ~2.8 inin, m/z (FIAPOSES) 303.1 [(M+H)$^+$, 100%].

EXAMPLE 30

5,7-Difluoro-6-(1-methyl-piperidin-4-ylsulfanyl)-1H-quinolin-2-one

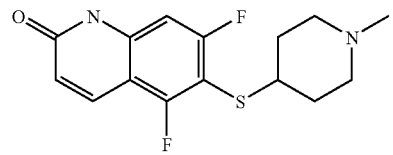

By proceeding in a similar manner to Example 28 but using 1,2,3-trifluro-5-nitro-benzene in place of 1,2,3-thichloro-5-nitro-benzene in step (i), there was prepared the title compound as a colourless solid. $^1H$ NMR $\delta_H$ (300 MHz; D6 DMSO) 1.39-1.51 (4H, m, 4× one of $CH_2$), 1.71-1.98 (2H, m, 2× one of $CH_2$), 2.10 (3H, m, $NCH_3$), 2.60-2.70 (2H, m, 2×$CH_3$NCH), 2.90-3.00 (1H, m, HCS), 6.59-6.69 (1H, m, Ar—H), 6.92-7.04 (1H, m, Ar—H), 7.90-7.98 (1H, m, Ar—H) and 12.1 (1H, br. s, NH); LCMS retention time ~2.4 min, m/z (FIAPOSES) 311.1 [(M+H)$^+$, 100%].

EXAMPLE 31

6-(1-methyl-piperidin-4-ylsulfanyl)-1H-quinolin-2-one

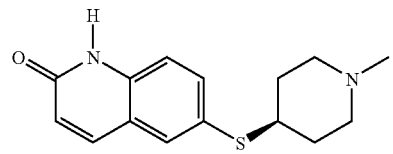

(i) 2-Oxo-1,2-dihydro-quinoline-6-sulfonyl chloride

To an ice bath cooled stirred slurry of 2-hydroxyquinoline (30.5 g, 0.210 mol) in dichloromethane (300 cm$^3$) was added chlorosulphonic acid (70 cm$^3$, 1.05 mol) in 4 equal sized batches. This was left to stir at room temperature for 2 days then slowly poured onto crushed ice. Large amount of a white solid formed in the lower chlorinated layer. This was filtered off and dried in vacuo to yield 2-Oxo-1,2-dihydro-quinoline-6-sulfonyl chloride as a dry white solid (36.3 g); $\delta_H$ (300 MHz; D6 DMSO) 6.51-6.59 (1H, m, 1×Ar—H), 7.29-7.34 (1H, m, Ar—H), 7.71-7.79 (1H, m, Ar—H), 7.90-7.96 (1H, m, Ar—H) and 8.00-8.06 (1H, m, Ar—H); LCMS retention time ~3.43 min, m/z (FIANEG) 241.9 [Cl$^{35}$(M)$^-$, 100%] and 244.0 [Cl$^{37}$(M)$^-$, 33%]. NMR and LCMS showed that this material contained some starting material as a minor impurity but no further purification was performed.

(ii) Thioacetic acid S-(2-oxo-1,2-dihydro-quinolin-6-yl) ester

To an ice bath cooled, stirred mixture of impure 2-Oxo-1,2-dihydro-quinoline-6-sulfonyl chloride (20 g, ~82 mmol), acetic acid (240 cm$^3$) and acetic anhydride (80 cm$^3$) was added sodium acetate (24 g) in three equal sized batches. Then zinc powder (20 g) was added in small batches (exothermic reaction). After one hour the ice bath was removed and the reaction was left stirring at room temperature for five days then concentrated in vacuo then triturated with water (~200 cm$^3$). The solid that was formed was filtered off and dried in vacuo to yield thioacetic acid S-(2-oxo-1,2-dihydro-quinolin-6-yl) ester as a dry grey solid (11.7 g, ~65%); $\delta_H$ (300 MHz; D6 DMSO) 2.42 (3H, s, COCH$_3$), 6.51-6.57 (1H, m, Ar—H), 7.32-7.37 (1H, m, Ar—H), 7.43-7.48 (1H, m, Ar—H), 7.72 (1H, s, Ar—H), 7.88-7.92 (1H, m, Ar—H) and 11.95 (1H, br s, N–H); LCMS retention time ~3.03 min, m/z (FIAPOS) 220 [(M+H)$^+$, 100

(iii) 6-(1-methyl-piperidin-4-ylsulfanyl)-1H-quinolin-2-one

By proceeding in a similar manner to Example 24 but using thioacetic acid S-(2-oxo-1,2-dihydro-quinolin-6-yl) ester in step (i), there was prepared the title compound as a colourless solid. $^1$H NMR $\delta_H$ (300 MHz; CDCl$_3$) 1.53-1.70 (2H, m), 1.90-2.13 (4H, m), 2.27 (3H, s), 2.81-2.97 (3H, m), 6.62-6.70 (1H, m), 7.20-7.27 (1H, m), 7.50-7.56 (1H, m), 7.62-7.64 (1H, m) and 7.70-7.73 (1H, m), FIA-MS: 275 [(M+H)$^+$, 100%

EXAMPLE 32

5-Chloro-3-methyl-6-(1-methyl-piperidin-4-ylsulfanyl)-1H-quinazoline-2,4-dione

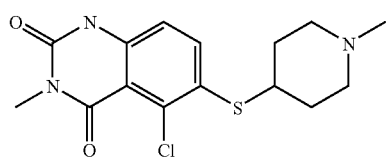

By proceeding in a similar manner to Example 25 but using N-methyl-2,3-dichloro-6-nitro-benzenecarboxamide in step (ii) there was prepared the title compound as a colourless solid. $\delta_H$ (300 MHz; CDCl$_3$) 1.72 (2H, m), 1.95 (2 h. m), 2.10 (2H, m), 2.30 (3H, s), 2.80 (2H, m), 3.18 (1H, m), 3.45 (3H, s), 7.01 (1H, d), 7.70 (1H, d), LCMS retention time ~1.18 min, m/z (FIAPOS) 340 [(M+H)$^+$, 100.

EXAMPLE 33

7-Methyl-6-(1-methyl-piperidin-4-ylsulfanyl)-3H-benzooxazol-2-one

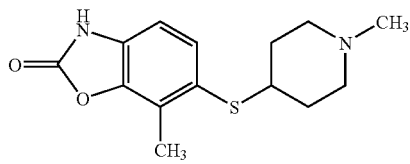

(i) 7-Methyl-3H-benzooxazol-2-one-6-sulfonic acid

7-Methyl-3H-benzooxazol-2-one [5.0 g, 33 mmol, prepared according to the procedure described in J. Org. Chem. (1982), 47(14), 2804-6] was treated with chlorosulphonic acid as described in Example 9 (i) to give the title compound as an off-white solid (4.5 g, 60%).

$\delta_H$ (300 MHz, DMSO) 2.50 (s, 3H), 6.83 (d, 1H), 7.58 (d, 1H), 11.60 (brs, 1H).

(ii) 7-Methyl-6-(1-methyl-piperidin-4-ylsulfanyl)-3H-benzooxazol-2-one

A mixture of 7-methyl-3H-benzooxazol-2-one-6-sulfonic acid (2.5 g, 11 mmol), triphenylphosphine (13 g, 50 mmol) and benzene (100 mL) was heated at reflux for 2 h under Dean and Stark conditions. The reaction was cooled and treated with iodine (5 g, 20 mmol) in small portions. The reaction was heated to reflux for a further 48 h before being cooled and washed with 2.0M aqueous sodium hydroxide (2×20 ml). The combined aqueous extracts were washed with chloroform (2×50 ml) and acidified to pH 4 with concentrated hydrochloric acid. The resultant solid was collected and dried to yield a white solid which was used directly in the next step.

This material was treated with methanesulfonic acid 1-methyl-piperidin-4-yl ester according to the procedure described in Example 9 (iii). There was thus obtained the title compound as a colourless solid.

$\delta_H$ (300 MHz; D4 methanol) 6.96 (1H, d), 7.40 (1H, d), 3.50 (2H, m), 3.35 (1H, m), 3.30 (3H, s), 3.15 (1H, m), 3.00 (2H, m), 2.50 (3H, s), 2.15 (2H, m), 1.80 (2H, m), FIA-MS: 279 [(M+H)$^+$, 100%

The invention claimed is:
1. A compound represented by Formula (I) or pharmaceutically acceptable salts thereof:

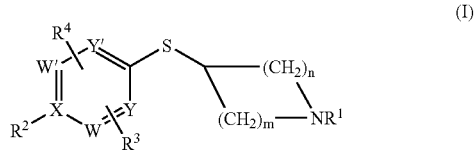

(I)

wherein:

R¹ is —H, $C_{1-12}$alkyl optionally substituted with 1, 2 or 3 groups independently selected from halogen, hydroxyl, thiol, $C_{1-4}$alkoxy or $C_{1-4}$alkylthio, or aryl-C1-4alkyl;

R² is —H,
—OH,
—C(O)—NH₂,
—NH₂,
—NH-Q-V-T, wherein Q is —C(O)—, —C(O)—NH—, —C(O)O—, or —SO₂—;

V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or SO₂$C_{1-4}$alkyl; and T is H, halogen, $C_{1-5}$alkyl, $C_{1-4}$alkoxy, nitro, aryl, aryl-$C_{1-4}$alkyl, or aryloxy unless V is H in which case T is absent; or linked back to the aromatic ring so as to form a fused bicyclic compound represented by Formula (Ia)

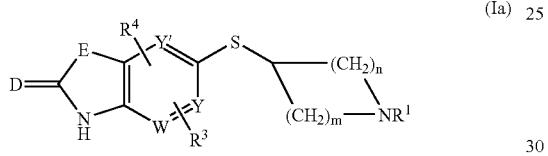

(Ia)

wherein D is O or S; and

E is O, S, NR⁵, C(R⁵)₂, O—CR⁵₂, NR⁵—CR⁵₂, NR⁵—CO, CR⁵₂—O, CR⁵₂—S(O)ᵣ, CR⁵₂—NR⁵, CR⁵₂—CR⁵₂, CO—NR⁵, or CR⁵=CR⁵;

unless X is N in which case R² is absent

R³ is H, halogen, $C_{1-4}$alkyl optionally substituted with from 1 to 3 fluorine atoms, cyano, CF₃, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—, —CO₂H, —NH₂, NH—$C_{1-4}$alkyl, aryl, hydroxy, —SO₂NH₂, —SO₂NH$C_{1-4}$alkyl, or —$C_{1-4}$alkyl-OH;

R⁴ is H, halogen, $C_{1-4}$alkyl optionally substituted with from 1 to 3 fluorine atoms, cyano, CF₃, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—, —CO₂H, —NH₂, NH—$C_{1-4}$alkyl, aryl, hydroxy, —SO₂NH₂, —SO₂NH$C_{1-4}$alkyl, or —$C_{1-4}$alkyl-OH;

R⁵ is each independently H or $C_{1-4}$alkyl;

X is C or N;
W is C or N;
W' is C or N;
Y is C or N;
Y' is C or N;

provided that there are no more than two N atoms in the aryl ring;

m is 2;
n is 2; and provided that when X, W, W', Y and Y' are all C and R³ and R⁴ are H, R² may not be —OH;

and that when one of X, Y and Y' is N and R³ and R⁴ are H, R² may not be H;

and that when R² is H, OH or NH₂ and R³ and R⁴ are H, R¹ may not be aryl-$C_{1-4}$alkyl;

and excluding compounds represented by Formula I" or pharmaceutically acceptable salts thereof:

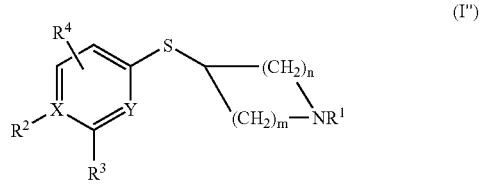

(I")

wherein:
R¹, X, Y, m and n are as defined above

R² is —H,
—NH₂,
—NH-Q-V-T, wherein Q is —C(O)— or —SO₂— and

V and T are as defined above;

unless X is N in which case R² is absent

R³ is H, halogen, $C_{1-4}$alkyl, O$C_{1-4}$alkyl, —NH₂, NH—$C_{1-4}$alkyl, or hydroxy;

R⁴ is H, halogen, $C_{1-4}$alkyl, O$C_{1-4}$alkyl, CO₂H, —NH₂, NH—$C_{1-4}$alkyl, or hydroxy.

2. A compound as claimed in claim 1 wherein

R¹ is —H, or $C_{1-12}$alkyl optionally substituted with 1, 2 or 3 groups independently selected from halogen, hydroxyl, thiol, $C_{1-4}$alkoxy or $C_{1-4}$alkylthio.

3. A compound as claimed in claim 1 or claim 2, wherein

R² is —H,
—C(O)—NH₂,
—NH₂,
—NH-Q-V-T as defined in claim 1; or linked back to the aromatic ring so as to form a fused bicyclic compound represented by Formula (Ia) as defined in claim 1;

unless X is N in which case R² is absent.

4. A compound as claimed in any one of claims 1 to 3, wherein

R² is —C(O)—NH₂,
—NH-Q-V-T as defined in claim 1; or linked back to the aromatic ring so as to form a fused bicyclic compound represented by Formula (Ia) as defined in claim 1;

unless X is N in which case R² is absent.

5. A compound as claimed in any one of claims 1 to 2, wherein

R² is —C(O)—NH₂,
—NH-Q-V-T, wherein Q is —C(O)—NH—, or —C(O)O—;

V is as defined in claim 1; and

T is as defined in claim 1; or linked back to the aromatic ring so as to form a fused bicyclic compound represented by Formula (Ia) as defined in claim 1;

unless X is N in which case R² is absent.

6. A compound as claimed in claim 1 which is represented by Formula (II) or pharmaceutically acceptable salts thereof:

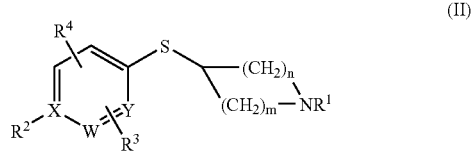

(II)

wherein:
- $R^1$ is —H; or
  - $C_{1-12}$ alkyl optionally substituted with 1, 2 or 3 groups independently selected from halogen, hydroxyl, thiol, $C_{1-4}$ alkoxy or $C_{1-4}$ alkylthio; or
  - aryl-$C_{1-4}$ alkyl;
- $R^2$ is —H;
  - —OH;
  - —C(O)—NH$_2$
  - —NH$_2$;
  - —NH-Q-V-T
- Q is —C(O)—;
  - —C(O)—NH—;
  - —C(O)O—; or
  - —SO$_2$—
- V is aryl;
  - aryl-$C_{1-12}$ alkyl;
  - diaryl-$C_{1-12}$ alkyl;
  - lactonyl; or
  - $C_{1-18}$ alkyl optionally substituted with halogen, hydroxyl, $C_{1-4}$ alkoxy, —C(O)OC$_{1-4}$ alkyl, —OC(O) $C_{1-4}$ alkyl, aryl-$C_{1-4}$ alkoxy, aryloxy, SO$_2$C$_{1-4}$ alkyl;
- T is H;
  - halogen;
  - aryl;
  - aryl-$C_{1-4}$ alkyl; or
  - aryloxy;
- unless X is N in which case $R^2$ is absent
  - $R^3$ and $R^4$ are each independently selected from H, halogen, $C_{1-4}$ alkyl, cyano, CF$_3$, OC$_{1-4}$ alkyl, aryloxy, arylC$_{1-4}$alkoxy, $C_{3-10}$cycloalkoxy, carboxy, carbonamido, —CO—, —CO$_2$H, —NH$_2$, NH—C$_{1-4}$ alkyl, aryl, hydroxy, —SO$_2$NH$_2$, —SO$_2$NHC$_{1-4}$ alkyl, —C$_{1-4}$ alkyl-OH;
- X is C or N;
- W is C or N, provided that both X and Y are not N;
- Y is C or N
- m is 2, and
- n is 2.

7. A compound as claimed in claim 6 wherein $R^1$ is H; $C_{1-6}$ alkyl optionally substituted with 1 or 2 hydroxyl groups; or aryl-$C_{14}$ alkyl.

8. A compound as claimed in claim 7 wherein $R^1$ is benzyl, p-methoxybenzyl, furanylmethyl, imidazolylmethyl, pyridinylmethyl, thienylmethyl, pyridylmethyl, N-hydroxypyridylmethyl or thiazolylmethyl.

9. A compound as claimed in any one of claims 6 to 8 wherein $R^2$ is H, $R^3$ is carbonamido (—CONH$_2$) or $C_{1-4}$ alkyl-OH, and $R^4$ is H, $C_{1-4}$alkyl, CF$_3$, halogen or cyano.

10. A compound as claimed in any one of claims 6 to 8 wherein $R^2$ is OH, and $R^3$ and $R^4$ each independently represent H, $C_{1-4}$alkyl, CF$_3$, cyano or halogen.

11. A compound as claimed in any one of claims 6 to 8 wherein $R^2$ is of formula —NH-Q-V-T; T is H and $R^3$ and $R^4$ each independently represent H, methyl, CF$_3$, chloro- or cyano-.

12. A compound as claimed in any one of claims 6 to 8 wherein $R^2$ is of formula —NH—SO$_2$-V-T; V is aryl, —C$_{1-12}$ alkyl or aryl-$C_{1-12}$ alkyl; $R_3$ is H, methyl, CF$_3$, Cl or cyano and $R^4$ is H.

13. A compound as claimed in any one of claims 6 to 8 wherein $R^2$ is of formula —NH—SO$_2$-V-T, V is selected from $C_{1-12}$ alkyl, phenyl, naphthyl, thienyl, oxazolyl, isoxazolyl, or phenyl(CH=CH)—, optionally substituted with 1, 2, 3 or 4 substituents selected from:
- —NO$_2$;
- halogen;
- —CF$_3$;
- $C_{1-12}$ alkoxy;
- $C_{1-12}$ alkylthio;
- $C_{1-12}$ alkyl;
- $C_{1-4}$ alkylsulfonyl;
- —CN;
- —OCF$_3$;
- —C(O)OC$_{1-4}$ alkyl;
- —OCH$_2$CF$_3$;
- —NHC(O)C$_{1-4}$ alkyl.

14. A compound as claimed in any one of claims 6 to 8 wherein $R^2$ is of formula —NH—SO$_2$-V-T, T is selected from H; or diazole, oxazole, isoxazole, phenyl or phenoxy, optionally substituted with 1, 2, 3 or 4 substituents selected from
- —NO$_2$;
- halogen;
- —CF$_3$;
- $C_{1-12}$ alkoxy;
- $C_{1-12}$ alkylthio;
- $C_{1-12}$ alkyl;
- $C_{1-4}$ alkylsulfonyl;
- —CN;
- —OCF$_3$;
- —C(O)OC$_{1-4}$ alkyl;
- —OCH$_2$CF$_3$;
- —NHC(O)C$_{1-4}$ alkyl.

15. A compound as claimed in any one of claims 6 to 8 wherein $R^2$ is of formula —NH—SO$_2$-V-T, V is selected from 3-chloro-4-methylphenyl, 3-chlorophenyl, 3-methoxyphenyl, 4-bromophenyl, 4-methoxyphenyl, 4-methylphenyl, naphthyl, 2,4,6-trimethylphenyl, phenyl(CH=CH)—, 4-chlorophenyl, 2-chlorophenyl, 2,5-dichlorothien-3-yl, 2,5,6-trimethyl-4-methoxyphenyl, 4-methoxyphenyl, 2,3,4-trifluorophenyl, 3-cyanophenyl, 2-methoxycarbonylthien-3-yl or 4-pentylphenyl and T is H.

16. A compound as claimed in any one of claims 6 to 8 wherein $R^2$ is of formula —NH—SO$_2$-V-T, T is 2-chloro-5-nitrophenoxy and V is phenyl.

17. A compound as claimed in any one of claims 6 to 8 wherein $R^2$ is of formula —NH—C(O)-V-T wherein V is selected from
- aryl;
- aryl-$C_{1-12}$ alkyl;
- diaryl-$C_{1-12}$ alkyl;
- lactonyl; or
- $C_{1-18}$ alkyl optionally substituted with halogen, hydroxyl, $C_{1-4}$ alkoxy, C(O)OC$_{1-4}$ alkyl, OC(O)C$_{1-4}$ alkyl, aryl-$C_{1-4}$ alkoxy, aryloxy.

18. A compound as claimed in any one of claims 6 to 8 wherein $R^2$ is of formula —NH—C(O)-V-T, and V is selected from $C_{1-12}$ alkyl, phenyl, phenyl-$C_{1-12}$ alkyl, diphenylmethyl, naphthyl, furanyl, thienyl, diazolyl, pyridinyl, thiazolyl, benzothienyl, fluorenyl, oxazolyl or isoxazolyl, optionally substituted with 1, 2, 3 or 4 substituents independently selected from
- —NO$_2$;
- halogen;
- —CF$_3$;
- $C_{1-12}$ alkoxy;
- $C_{1-12}$ alkylthio;
- $C_{1-12}$ alkyl;
- $C_{1-4}$ alkylsulfonyl;
- —CN;
- —OCF$_3$;
- —C(O)O—$C_{1-4}$ alkyl;
- —OCH$_2$CF$_3$.

19. A compound as claimed in any one of claims 6 to 8 wherein $R^2$ is of formula —NH—C(O)-V-T, T is selected from
   H;
   halogen; or
   diazole, oxazole, isoxazole, phenyl, phenoxy or benzodioxanyl optionally substituted with 1, 2, 3 or 4 substituents selected from
      —$NO_2$;
      halogen;
      —$CF_3$;
      $C_{1-12}$ alkylthio;
      $C_{1-12}$ alkoxy;
      $C_{1-12}$ alkyl;
      $C_{1-4}$ alkylsulfonyl;
      —CN;
      —$OCF_3$;
      —C(O)O—$C_{1-4}$ alkyl.

20. A compound as claimed in any one of claims 6 to 8 wherein $R^2$ is of formula —NH—C(O)N-V-T wherein V is selected from
   $C_{1-8}$ alkyl optionally substituted with halogen, hydroxyl, $C_{1-4}$ alkoxy, C(O)O$C_{1-4}$ alkyl, OC(O)$C_{1-4}$ alkyl, aryl-$C_{1-4}$ alkoxy, aryloxy;
   aryl; or
   aryl-$C_{1-12}$ alkyl.

21. A compound as claimed in any one of claims 6 to 8 wherein $R^2$ is of formula —NH—C(O)NH-V-T, V is selected from phenyl, phenyl-$C_{1-12}$ alkyl or naphthyl optionally substituted with 1, 2, 3 or 4 substituents selected from
   —$NO_2$;
   halogen;
   —$CF_3$;
   $C_{1-12}$ alkylthio;
   $C_{1-12}$ alkoxy;
   $C_{1-12}$ alkyl;
   $C_{1-4}$ alkylsulfonyl;
   —CN;
   —$OCF_3$;
   —C(O)O—$C_{1-4}$ alkyl.

22. A compound as claimed in any one of claims 6 to 8 wherein $R^2$ is of formula —NH—C(O)O-V-T, wherein V is selected from
   $C_{1-18}$ alkyl optionally substituted with halogen, hydroxyl, $C_{1-4}$ alkoxy, C(O)O$C_{1-4}$ alkyl, OC(O)$C_{1-4}$ alkyl, aryl-$C_{1-4}$ alkoxy, aryloxy;
   aryl; or
   aryl-$C_{1-12}$ alkyl.

23. A compound as claimed in any one of claims 6 to 8 wherein $R^2$ is of formula —NH—C(O)O-V-T, V is selected from phenyl or phenyl-$C_{1-12}$ alkyl optionally substituted with 1, 2, 3 or 4 substituents selected from
   —$NO_2$;
   halogen;
   —$CF_3$;
   $C_{1-12}$ alkylthio;
   $C_{1-12}$ alkoxy;
   $C_{1-12}$ alkyl;
   $C_{1-4}$ alkylsulfonyl;
   —CN;
   —$OCF_3$;
   —C(O)O—$C_{1-4}$ alkyl; or
   —$OCH_2CF_3$.

24. A compound as claimed in claim 1 wherein $R^2$ is of formula —NH—C(O)-V-T
   wherein V is H, $C_{1-6}$alkyl, $C_{3-6}$cycloalkyl, aryl or aryl-$C_{1-12}$alkyl; and
   T is H, halogen, $C_{1-5}$alkyl, $C_{1-4}$alkoxy, nitro, aryl, aryl-$C_{1-4}$alkyl, or aryloxy unless V is H in which case T is absent.

25. A compound as claimed in claim 24 wherein V is H, $C_{1-6}$alkyl or $C_{3-6}$cycloalkyl, and
   T is H unless V is H in which case T is absent.

26. A compound as claimed in claim 24 wherein V is aryl or aryl-$C_{1-12}$alkyl, and
   T is H, halogen, $C_{1-5}$alkyl, $C_{1-4}$alkoxy, nitro, aryl, aryl-$C_{1-4}$alkyl, or aryloxy.

27. A compound as claimed in claim 24 wherein V is phenyl, pyridyl, thienyl, thiazolyl, thiadiazolyl, or phenyl-$C_{1-6}$alkyl; and
   T is H, halogen, $C_{1-5}$alkyl, $C_{1-4}$alkoxy, nitro, aryl, aryl-$C_{1-4}$alkyl, or aryloxy.

28. A compound as claimed in claim 1
wherein
   $R^1$ is —H,
      $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
   $R^2$ is —$NH_2$, or
      —NH-Q-V-T, wherein Q is —C(O)—, —C(O)—NH—, —C(O)O—, or —$SO_2$—;
      V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or $SO_2C_{1-4}$alkyl; and
      T is H, halogen, aryl, aryl-$C_{1-4}$alkyl, or aryloxy unless V is H in which case T is absent,
   $R^3$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;
   $R^4$ is H, halogen, $C_{1-4}$alkyl optionally substituted with from 1 to 3 fluorine atoms, cyano, $CF_3$, $OC_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —$SO_2NH_2$, —$SO_2NHC_{1-4}$alkyl, or —$C_{1-4}$alkyl-OH;
   X is C;
   W is C or N;
   W' is C or N;
   Y is C or N;
   Y' is C or N;
provided that there are not more than two N atoms in the aryl ring and provided that at least one of W, W', Y or Y' is N;
   m is 2, and
   n is 2.

29. A compound as claimed in claim 28
wherein
   W is C;
   W' is C;
   Y' is C; and
   Y is N.

30. A compound as claimed in claim 28
wherein
   W is N;
   W' is C;
   Y' is C; and
   Y is C.

31. A compound as claimed in any one of claims 28 to 30 wherein $R^2$ is —$NH_2$.

32. A compound as claimed in any one of claims 28 to 30 wherein
R² is —NH-Q-V-T, wherein Q is —C(O)—, —C(O)—NH—, —C(O)O—, or —SO₂—;
V is H, aryl, aryl-$C_{1-12}$alkyl, diaryl-$C_{1-12}$alkyl, lactonyl, or $C_{1-18}$alkyl optionally substituted with halogen, hydroxyl, $C_{1-4}$alkoxy, —C(O)O$C_{1-4}$alkyl, —OC(O)$C_{1-4}$alkyl, aryl-$C_{1-4}$alkoxy, aryloxy, or SO₂$C_{1-4}$alkyl; and
T is H, halogen, aryl, aryl-$C_{1-4}$alkyl, or aryloxy unless V is H in which case T is absent.

33. A compound as claimed in claim 32 wherein Q is —SO₂— or —CO—.

34. A compound as claimed in claim 1 wherein:
R¹ is —H, $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
R² is linked back to the aromatic ring so as to form a fused bicyclic compound represented by Formula (Ia)

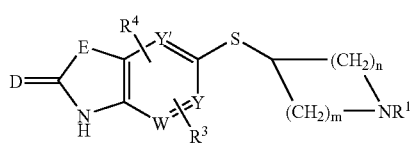

wherein D is O or S; and
E is O, S, NR⁵, or C(R⁵)₂,
R³ is H, halogen, $C_{1-4}$alkyl optionally substituted with from 1 to 3 fluorine atoms, cyano, CF₃, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —SO₂NH₂, —SO₂NH$C_{1-4}$alkyl, or —$C_{1-4}$alkyl-OH;
R⁴ is H, halogen, $C_{1-4}$alkyl optionally substituted with from 1 to 3 fluorine atoms, cyano, CF₃, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —SO₂NH₂, —SO₂NH$C_{1-4}$alkyl, or —$C_{1-4}$alkyl-OH;
R⁵ is each independently H or $C_{1-4}$alkyl;
X is C;
W is C or N;
W' is C;
Y is C or N;
Y' is C or N;
provided that there are no more than two N atoms in the aryl ring,
m is 2, and
n is 2.

35. A compound as claimed in claim 34 wherein E is O or NR⁵.

36. A compound as claimed in claim 34 wherein R⁵ is/are each independently H or $C_{1-4}$alkyl.

37. A compound as claimed in claim 1 wherein:
R is —H, $C_{1-12}$alkyl optionally substituted with 1, 2 or 3 groups independently selected from halogen, hydroxyl, thiol, $C_{1-4}$alkoxy or $C_{1-4}$alkylthio, or aryl-$C_{1-4}$alkyl;
R² is linked back to the aromatic ring so as to form a fused bicyclic compound represented by Formula (Ia)

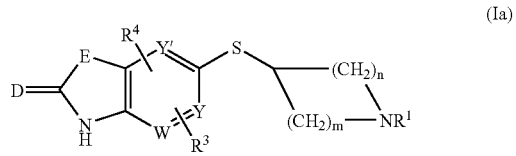

wherein D is O or S; and
E is O—CR⁵₂, NR⁵—CR⁵₂, NR⁵—CO, CR⁵₂—O, CR⁵₂—S(O)ᵣ, CR⁵₂—NR⁵, CR⁵₂—CR⁵₂, CO—NR⁵, or CR⁵=CR⁵;
R³ is H, halogen, $C_{1-4}$alkyl optionally substituted with from 1 to 3 fluorine atoms, cyano, CF₃, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —SO₂NH₂, —SO₂NH$C_{1-4}$alkyl, or —$C_{1-4}$alkyl-OH;
R⁴ is H, halogen, $C_{1-4}$alkyl optionally substituted with from 1 to 3 fluorine atoms, cyano, CF₃, O$C_{1-4}$alkyl, aryloxy, aryl$C_{1-4}$alkyl, aryl$C_{1-4}$alkoxy, $C_{3-10}$cycloalkoxy, carboxy, carbonamido, —CO—NH—$C_{1-4}$alkyl, aryl, hydroxy, —SO₂NH₂, —SO₂NH$C_{1-4}$alkyl, or —$C_{1-4}$alkyl-OH;
R⁵ is each independently H, $C_{1-4}$alkyl;
X is C;
W is C or N;
W' is C;
Y is C or N;
Y' is C or N;
provided that there are no more than two N atoms in the aryl ring;
m is 2, and
n is 2.

38. A compound as claimed in claim 37 wherein E is O—CR⁵₂, NR⁵—CR⁵₂, NR⁵—CO, CR⁵₂—CR⁵₂, or CR⁵=CR⁵.

39. A compound as claimed in claim 37 or 38 wherein E is O—CR⁵₂, NR⁵—CO, or CR⁵=CR⁵.

40. A compound as claimed in any one of claims 37 to 38 wherein R⁵ is/are each independently H or $C_{1-4}$alkyl.

41. A compound as claimed in any one of claims 6 to 8 wherein m is 2 and n is 2.

42. A compound as claimed in any one of claims 6 to 8 wherein X, Y and W are C.

* * * * *